US011859201B2

(12) United States Patent
Talukder et al.

(10) Patent No.: US 11,859,201 B2
(45) Date of Patent: Jan. 2, 2024

(54) NANOPARTICLE COMPOSITIONS CONTAINING SUGAR FUNCTIONALIZED NUCLEIC ACID CARRIERS

(71) Applicant: TIBA Biotech LLC, Cambridge, MA (US)

(72) Inventors: Poulami Talukder, Woburn, MA (US); Jasdave Chahal, Melrose, MA (US)

(73) Assignee: TIBA BIOTECH LLC, Cambridge, MA (US)

( * ) Notice: Subject to any disclaimer, the term of this patent is extended or adjusted under 35 U.S.C. 154(b) by 0 days.

(21) Appl. No.: 17/885,974

(22) Filed: Aug. 11, 2022

(65) Prior Publication Data
US 2023/0100837 A1     Mar. 30, 2023

Related U.S. Application Data

(60) Provisional application No. 63/233,505, filed on Aug. 16, 2021.

(51) Int. Cl.
| | |
|---|---|
| *C12N 15/88* | (2006.01) |
| *A61K 47/59* | (2017.01) |
| *A61K 47/54* | (2017.01) |
| *A61K 47/69* | (2017.01) |
| *A61K 9/51* | (2006.01) |
| *A61K 31/713* | (2006.01) |
| *C12N 15/113* | (2010.01) |

(52) U.S. Cl.
CPC ............ *C12N 15/88* (2013.01); *A61K 9/5146* (2013.01); *A61K 31/713* (2013.01); *A61K 47/543* (2017.08); *A61K 47/593* (2017.08); *A61K 47/6929* (2017.08); *C12N 15/113* (2013.01)

(58) Field of Classification Search
CPC ....... A61K 47/56; A61K 9/5146; C12N 15/88
See application file for complete search history.

(56) References Cited

U.S. PATENT DOCUMENTS

| | | |
|---|---|---|
| 2010/0075255 A1 | 3/2010 | Taguchi |
| 2012/0296048 A1 | 11/2012 | Etrych et al. |
| 2016/0287715 A1 | 10/2016 | Charles et al. |
| 2018/0155328 A1 | 6/2018 | Song |
| 2019/0023921 A1 | 1/2019 | Sato et al. |
| 2019/0048049 A1 | 2/2019 | Dasseux |
| 2019/0240354 A1 | 8/2019 | Abrams et al. |

FOREIGN PATENT DOCUMENTS

| | | |
|---|---|---|
| WO | 2018154387 A1 | 8/2018 |
| WO | 2019191341 A1 | 10/2019 |
| WO | 2020132196 A1 | 6/2020 |
| WO | 2021207020 A1 | 10/2021 |

OTHER PUBLICATIONS

Wu et al. Biocompatible Carbon Nanotubes Generated by Functionalization with Glycodendrimers, Angew. Chem. Int. Ed. 2008, 47, 5022-5025 (Year: 2008).*
Reichmuth, A. M. et al. "mRNA vaccine delivery using lipid nanoparticles" (2016) Therapeutic Delivery 7(5): 319-334.
Cong, L. et al. "Multiplex Genome Engineering Using CRISPR/Cas Systems" (2013) Science 339(6121): 819-823.
Jinek, M. et al. "A programmable dual RNA-guided DNA endonuclease in adaptive bacterial immunity" (2012) Science 337(6096): 816-821.
Jones, C. H. et al. "Overcoming nonviral gene delivery barriers: perspective and future" (2013) Mol. Pharmaceutics 10: 4082-4098.
Nishikawa, M. and Huang, L. "Nonviral vectors in the new millennium: delivery barriers in gene transfer" (2001) Hum. Gene Ther. 12: 861-870.
Mintzer, M. A. and Simanek, E. E. "Nonviral Vectors for Gene Delivery" (2009) Chem. Rev. 109: 259-302.
Hong, S. J. et al. "Sugar-based gene delivery systems: Current knowledge and new perspectives" (2018) Carbohydr Polym. 181: 1180-1193.
Han, S. et al. "Sugar Functionalized Synergistic Dendrimers for Biocompatible Delivery of Nucleic Acid Therapeutics" (2018) Polymers 10(9): 1034.
Geall, A. J. et al. "Nonviral delivery of self-amplifying RNA vaccines" (2012) Proc Natl Acad Sci U S A. 109(36): 14604-9.
Mortell, K. H. et al. "Recognition specificity of neoglycopolymers prepared by ring-opening metathesis polymerization" (1996) Journal of the American Chemical Society 118: 2297-2298.
Mellet, C. O. et al. "Cyclodextrin-based gene delivery systems" (2011) Chem. Soc. Rev. 40: 1586-1608.
Barnard, A. et al. "Degradable self-assembling dendrons for gene delivery: experimental and theoretical insights into the barriers to cellular uptake" (2011) J Am Chem Soc. 133(50): 20288-300.
Percec, V. et al. "Modular synthesis of amphiphilic Janus glycodendrimers and their self-assembly into glycodendrimersomes and other complex architectures with bioactivity to biomedically relevant lectins" (2013) J Am Chem Soc. 135(24): 9055-77.
Welsh, D. J. et al. "'On-off' multivalent recognition: degradable dendrons for temporary highaffinity DNA binding" (2009) Angew. Chem., Int. Ed. 48: 4047-4051.
Barnard, A. et al. "Effects of a PEG additive on the biomolecular interactions of self-assembled dendron nanostructures" (2012) Org. Biomol. Chem. 10: 8403-8409.
Gomes, C. P. "Translating chitosan to clinical delivery of nucleic acid-based drugs" (2014) MRS Bull. 39: 60-70.
Mendes, L. P. et al. "Dendrimers as Nanocarriers for Nucleic Acid and Drug Delivery in Cancer Therapy" (2017) Molecules 22(9): 1401.

(Continued)

*Primary Examiner* — James W Rogers
(74) *Attorney, Agent, or Firm* — Volpe Koenig

(57) ABSTRACT

Nanoparticle compositions for delivery of nucleic acids to subjects including carriers comprising sugar functionalized nucleic acid carriers, and therapeutic or immunogenic nucleic acid agents enclosed within the delivery molecules are described. Methods for treating or preventing diseases or conditions in a subject by administering the nanoparticle compositions that provide immune responses and synergistic therapeutic or preventive effects are provided.

28 Claims, 9 Drawing Sheets

(56) References Cited

OTHER PUBLICATIONS

Dufes, C. et al. "Dendrimers in gene delivery" (2005) Adv. Drug Delivery Rev. 57: 2177-2202.
Clare, E. T. et al. "Progress and problems with the use of viral vectors for gene therapy" (2003) Nat. Rev. Genet. 4: 346-358.
Mintzer, M. A., and Grinstaff, M. W. "Biomedical applications of dendrimers: a tutorial" (2011) Chem. Soc. Rev. 40: 173-190.
Raviña, M. et al. "Core-shell dendriplexes with sterically induced stoichiometry for gene delivery" (2010) Macromolecules 43: 6953-6961.
Nouri, A. et al. "Insight into the role of N,N-dimethylaminoethyl methacrylate (DMAEMA) conjugation onto poly(ethylenimine): cell viability and gene transfection studies" (2012) J. Mater. Sci. Mater. Med. 23: 2967-2980.
Pandita, D. et al. "Gene delivery into mesenchymal stem cells: a biomimetic approach using RGD nanoclusters based on poly-(amidoamine) dendrimers" (2011) Biomacromolecules 12: 472-481.
Rodrigues, J. et al. "Poly(alkylidenamines) dendrimers as scaffolds for the preparation of low-generation ruthenium based metallodendrimers" (2011) New J. Chem. 35: 1938-1943.
Santos, J. L. et al. "Functionalization of poly(amidoamine) dendrimers with hydrophobic chains for improved gene delivery in mesenchymal stem cells" (2010) J. Controlled Release 144: 55-64.
Santos, J. L. et al. "Osteogenic differentiation of mesenchymal stem cells using PAMAM dendrimers as gene delivery vectors" (2009) J. Controlled Release 134: 141-148.
Santos, J. L. et al. "Receptor-mediated gene delivery using PAMAM dendrimers conjugated with peptides recognized by mesenchymal stem cells" (2010) Mol. Pharmaceutics 7(3): 763-774.
Duncan, R. and Izzo, L. "Dendrimer biocompatibility and toxicity" (2005) Adv. Drug Delivery Rev. 57: 2215-2237.
Carnahan, M. A. and Grinstaff, M. W. "Synthesis and Characterization of Polyether-Ester Dendrimers from Glycerol and Lactic Acid" (2001) J. Am. Chem. Soc. 123: 2905-2906.
Carnahan, M. A. and Grinstaff, M. W. "Synthesis and Characterization of Poly(glycerol-succinic acid) Dendrim" (2001) Macromolecules 34: 7648-7655.
Carnahan, M. A. and Grinstaff, M. W. "Synthesis of Generational Polyester Dendrimers Derived from Glycerol and Succinic or Adipic Acid" (2006) Macromolecules 39: 609-616.
Boussif, O. et al. "A versatile vector for gene and oligonucleotide transfer into cells in culture and in vivo: Polyethylenimine" (1995) Proc. Natl. Acad. Sci. U.S.A. 92: 7297-7301.
World Health Organization "WHO manual on animal influenza diagnosis and surveillance" (2002) 5 Rev. 1.
Tang, Y. et al. "Apoptosis of A549 cells by small interfering RNA targeting survivin delivery using poly-β-amino ester/guanidinylated O-carboxymethyl chitosan nanoparticles" (2020) Asian J. Pharm. Sci. 15: 121-128.
Kadhim, A. "The synthesis of star copolymers for the delivery of macromolecular guest and photodynamic therapy" (2018) Doctoral Thesis, University of Sheffield.
Hanurry, E. Y. et al. "In vitro siRNA delivery via diethylenetriamine- and tetraethylenepentamine-modified carboxyl group-terminated Poly(amido)amine generation 4.5 dendrimers" (2020) Materials Science and Engineering 106(110245): 1-11.
Amis, E. J. et al. "Preparation and Characterization of Polymer/Dendrimer Blends" (2000) Project Report, Polymers Division, National Institute of Standards and Technology.
Ghobril, C. et al. "Dendrimers in nuclear medical imaging" (2012) New Journal of Chemistry 36(2): 310-323.
Mukherjee, S. et al. "Water-soluble polyacetylene: a promising tool for sustainable drug delivery?" (2017) Therapeutic Delivery 8(11): 929-932.
Han, S. C. et al. "Convergent Synthesis of PAMAM Dendrimers Containing Tetra(ethyleneoxide) at Core Using Click Chemistry" (2012) Bulletin of Korean Chemical Society 33(10): 3501-3504.
Hassett, K. J. et al. "Optimization of Lipid Nanoparticles for Intramuscular Administration of mRNA Vaccines" (2019) Mol Ther Nucleic Acids 15: 1-11.
Mui, B. L. et al. "Influence of Polyethylene Glycol Lipid Desorption Rates on Pharmacokinetics and Pharmacodynamics of siRNA Lipid Nanoparticles." (2013) Molecular therapy. Nucleic acids 2(12): e139.
Zhao, J. et al. "Polyester-based nanoparticles for nucleic acid delivery" (2018) Materials Science & Engineering C. 92: 983-994.
Hsu, H. J. et al. "Poly(ethylene glycol) Corona Chain Length Controls End-Group-Dependent Cell Interactions of Dendron Micelles" (2014) Macromolecules. 47: 6911-6918.
PubChem—SID-439633012.

* cited by examiner

Lane 1: Naked SEAP mRNA
Lane 2: PE-G2-2 deoxy Glucose-A1-Ricinoleic. SEAP mRNA NP 4a 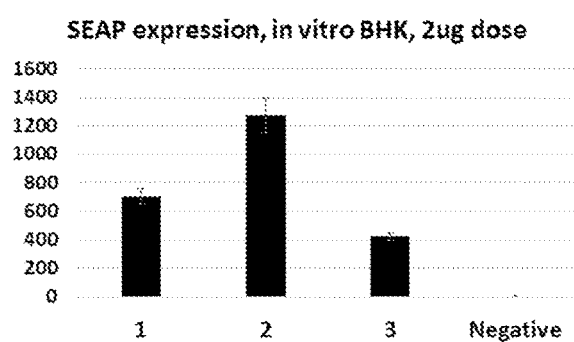 4b 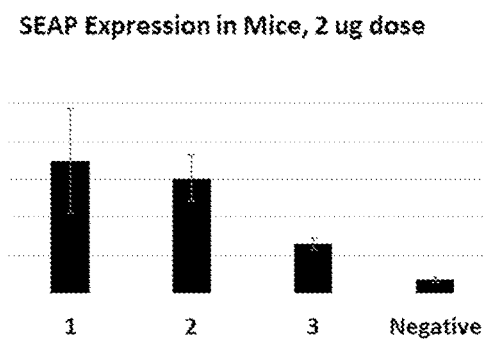
1: PE-G2-1 deoxy Glucose-A1-Ricinoleic.SEAP mRNA NP
2. PE-G2-2 deoxy Glucose-A1-Ricinoleic.SEAP mRNA NP
3. PE-G2-6 deoxy Glucose-A1-Ricinoleic.SEAP mRNA NP
Figure 4

5a
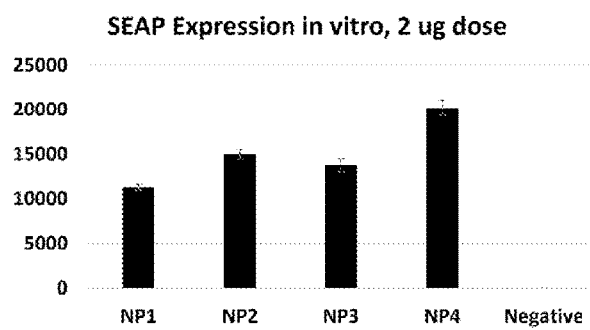
5b
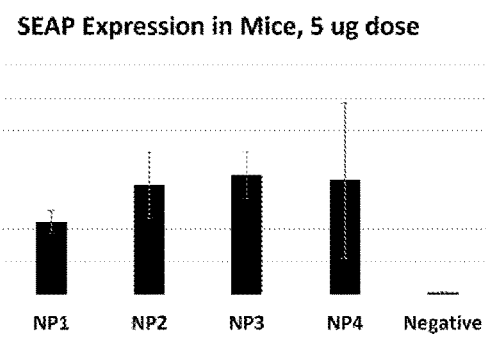
NP1: PE-G2-2 deoxy Glucose-A1-Ricinoleic.SEAP mRNA
NP2: PE-G2-2 deoxy Glucose-A5-Ricinoleic.SEAP mRNA
NP3: PE-G2-1 deoxy Mannose-A5-Ricinoleic.SEAP mRNA
NP4: PE-G2-2 deoxy Galactose-A5-Ricinoleic.SEAP mRNA
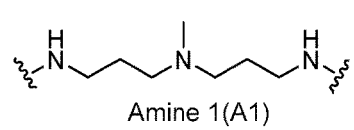
Amine 1(A1)
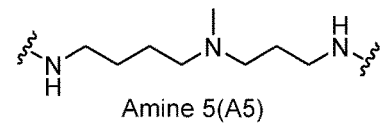
Amine 5(A5)
Figure 5

NP1: PE-G2-2 deoxy Glucose-A1-Ricinoleic.Spike Replicon RNA
NP2: PE-G2-2 deoxy Glucose-A5-Ricinoleic. Spike Replicon RNA
MC3 LNP: Dlin-MC3-DMA. Spike Replicon RNA
Amine 1(A1)
Amine 5(A5)

1: PE-G2-HexylMannose-A5-Ricinoleic.SEAP mRNA (14:0 PEG 2000)
2. PE-G2-HexylMannose-A5-Ricinoleic.SEAP mRNA (18:0 PEG 2000)
3. PE-G2-HexylMannose-A5-Ricinoleic.SEAP mRNA (ALC 0159)
4. PE-G2-HexylMannose-A5-Ricinoleic.SEAP mRNA (DMG PEG 2000)

NANOPARTICLE COMPOSITIONS CONTAINING SUGAR FUNCTIONALIZED NUCLEIC ACID CARRIERS

CROSS-REFERENCE TO RELATED APPLICATIONS

This application claims the benefit of U.S. provisional patent application No. 63/233,505, which was filed Aug. 16, 2021, was titled Nanoparticle Compositions Containing Sugar Functionalized Nucleic Acid Carriers, and is incorporated herein by reference as if fully set forth.

FIELD

The disclosure relates to carriers for efficient delivery of nucleic acids to a subject for treating or preventing diseases and/or disorders, and nanoparticle compositions comprising the carriers and nucleic acids. The disclosure also relates to methods of formulating the nanoparticle compositions and methods of treating diseases and/or disorders in the subjects with such nanoparticle compositions.

BACKGROUND

Industry continues to search for novel and safe nucleic acid carriers with multifunctional properties that can efficiently package and deliver genetic materials to a patients' cells for eventual therapeutic effect. An appropriate nonviral gene delivery system may require a delicate balance of high cellular uptake, loading capacity, biocompatibility with low toxicity and high transfection efficiency (Jones et al., 2013, Mol. Pharmaceutics 10, 4082-4098; Nishikawa and Huang, 2001 Hum. Gene Ther. 12, 861-870; and Mintzer and Simanek, 2009, Chem. Rev. 109, 259-302).

Carbohydrates, one of the most abundant natural compounds and key participants in many biological processes, are relevant across medical and industrial fields. In comparison with synthetic polymers, carbohydrates are biocompatible and have intrinsic targeting properties which together enable them to interact with cell-surface receptors (Hong et al., 2018, Carbohydr Polym. 181:1180-1193; Han et al. 2018, Polymers, 10(9), 1034) and other biological processes that enhance uptake and eventual expression. In this invention, we presented various classes of sugar-functionalized nucleic acid carriers for improved gene delivery where saccharides have been chemically conjugated to dendron or dendrimer systems for efficient and biocompatible delivery of nucleic acid.

SUMMARY

In an aspect, the invention relates to a nanoparticle composition comprising a nucleic acid carrier having the structure of one of formula Ia, Ib, Ic, Id, Ie, If, Ig, Ih, Ii, Ij, IIa or IIb:

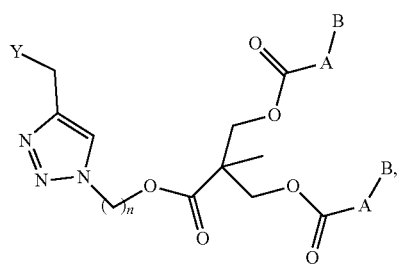

Formula Ia

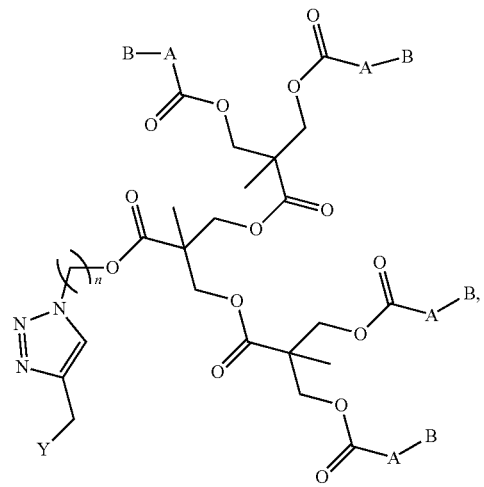

Formula Ib

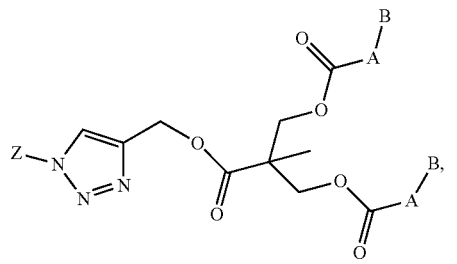

Formula Ic

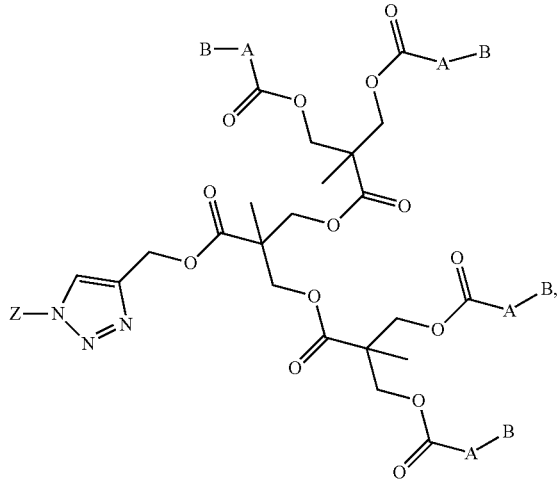

Formula Id

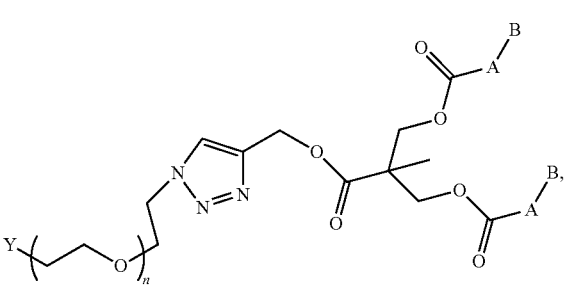

Formula Ie

Formula If

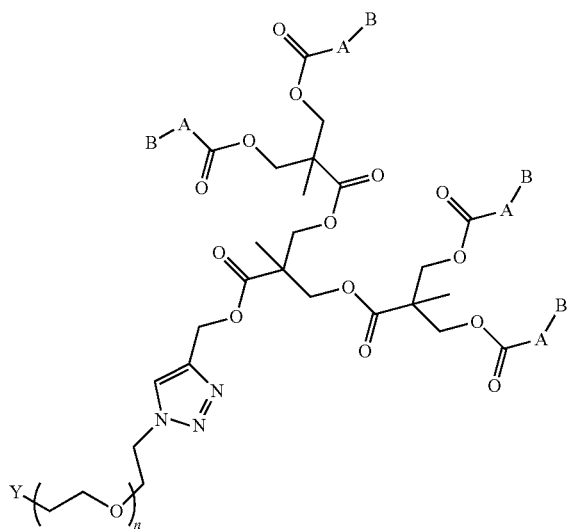

Formula Ig

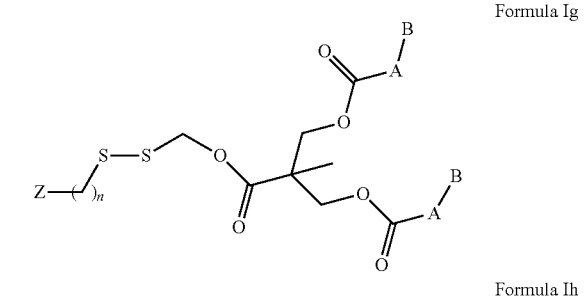

Formula Ih

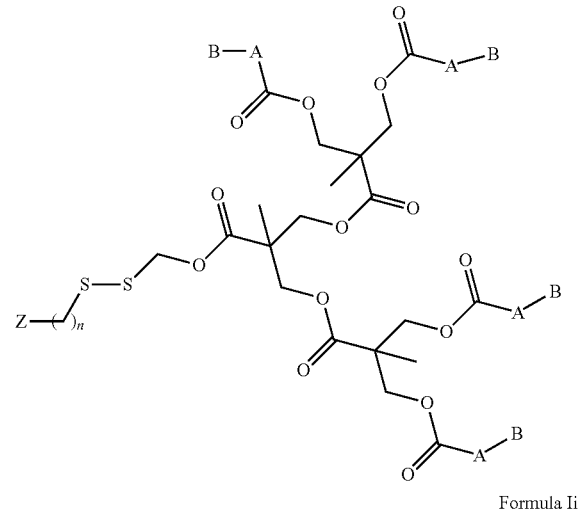

Formula Ii

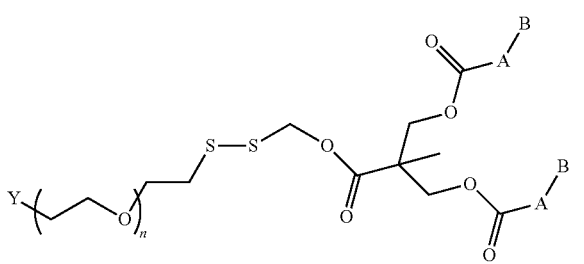

Formula Ij

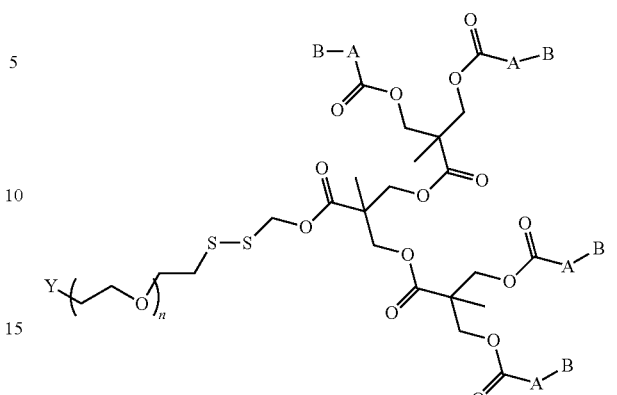

Formula IIa

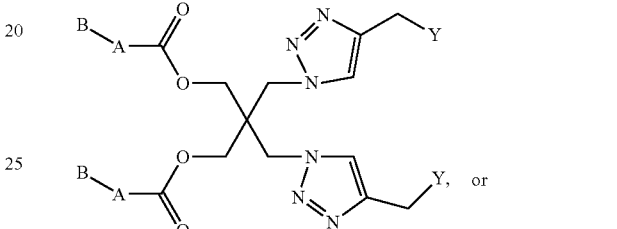

or

Formula IIb

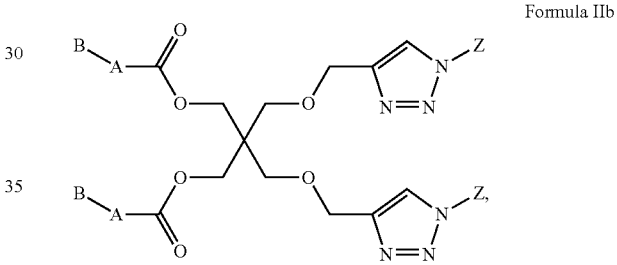

wherein A is an amine linker, B is a hydrophobic unit, n is 0 to 20, Y is a sugar moiety and Z is a deoxy sugar moiety.

In an aspect, the invention relates to a nanoparticle composition comprising at least one of the nucleic acid carriers disclosed herein, and, optionally, at least one of a therapeutic or immunogenic nucleic acid agent enclosed herein, and a conjugated lipid (e.g. PEG-Lipid) disclosed herein.

In an aspect, the invention relates to a nanoparticle composition comprising at least one of the nucleic acid carriers disclosed herein, and at least one of a therapeutic or immunogenic nucleic acid agent enclosed herein, a conjugated lipid (e.g PEG-Lipid) disclosed herein, and a mixture of a phospholipid and cholesterol or a derivative thereof to improve intracellular delivery as well as nanoparticle stability in vivo.

In an aspect, the invention relates to a method for treating or preventing a disease or condition in a subject. The method comprises administering a therapeutically effective amount of a nanoparticle composition herein to a subject.

BRIEF DESCRIPTION OF THE DRAWINGS

The following detailed description of preferred embodiments of the present invention will be better understood when read in conjunction with the appended drawings. For the purpose of illustrating the invention, particular embodiments are shown in the drawings. It is understood, however, that the invention is not limited to the precise arrangements and instrumentalities shown.

In the Drawings:

FIG. 4 illustrates quantification in vitro and in vivo of SEAP expression after administration of nanoparticle formulations with deoxy sugar-modified dendrons. SEAP mRNA formulated with PE Dendron_G2-1 deoxyGlucose-A1-Ricinoleic, PE Dendron_G2-2 deoxyGlucose-A1-Ricinoleic and PE Dendron_G2-6 deoxyGlucose-A1-Ricinoleic produced nanoparticles that resulted in SEAP protein production.

FIG. 5 illustrates quantification in vitro and in vivo of SEAP expression after administration of nanoparticle formulations based on deoxy sugar-modified dendrons. SEAP-encoding mRNA was formulated with PE Dendron_G2-2 deoxyGlucose-A1-Ricinoleic, PE Dendron_G2-2 deoxy-Glucose-A5-Ricinoleic, PE Dendron_G2-1 deoxyMannose-A5-Ricinoleic and PE Dendron_G2-2 deoxyGalactose-A5-Ricinoleic to generate nanoparticles that were administered to cells in vitro or to mice.

FIG. 7 illustrates the distribution of the nanoparticle compositions measured as the intensity based on size (d) of the nanoparticles where SEAP mRNA was formulated with PE Dendron_G2-HexylMannose-A5-Ricinoleic (DMG PEG2000 as PEG-lipid conjugate).

FIG. 8 illustrates quantification in vivo of SEAP expression after administration of nanoparticle formulations with sugar-modified dendrons. SEAP mRNA formulated with PE Dendron_G2-HexylMannose A5-Ricinoleic, produced nanoparticles that resulted in SEAP protein production.

FIG. 9 illustrates the distribution of the nanoparticle compositions measured as the intensity based on size (d) of the nanoparticles.

DETAILED DESCRIPTION

Certain terminology is used in the following description for convenience only and is not limiting.

The term "substitute" refers to the ability to change one functional group, or moiety, of a compound for another functional group or moiety, provided that the valency of all atoms on the parent structure is maintained. The substituted group is interchangeably referred herein as "substitution" or "substituent." When more than one position in any given structure is substituted with more than one substituent selected from a specified group, the substituent may be either the same or different at every position.

The term "amine linker" as used herein, refers to an amine-containing linker that links or connects hydrophobic units (described as component "B" herein for convenience) with the terminal chemical groups present on a dendrimer or dendron surface. Amines present in the amine linker are functional groups that contain a basic nitrogen atom with a lone pair. Amines are formally derivatives of ammonia, wherein one or more hydrogen atoms have been replaced by a substituent, for example an alkyl group.

The term "alkyl" as used herein, means a straight or branched chain hydrocarbon containing from 1 to 28, preferably 1 to 20, carbon atoms unless otherwise specified. An alkyl group may have 1, 2, 3, 4, 5, 6, 7, 8, 9, 10, 11, 12, 13, 14, 15, 16, 17, 18, 19, 20, 21, 22, 23, 24, 25, 26, 27, or 28 carbon atoms, or a number of carbon atoms in a range selected from any two of the foregoing values. Alkyl chain length may be used to control hydrophobicity and self-assembly properties of a nucleic acid carrier.

The term "surface groups" as used herein, means terminal groups on the surface of nucleic acid carriers. The surface of the nucleic acid carriers herein are modified with hydrophobic units (described as component "B" herein) in order to assist self-assembly properties.

Numerical values or ranges preceded by "about" refer to the explicitly recited numbers, and the numbers within the experimental error of the measure contemplated. Embodiments described with the modifier "about" may be altered to remove "about" in order to form further embodiments herein. Likewise, embodiments described without the modifier "about" may be altered to add "about" in order to form further embodiments herein.

A range expressed as being between two numerical values, one as a low endpoint and the other as a high endpoint, includes the values between the numerical values and the low and high endpoints. Embodiments herein include subranges of a range herein, where the subrange includes a low and high endpoint of the subrange selected from any increment within the range selected from each single increment of the smallest significant figure, with the condition that the high endpoint of the subrange is higher than the low endpoint of the subrange.

Further embodiments herein include replacing one or more "including" or "comprising" in an embodiment with "consisting essentially of" or "consisting of." "Including" and "comprising," as used herein, are open ended, include the elements recited, and do not exclude the addition of one or more other element. "Consisting essentially of" means that addition of one or more element compared to what is recited is within the scope, but the addition does not materially affect the basic and novel characteristics of the combination of explicitly recited elements. "Consisting of" refers to the recited elements, but excludes any element, step, or ingredient not specified.

The words "a" and "one," as used in the claims and in the corresponding portions of the specification, are defined as including one or more of the referenced items unless specifically stated otherwise. This terminology includes the words above specifically mentioned, derivatives thereof, and words of similar import. The phrase "at least one" followed by a list of two or more items, such as "A, B, or C" or "A, B, and C" means any individual one of A, B or C as well as any combination thereof.

An embodiment comprises a nanoparticle composition comprising a nucleic acid carrier having the structure of one of formula Ia, Ib, Ic, Id, Ie, If, Ig, Ih, Ii, Ij, IIa or IIb:

Figure 1:
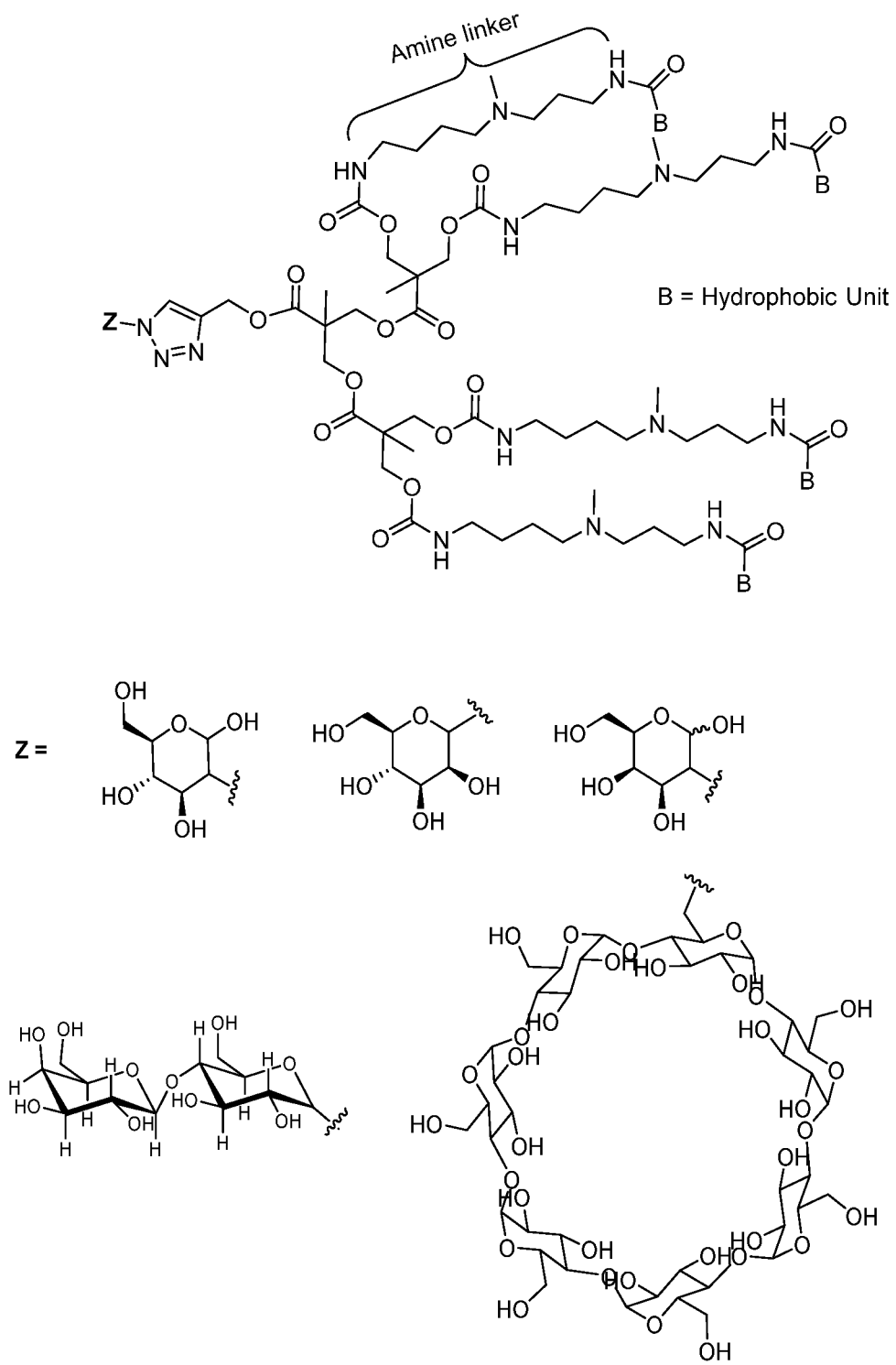
FIG. 1 is a schematic drawing of generation 2 modified polyester dendron with amine and ricinoleic acid tail as the hydrophobic unit where the focal point of the dendron is modified with various kinds of deoxy sugar.

Formula Ia
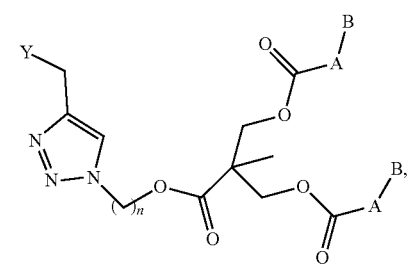
Formula Ie
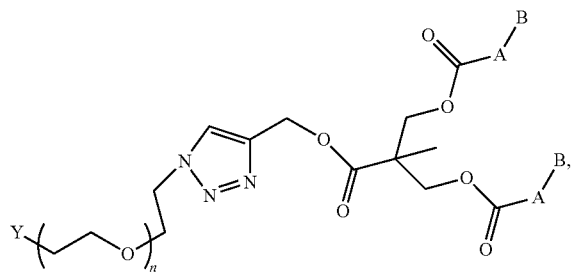
Formula Ib
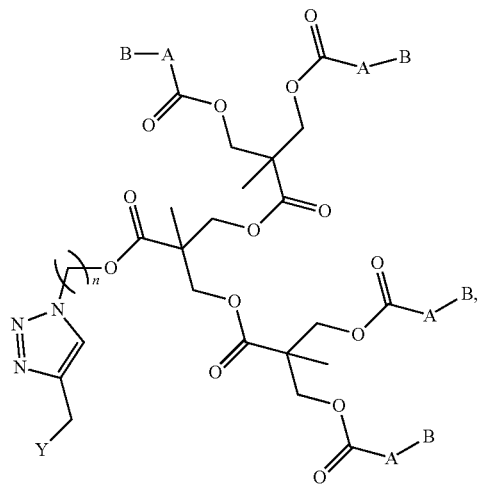
Formula If
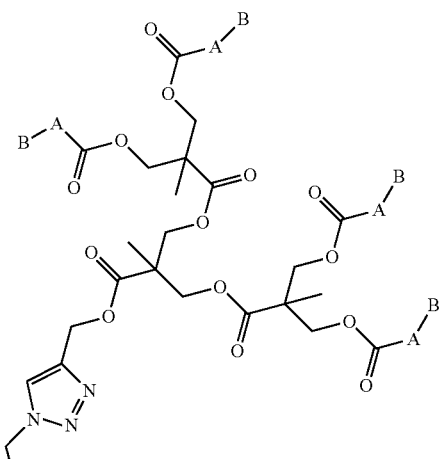
Formula Ic
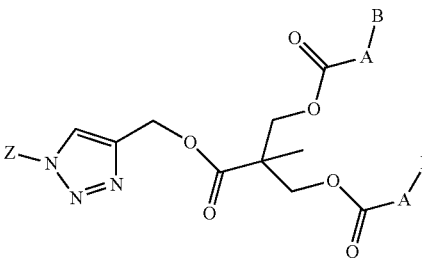
Formula Ig
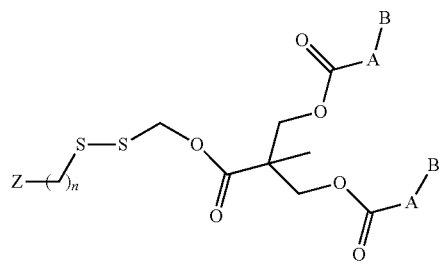
Formula Id
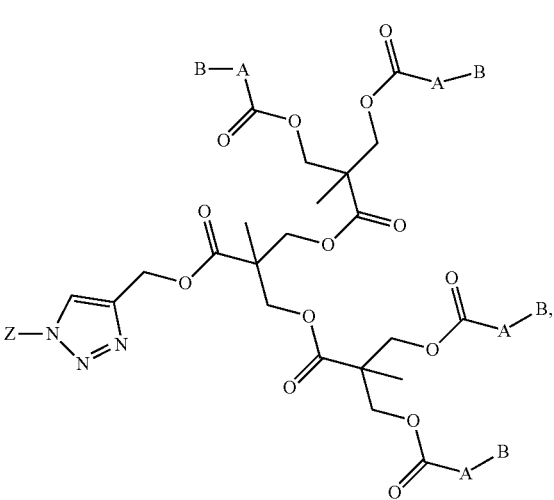
Formula Ih
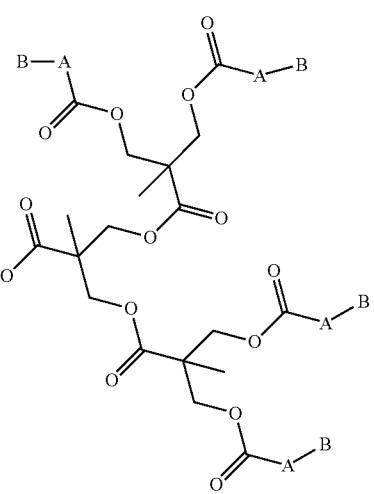

-continued

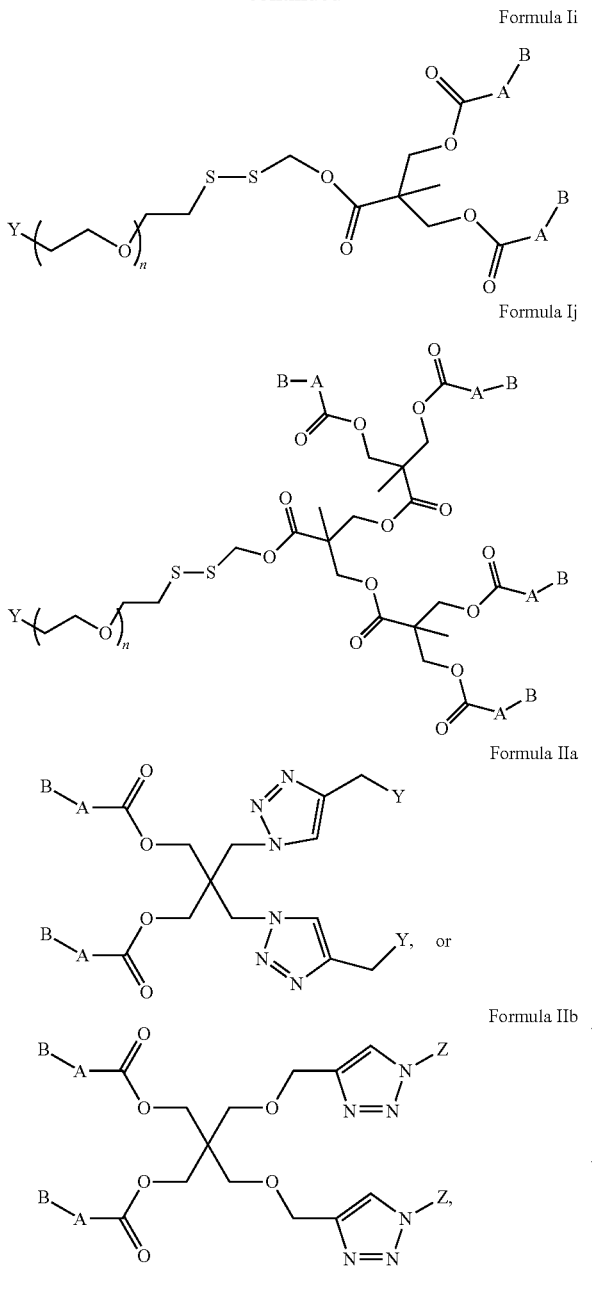

Formula Ii

Formula Ij

Formula IIa

Formula IIb wherein A is an amine linker. B is a hydrophobic unit, n is 0 to 20. Y is a sugar moiety and Z is a deoxy sugar moiety.

The amine linker A is a moiety that imparts proton-accepting functionality to the nucleic acid carrier molecule by containing one or more nitrogen atoms with lone pairs. The amine linker is thus able to accept a free proton (H+) under acidic conditions. In preferred embodiments the nitrogen atom(s) are present in the form of secondary or tertiary amines. The amine linker may be derived from N1-(2-aminoethyl)ethane-1,2-diamine, N1-(2-aminoethyl)propane-1,3-diamine, N1-(3-aminopropyl)propane-1,3-diamine, N1,N1'-(ethane-1,2-diyl)bis(ethane-1,2-diamine), N1,N1'-(ethane-1,2-diyl)bis(N2-(2-aminoethyl)ethane-1,2-diamine), N1-(2-(4-(2-aminoethyl)piperazin-1-yl)ethyl)ethane-1,2-diamine, N1-(2-aminoethyl)-N1-methylethane-1,2-diamine, N1-(3-aminopropyl)-N1-methylpropane-1,3-diamine, N1-(3-aminopropyl)-N1-ethylpropane-1,3-diamine, 3-((3-aminopropyl)(methyl)amino)propan-1-ol, 3,3'-(methylazanediyl)bis(propan-1-ol), N1-(3-aminopropyl)-N1-methylbutane-1,4-diamine, 4-((3-aminopropyl)(methyl)amino)butan-1-ol, 4-((3-hydroxypropyl)(methyl)amino)butan-1-ol, 4-((3-hydroxypropyl)(methyl)amino)butan-1-ol, N1-(4-aminobutyl)-N1-methylbutane-1,4-diamine, 4-((4-aminobutyl)(methyl)amino)butan-1-ol, 4,4'-(methylazanediyl)bis(butan-1-ol), 3-((3-aminopropyl)(ethyl)amino)propan-1-ol, 3,3'-(ethylazanediyl)bis(propan-1-ol), N1-(3-aminopropyl)-N1-ethylbutane-1,4-diamine, 4-((3-aminopropyl)(ethyl)amino)butan-1-ol, 4-(ethyl(3-hydroxypropyl)amino)butan-1-ol, N1-(2-aminoethyl)-N1-methylpropane-1,3-diamine, N1-(4-aminobutyl)-N1-ethylbutane-1,4-diamine, 4,4'-(ethylazanediyl)bis(butan-1-ol), 3-((3-aminopropyl)amino)propan-1-ol, N1-(3-aminopropyl)butane-1,4-diamine, 4-((3-hydroxypropyl)amino)butan-1-ol, N1-(4-aminobutyl)butane-1,4-diamine, 3,3'-azanediylbis(propan-1-ol), 4-((3-aminopropyl)amino)butan-1-ol, 4,4'-azanediylbis(butan-1-ol), N1,N1'-(butane-1,4-diyl)bis(propane-1,3-diamine), 2-(bis(3-aminopropyl)amino)ethan-1-ol, 2-((4-aminobutyl)(3-aminopropyl)amino)ethan-1-ol or 2-(bis(4-aminobutyl)amino)ethan-1-ol. For reference, the structures of the amine linkers derived from above amines are presented pictorially in the following structures where the pKa values of the amine present in the linkers were calculated using ACD/percepta pKa prediction tool:

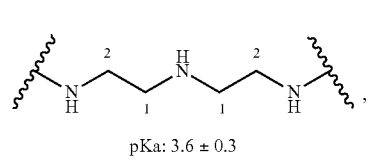

(1)

pKa: 3.6 ± 0.3

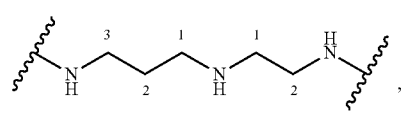

(2)

pKa: 5.7 ± 0.1

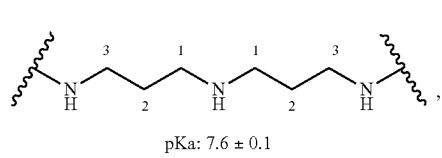

(3)

pKa: 7.6 ± 0.1

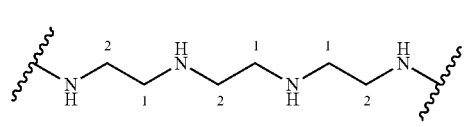

(4)

pKa: 3.1 ± 0.4

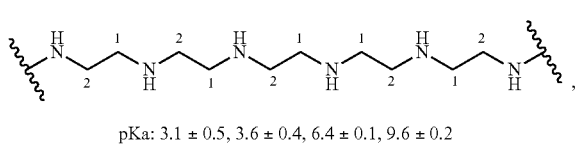

(5)

pKa: 3.1 ± 0.5, 3.6 ± 0.4, 6.4 ± 0.1, 9.6 ± 0.2

(6)
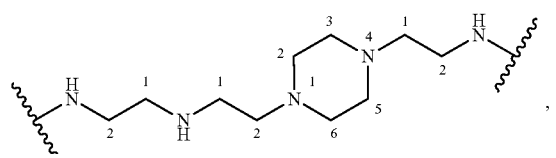
pKa: 3.1 ± 0.5, 3.6 ± 0.4, 6.4 ± 0.1, 9.6 ± 0.2
(7)
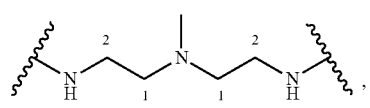
pKa: 3.3 ± 0.3
(8)
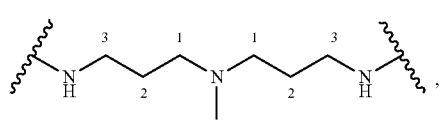
pKa: 6.7 ± 0.5
(9)
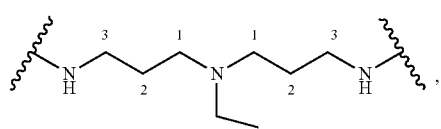
pKa: 8.1 ± 0.5
(10)
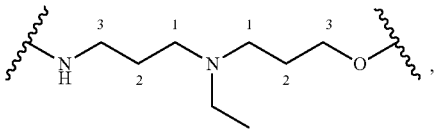
pKa: 7.8 ± 0.5
(11)
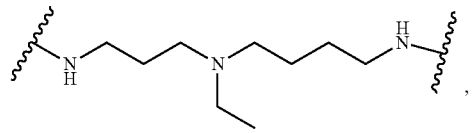
pKa: 7.7 ± 0.5
(12)
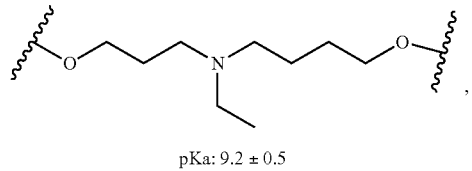
pKa: 9.2 ± 0.5
(13)
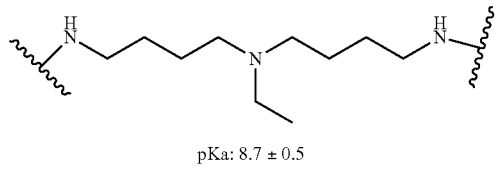
pKa: 8.7 ± 0.5
(14)
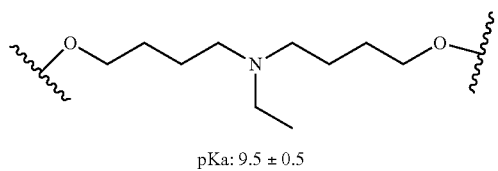
pKa: 9.5 ± 0.5
(15)
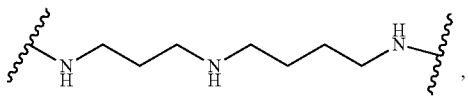
pKa: 8.8 ± 0.2
(16)
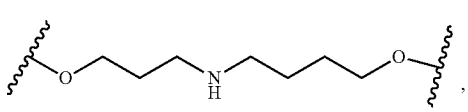
pKa: 10.2 ± 0.2
(17)
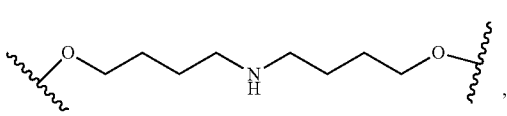
pKa: 10.4 ± 0.2
(18)
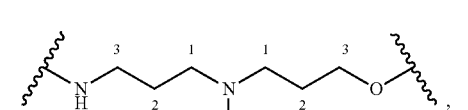
pKa: 7.8 ± 0.5
(19)
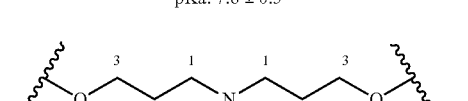
pKa: 8.8 ± 0.5
(20)
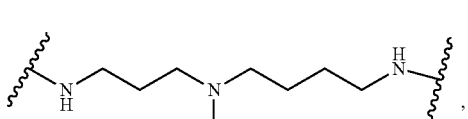
pKa: 7.7 ± 0.5
(21)
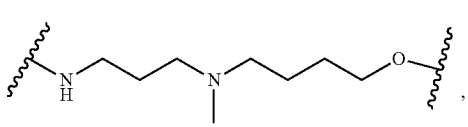
pKa: 8.1 ± 0.5
(22)
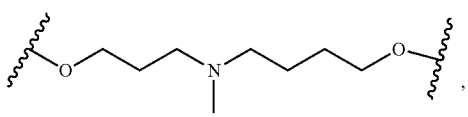
pKa: 10.2 ± 0.2
(23)
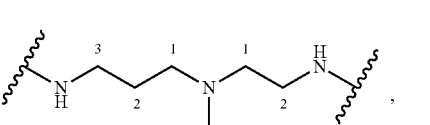
pKa: 5.6 ± 0.5
(24)
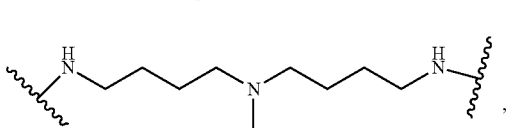
pKa: 8.6 ± 0.5

(25)
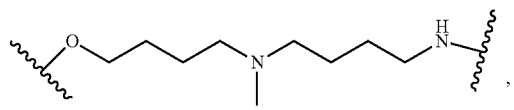
pKa: 9.9 ± 0.1

(26)
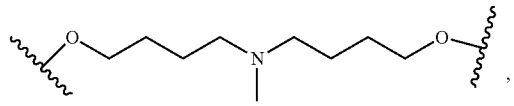
pKa: 9.4 ± 0.5

(27)
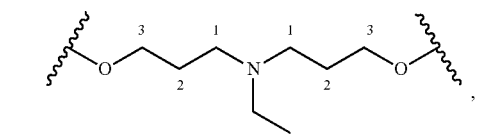
pKa: 8.9 ± 0.5

(28)
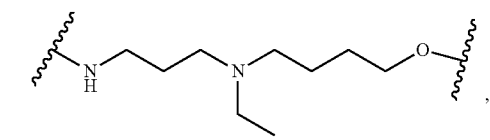
pKa: 8.2 ± 0.5

(29)
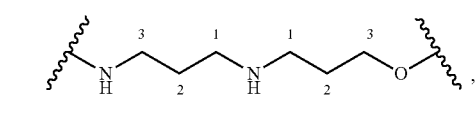
pKa: 8.5 ± 0.2

(30)
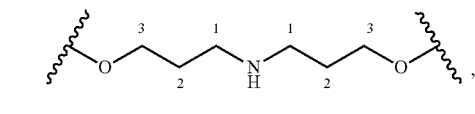
pKa: 10.2 ± 0.2

(31)
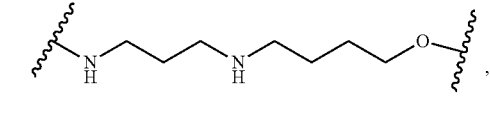
pKa: 8.8 ± 0.1

(32)
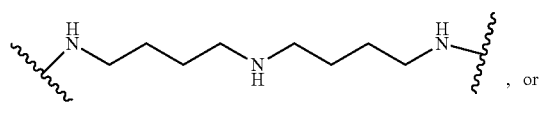
pKa: 9.3 ± 0.2

(33)
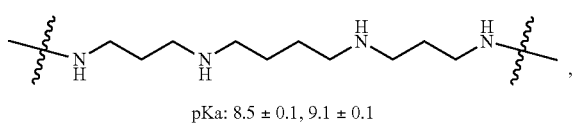
pKa: 8.5 ± 0.1, 9.1 ± 0.1

(34)
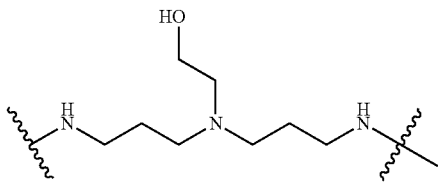
pKa: 9.415, 14.814

(35)
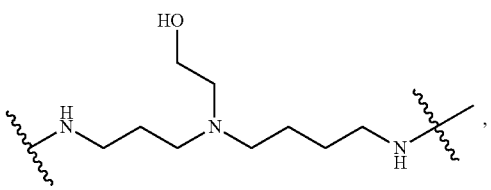
pKa: 9.425, 14.821

(36)
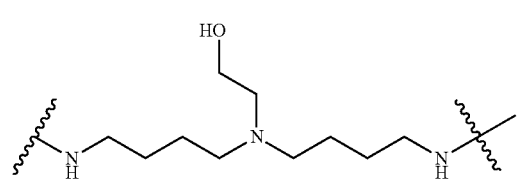
pKa: 9.436, 14.827

The hydrophobic unit B of Formula Ia, Ib, Ic, Id, Ie and If may be a $C_1$-$C_{28}$ alkyl or $C_2$-$C_{28}$ alkenyl group. Each of the $C_1$-$C_{28}$ alkyl or $C_2$-$C_{28}$ alkenyl group may be optionally substituted with one to four substituents selected from halogen, —CN, —$NO_2$, —$N_3$, $C_1$-$C_6$ alkyl, halo($C_1$-$C_6$ alkyl), —OR, —$NR_2$, —$CO_2R$, —OC(O)R, —CON(R)$_2$, —OC(O)N(R)$_2$, —NHC(O)N(R)$_2$, —NHC(NH)N(R)$_2$, $C_3$-$C_8$ cycloalkyl, $C_3$-$C_8$ cycloalkenyl, aryl, heteroaryl, or heterocycle. Each R may independently be selected from hydrogen, $C_1$-$C_6$ alkyl, halo($C_1$-$C_6$ alkyl), $C_3$-$C_8$ cycloalkyl, $C_3$-$C_8$ cycloalkenyl, aryl, heteroaryl, or heterocycle. Each cycloalkyl, cycloalkenyl, aryl, heteroaryl, and heterocycle may be further optionally substituted with R', wherein R' may independently be selected from halogen, —CN, —$NO_2$, —$N_3$, $C_1$-$C_6$ alkyl, or halo($C_1$-$C_6$ alkyl). Embodiments herein include a nucleic acid carrier having one or more of the amine linkers deprotonated. Embodiments herein include a nucleic acid carrier having one or more of the amine linkers protonated. Embodiments herein include a nucleic acid carrier having all the amine linkers deprotonated. Embodiments herein include a nucleic acid carrier having all of the amine linkers protonated.

The hydrophobic unit B of Formula Ia, Ib, Ic, Id, Ie, If, Ig, Ih, Ii, Ij, IIa and IIb may be introduced by contacting the nucleic acid carrier with a functional reagent. In an embodiment, the functional reagent is a fatty acid. The fatty acid may be a saturated or unsaturated fatty acid having C4-C28 chains. The fatty acid may be, but is not limited to, caprylic acid, capric acid, lauric acid, myristic acid, palmitic acid, stearic acid, oleic acid, linoleic acid, linolenic acid, arachidonic acid, eicosapentaenoic acid, 12-hydroxy-9-cis-octadecenoic acid (ricinoleic acid), 12-methyltetradecanoic acid, 12-methyltridecanoic acid, 14-methylhexadecanoic acid, 14-methylhexadecanoic acid, 18-methylnonadecanoic acid, 19-methylarachidic acid, isopalmitic acid, isostearic acid, phytanic acid, (±)-2-hydroxyoctanoic acid, (±)-3-hydroxydecanoic acid, (±)-3-hydroxyoctanoic acid, 10-hydroxydecanoic acid, 12-hydroxyoctadecanoic acid, 15-hydroxypentadecanoic acid, 16-hydroxyhexadecanoic acid, 2-hydroxyhexadecanoic acid, 2-hydroxytetradecanoic acid, 2-hydroxydodecanoic acid, DL-α-hydroxystearic acid, DL-ß-hydroxylauric acid, DL-ß-hydroxymyristic acid, or DL-ß-hydroxypalmitic acid. The fatty acid may be selected from conjugated fatty acids (e.g., conjugated isomers of linoleic acid); acetylenic fatty acids (e.g., crepenynic acid); allenic fatty acids (e.g., laballenic acid) or cyclopropenyl fatty acids (e.g., sterculic acid).

The hydrophobic unit B may be a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, but-3-en-1-yl, oct-7-en-1-yl, 12-tridecenyl, 14-pentadecenyl, 17-octadecenyl, oleyl, linoleyl, arachidoneyl, 16-hydroxyhexadecyl, or 12-hydroxy-9-cis-octadecenyl(ricinoleyl) group.

In an embodiment, the nucleic acid carrier may comprise a tracking moiety. The tracking moiety may be one or more functional groups suitable for tracking the delivery material in vitro and in vivo. The nucleic acid carrier may have the fatty acids containing stable isotopes of carbon (C) and/or hydrogen (H). In an embodiment, the stable isotopes of carbon (C) and/or hydrogen (H) are $^{13}$C or $^{2}$H (also referred to herein as deuterium, D or d). The tracking moiety(ies) in such nucleic acid carrier would be the stable isotope(s) of carbon or hydrogen. When the nucleic acid carrier is formulated into nanoparticles with nucleic acids, the nanoparticles may be tracked in vitro and in vivo post-administration by techniques such as mass spectroscopy or nuclear magnetic resonance imaging. In an embodiment the nucleic acid in the tracked nanoparticle is a replicon RNA. The inclusion of the stable isotopes may be beneficial for identification of the delivery molecules since these isotopes differ from the abundant in tissues $^{12}$C and $^{1}$H isotopes. Tracking may be useful for identifying biodistribution, material clearance and molecular stability of nanoparticles post-administration, and related issues. The isotopically labeled fatty acids may be, but are not limited to, octanoic acid-1-$^{13}$C, octanoic acid-8-$^{13}$C, octanoic acid-8,8,8-$^{2}$H3, octanoic-$^{2}$H15 acid, decanoic acid-1-$^{13}$C, decanoic acid-10-$^{13}$C, decanoic-10,10,10-$^{2}$H3 acid, decanoic-$^{2}$H19 acid, undecanoic acid-1-$^{13}$C, lauric acid-12,12,12-$^{2}$H3, lauric-$^{2}$H23 acid, lauric acid-1-$^{13}$C, lauric acid-1,12-$^{13}$C2, tridecanoic-2,2-$^{2}$H2 acid, myristic acid-14-$^{13}$C, myristic acid-1-$^{13}$C, myristic acid-14,14,14-$^{2}$H3, myristic-d27 acid, palmitic acid-1-$^{13}$C, palmitic acid-16-$^{13}$C, palmitic acid-16-$^{13}$C,16,16,16-$^{2}$H3, palmitic acid-$^{2}$H31, stearic acid-1-$^{13}$C, stearic acid-18-$^{13}$C, stearic acid-18,18,18-$^{2}$H3, stearic-$^{2}$H35 acid, oleic acid-1-$^{13}$C, oleic acid-$^{2}$H34, linolenic acid-1-$^{13}$C, linoleic acid-$^{2}$H32, arachidonic-5,6,8,9,11,12,14,15-$^{2}$H8 acid, or eicosanoic-$^{2}$H39 acid.

The Y of Formula Ia, Formula Ib, Formula Ie, Formula If, Formula Ii, Formula Ij and Formula IIa is a sugar. Non-limiting examples of the sugar are furanose monosaccharide (e.g., xylo-, ribo-, or arabinofuranose), pyranose monosaccharide (e.g., glucose, mannose, galactose), disaccharide (e.g., lactose, trehalose), polysaccharide (e.g., cyclodextrin), or sugar derivatives. In an embodiment, the sugar derivatives are selected from nucleosides or nucleotides, etc. The Z of Formula Ic or Formula Id Formula Ig or Formula Ih or Formula IIb is a deoxy sugar. Deoxy sugars are sugars that have had a hydroxyl group replaced with a hydrogen atom, where non-limiting examples of the sugar are furanose monosaccharide, pyranose monosaccharide, disaccharide, oligosaccharide, polysaccharide, or sugar derivatives. In an embodiment, the sugar derivatives are selected from nucleosides or nucleotides. Non-limiting examples of the deoxy sugar are 2-deoxy-D-ribose, a constituent of DNA, 6-deoxy-L-tagatose, 5-deoxy-xylo-, ribo-, and arabinofuranoses, 1-deoxy glucose, 2-deoxy glucose, 6-deoxy glucose, 1-deoxy mannose, 2-deoxy galactose, 6-deoxy galactose, 1-deoxy lactose, 6-deoxy-trehalose, 6-deoxy-2,4-diacetamido-2,4,6-trideoxy-D-mannose, and 6A-deoxy-ß-cyclodextrin.

The Z of Formula Ic or Formula Id or Formula IIb may be introduced by contacting the nucleic acid carrier with a functional reagent by click chemistry. In an embodiment, the functional reagent is selected from deoxy-sugar (monosaccharide, disaccharide, or polysaccharide) azides. The azide may be, but is not limited to, D-Xylopyranosyl azide, 2,3,4-Tri-O-acetyl-ß-D-xylopyranosyl azide, 2,3,4,6-Tetra-O-acetyl-α-D-mannopyranosyl azide, 3,4,6-Tri-O-acetyl-2-O-trifluoromethanesulfonyl-ß-D-mannopyranosyl azide, 1,3,4,6-Tetra-O-acetyl-2-azido-2-deoxy-D-galactopyranose, 1,2,3,4-Tetra-O-acetyl-6-azido-6-deoxy-α-D-galactopyranose, 2,3,4,6-Tetra-O-acetyl-ß-D-galactopyranosyl azide, 2,3,4-Tri-O-acetyl-6-azido-6-deoxy-ß-D-glucopyranosylamine, 2,3,4-Tri-O-acetyl-6-azido-6-deoxy-ß-D-glucopyranosyl azide, 2,3,4,6-Tetra-O-acetyl-ß-D-glucopyranosyl azide, 6-O-Tosyl-ß-D-glucopyranosyl azide, 1,3,4,6-Tetra-O-acetyl-2-azido-2-deoxy-D-glucopyranose, 1,3,4-Tri-O-acetyl-2-azido-2-deoxy-6-O-trityl-ß-D-glucopyranose, 2,3,4-Tri-O-acetyl-6-O-tosyl-ß-D-glucopyranosyl azide, 3,4,6-Tri-O-acetyl-2-azido-2-deoxy-ß-D-glucopyranosyl trichloroacetimidate, 3,4,6-Tri-O-acetyl-2-azido-2-deoxy-D-glucopyranosyl trichloroacetimidate, 1,2,4,6-Tetra-O-acetyl-3-azido-3-deoxy-D-glucopyranose, 1,3,4-Tri-O-acetyl-2-azido-2-deoxy-ß-D-glucopyranuronic acid methyl ester, 3,4,6-Tri-O-acetyl-2-deoxy-2-fluoro-ß-D-glucopyranosyl azide, 1,3,4-Tri-O-acetyl-2-azido-2-deoxy-α-L-fucopyranose, 1,2,3,4-Tetra-O-acetyl-6-azido-L-fucopyranose, 1,2,3,4-Tetra-O-acetyl-6-azido-6-deoxy-D-galactopyranose, Ethyl 3-azido-3-deoxy-N-methyl-ß-D-glucopyranosiduronamide, Ethyl 3-azido-3-deoxy-2,4-di-O-acetyl-ß-D-glucopyranuronic acid benzyl ester, Ethyl 3-azido-3-deoxy-ß-D-glucopyranuronic acid methyl ester, ß-L-Fucopyranosyl azide, 2-Fluoro-4-nitrophenyl 2-azido-2-deoxy-ß-D-galactopyranoside, ß-D-Galactopyranosyl azide, ß-D-Maltosyl azide heptaacetate, ß-D-Lactosyl azide, ß-D-Lactosyl azide heptaacetate, Methyl 4-azido-4-deoxy-ß-D-glucopyranoside, Methyl 4-azido-2,3,6-tri-O-benzoyl-4-deoxy-ß-D-glucopyranoside, Methyl 2,3,4-tri-O-acetyl-6-azido-6-deoxy-α-D-glucopyranoside, Methyl 2,3,4-tri-O-acetyl-ß-D-glucopyranuronosyl azide, ß-D-Maltosyl azide, α-D-Mannopyranosyl azide, Phenyl 2-azido-2,6-dideoxy-1-seleno-α-D-galactopyranoside, Phenyl 3,4,6-tri-O-acetyl-2-azido-2-deoxy-1-seleno-α-D-galactopyranoside, Phenyl 2-azido-2-deoxy-1-seleno-α-D-galactopyranoside, Phenyl 3,6-di-O-acetyl-2-azido-2-deoxy-1-seleno-α-D-galactopyranoside, 2,3,4-Tri-O-acetyl-ß-L-fucopyranosyl azide, 2-Acetamido-2-deoxy-ß-D-glucopyranosyl azide, 2-Acetamido-3,4,6-tri-O-acetyl-2-deoxy-ß-D-glucopyranosyl azide, ß-D-Glucopyranosyl azide, 6-Azido-6-deoxy-ß-D-glucopyranosylamine, 1-O-Acetyl-4-azido-2,3,6-tri-O-benzoyl-4-deoxy-D-glucopyranose, 2-Azido-2-deoxy-D-galactose, 3-Azido-3-deoxy-D-galactose, 4-Azido-4-deoxy-D-galactose, 3-Azido-3-deoxy-4-hydroxymethyl-1,2-O-isopropylidene-α-D-ribofuranose, 6-Azido-6-deoxy-2,3-O-isopropylidene-α-L-sorbofuranose, ß-D-Cellobiosyl azide, ß-D-Cellobiosyl azide heptaacetate, 2-Chloro-4-nitrophenyl 2-azido-2-deoxy-ß-D-galactopyranoside, 3,4-Di-O-acetyl-1,6-anhydro-2-azido-2-deoxy-ß-D-glucopyranose, 6,6'-Diazido-6,6'-dideoxy-α,α-D-trehalose, 3,6-Di-O-acetyl-2-azido-2-deoxy-α-D-glucopyranose, 2-Deoxy-2-fluoro-ß-D-glucopyranosyl azide, 1,6-Di-O-acetyl-2-azido-3,4-di-O-benzyl-2-deoxy-α-D-glucopyranose, 3,4-Di-O-acetyl-2-azido-2-deoxy-D-glucopyranose, 6,6'-Diazido-6,6'-dideoxy-α,α-D-trehalose hexaacetate, 3-Azido-3-deoxy-1,2:5,6-di-O-isopropylidene-α-D-allofuranose, 3-Azido-3-deoxy-1,2-O-isopropylidene-α-D-allofuranose, 4-O-(6-Azido-6-deoxy-ß-D-glucopyranosyl)-D-glucose, 2-Azido-2-deoxy-L-fucopyranose, 6-Azido-L-fucose, 6-Azido-6-deoxy-D-galactose, 2-Azido-2-deoxy-1-O-(thexyldimethylsilyl)-ß-L-fucopyranose, 2-Azido-2-deoxy-D-glucofuranurono-6,3-lactone, 6-Azido-6-deoxy-1,2-O-isopropylidene-α-D-glucofuranose, 4-Azido-4-deoxy-D-glucose, 6-Azido-6-deoxy-D-glucopyranose, 1,6-Anhydro-2-azido-3-O-benzyl-2-deoxy-ß-D-glucopyranose, 1,6-Anhydro-2-azido-4-O-benzyl-2-deoxy-ß-D-glucopyranose, 1,6-Anhydro-2-azido-3,4-di-O-benzyl-2-deoxy-ß-D-glucopyranose, 1,6-Anhydro-2-azido-2-deoxy-ß-D-glucopyranose, 2-Azido-2-deoxy-D-glucose, 6-O-Acetyl-2-azido-3,4-di-O-benzyl-2-deoxy-D-glucopyranose, 3-Azido-3-deoxy-1,2:5,6-di-O-isopropylidene-α-D-glucofuranose, 3-Azido-3-deoxy-D-glucopyranose, The Y of Formula Ii or Formula Ij may be introduced by contacting the nucleic acid carrier with a functional reagent by thiol chemistry. In an embodiment, the functional reagent is selected from sugar (monosaccharide, disaccharide, or polysaccharide)thiols. The sugar thiol may be, but is not limited to ß-D-GlcNAc-Ethyl-Thiol, ß-LacNAc-PEG3-Thiol, ß-Lac-PEG3-Thiol, α-Man-PEG3-Thiol, ß-Glc-PEG3-Thiol, ß-GlcNAc-PEG3-Thiol, ß-Gal-PEG3-Thiol, α-GalNAc-PEG3-Thiol, ß-GalNAc-PEG3-Thiol, ß-Gal-PEG3-Thiol, ß-GlcNAc-PEG3-Thiol, α-Man-PEG3-Thiol, ß-Glc-PEG3-Thiol, ß-Lac-PEG3-Thiol, ß-LacNAc-PEG3-Thiol and NeuAcα(2-6)LacNAc-PEG3-Thiol.

The Z of Formula Ig or Formula Ih may be introduced by contacting the nucleic acid carrier with a functional reagent by disulfide chemistry. In an embodiment, the functional reagent is selected from deoxy-sugar (monosaccharide, disaccharide, or polysaccharide)thiols. The sugar thiol may be, but is not limited to 1-thio-ß-D-glucopyranose, 2-acetamido-2-deoxy-1-thio-ß-D-glucopyranose, 1-thio-ß-D-lactopyranose, C-glucosylpropyl thiol and C-mannosyl thiol.

An embodiment comprises a nanoparticle composition comprising any one or more of the nucleic acid carriers described herein. The nanoparticle composition may further comprise an agent; for example, a nucleic acid. A nanoparticle composition herein may be useful to introduce an agent into a cell. The agent may be a nucleic acid. A nanoparticle composition herein may be useful as a transfection agent. A nanoparticle composition herein may be useful in a method of treating or preventing a disease.

In an embodiment, a nanoparticle composition may comprise a mixture of nucleic acid carriers, each one of them comprising different amine and/or side chains and/or sugar. These nucleic acid carriers may be mixed at a fixed ratio. For an example of mixture with three nucleic acid carriers, a ratio of the first nucleic acid carrier to the second nucleic acid carrier and to the third nucleic acid carrier may be i:j:k where i, j and k are independently selected from 1, 2, 3, 4, 5, 6, 7, 8, 9, 10, 11, 12, 13, 14, 15, 16, 17, 18, 19, or 20, or a value between any two of the foregoing.

In an embodiment, the nanoparticle composition may comprise one or more nucleic acid agents. The nucleic agents may be therapeutic or immunogenic. As used herein, the term "nucleic acid" refers to any natural or synthetic DNA or RNA molecules. An agent; e.g., a therapeutic or immunogenic nucleic acid agent, of a composition herein may be complexed with or encapsulated in a nucleic acid carrier of the nanoparticle composition.

In an embodiment, the nucleic acid agent may be an RNA or DNA molecule. The nucleic acid agent may also be a mixture of one or more different RNA molecules, DNA molecules, or combination of the two. The term "DNA" or "DNA molecule" or "deoxyribonucleic acid molecule" refers to a polymer of deoxyribonucleotides. The DNA molecule may be a polynucleotide, oligonucleotide, DNA, or cDNA. The DNA molecule may encode wild-type or engineered proteins, peptides or polypeptides. The encoded protein, peptide, or polypeptice may be an antigen. The term "RNA" or "RNA molecule" or "ribonucleic acid molecule" refers to a polymer of ribonucleotides. The polymer may have 2, 3, 4, 5, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000 or more ribonucleotides. The polymer may have 2, 3, 4, 5, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, or 50000 ribonucleotides, or a number of ribonucleotides in a range between any two of the foregoing. The RNA molecule may be a replicon RNA (repRNA), small interfering RNA (siRNA), miRNA, single strand guide RNA (sgRNA), messenger RNA (mRNA), or transfer RNA (tRNA). Replicon RNA (repRNA) refers to a genome replication-competent, progeny-defective RNA virus genome that is incapable of producing infectious progeny virions. Viral genomes that are typically modified for use as repRNAs include "positive strand" RNA viruses. The modified viral genomes function as both mRNA and templates for replication. Small interfering RNA (siRNA) refers to an RNA (or RNA analog) comprising between about 10-50 nucleotides (or nucleotide analogs) which is capable of directing or mediating RNA interference. MicroRNAs (miRNAs) refers to small (20-24 nt) regulatory non-coding RNAs that are involved in post-transcriptional regulation of gene expression in eukaryotes by affecting either or both the stability and translation of coding mRNAs. Messenger RNAs (mRNAs) are usually single-stranded RNAs and define the amino acid sequence of one or more polypeptide chains. This information is translated during protein synthesis when ribosomes bind to the mRNA. The DNA or RNA molecules may be chemically modified in nucleic acid backbone, the ribose sugar moiety and the nucleobase itself.

The RNA molecule may be a monocistronic or polycistronic mRNA. A monocistronic mRNA refers to an mRNA comprising only one sequence encoding a protein, polypeptide or peptide. A polycistronic mRNA typically refers to two or more sequences encoding two or more proteins, polypeptides or peptides. An mRNA may encode a protein, polypeptide, or peptide that acts as an antigen.

In an embodiment, the DNA molecule may be a polynucleotide, oligonucleotide, DNA, or cDNA. The RNA molecule may be a replicon RNA (repRNA), small interfering RNA (siRNA), miRNA, single strand guide RNA (sgRNA), messenger RNA (mRNA), or transfer RNA (tRNA). The therapeutic or immunogenic nucleic acid agent may be non-covalently bound or covalently bound to the nucleic acid carrier. The therapeutic or immunogenic agent may be a nucleic acid agent bound to the charged nucleic acid carrier through electrostatic interaction. The nucleic acid agent may be bound to the charged nucleic acid carrier through electrostatic interaction and Hydrogen bonding.

In an embodiment, the nanoparticle compositions described herein may include immunogenic or therapeutic nucleic acid agents encoding antigens.

As used herein, "encapsulated" can refer to a nanoparticle that provides an active agent or therapeutic agent with full encapsulation, partial encapsulation, or both. In an embodiment, the therapeutic agent is a nucleic acid (as a non-limiting example, a messenger RNA), In a preferred embodiment, the nucleic acid is fully encapsulated in the nanoparticle. In the context of nucleic acid therapeutic agents, full encapsulation may be determined by a Ribogreen® assay. RiboGreen® is an ultra-sensitive fluorescent nucleic acid stain for quantitating oligonucleotides and single-stranded DNA or RNA in solution (available from Thermo Fisher Scientific—U.S.).

"Antigen" as used herein is defined as a molecule that triggers an immune response. The immune response may involve either antibody production, or the activation of specific immunologically active cells, or both. The antigen may refer to any molecule capable of stimulating an immune response, including macromolecules. In an embodiment, the macromolecules are proteins, peptides, or polypeptides. The antigen may be a structural component of a pathogen, or a cancer cell or a derivative thereof. The antigen may be synthesized, produced recombinantly in a host, or may be derived from a biological sample, including but not limited to a tissue sample, cell, or a biological fluid.

The antigen may be but is not limited to a vaccine antigen, parasite antigen, bacterial antigen, tumor antigen, environmental antigen, therapeutic antigen or an allergen. As used herein a nucleotide vaccine is a DNA- or RNA-based prophylactic or therapeutic composition capable of stimulating an adaptive immune response in the body of a subject by delivering antigen(s). The immune response induced by vaccination typically results in development of immunological memory, and the ability of the organism to quickly respond to subsequent encounter with the antigen or infectious agent.

The use of a "nucleic acid carrier" herein as a carrier of nucleic acids is preferred and the name "nucleic acid carrier" is applied for that reason. However, a non-nucleic acid agent may be in an embodiment herein.

In an embodiment, the nanoparticle composition described herein may comprise a lipid conjugate. In an embodiment, the lipid conjugate may be useful in that it may prevent the aggregation of particles. Lipid conjugates that may be in a composition herein include, but are not limited to, poly ethylene glycol (PEG)-lipid conjugates. Non-limiting examples of PEG-lipids include PEG coupled to lipids (for example, DMG-PEG 2000), PEG coupled to phospholipids (for example, phosphatidylethanolamine (PEG-PE)), PEG conjugated to cholesterol or a derivative thereof, and mixtures thereof. In certain instances, the PEG may be optionally substituted by an alkyl, alkoxy, acyl, or aryl group.

PEGs are classified by their molecular weights; for example, PEG 2000 has an average molecular weight of about 2,000 daltons, and PEG 5000 has an average molecular weight of about 5,000 daltons. PEGs are commercially available from Avanti Polar Lipids. The PEG moiety of the PEG-lipid conjugates described herein may comprise an average molecular weight ranging from 550 daltons to 10,000 daltons.

Phosphatidylethanolamines having a variety of acyl chain groups of varying chain lengths and degrees of saturation can be conjugated to PEG to form the lipid conjugate. Phosphatidylethanolamines are commercially available, or can be isolated or synthesized using conventional techniques. The phosphatidylethanolamines may comprise saturated or unsaturated fatty acids with carbon chain lengths in the range of $C_{10}$ to $C_{20}$. The phosphatidylethanolamines may comprise mono- or polyunsaturated fatty acids and mixtures of saturated and unsaturated fatty acids. The phosphatidylethanolamines contemplated include, but are not limited to, dimyristoylphosphatidylethanolamine (DMPE), dipalmitoyl-phosphatidylethanol amine (DPPE), dioleoylphosphatidylethanolamine (DOPE), and distearoyl-phosphatidylethanolamine (DSPE).

The PEG-lipid may comprise PEG conjugated to cholesterol or cholesterol derivative. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof.

The size, relative quantity, and distribution of the PEG-lipid included in the nanoparticle composition may affect physical properties of the nanoparticle composition, and can be used to control particle properties. The properties that can be controlled may be, but are not limited to, diameter of the nanoparticle, the propensity of the nanoparticles to aggregate, the number of nucleic acid molecules inside each nanoparticle, or the concentration of the nanoparticles in the nanoparticle composition, the efficacy of the intra-cellular delivery of therapeutic and immunogenic nucleic acid agents, and/or the efficacy of uptake of the nanoparticles by cells. See PCT/US19/67402 (Poulami Talukder, Jasdave S. Chahal, Justine S. McPartlan, Omar Khan, Karl Ruping. Nanoparticle Compositions for Efficient Nucleic Acid Delivery and Methods of Making and Using the Same) and Reichmuth, A. M. et al. "mRNA vaccine delivery using lipid nanoparticles." Therapeutic Delivery 7,5 (2016): 319-34, both of which are incorporated herein by reference as if fully set forth.

The nanoparticle composition may contain 10 mol % or less of the PEG-lipid per nanoparticle composition. The nanoparticle composition may comprise about 10 mol %, about 9 mol %, about 8 mol %, about 7 mol %, about 6 mol %, about 5 mol %, about 4 mol %, about 3 mol %, about 2 mol %, or about 1 mol %, or any amount in between any two of the foregoing integers of the PEG-lipid per nanoparticle composition. The nanoparticle composition comprising the PEG-lipid may comprise nanoparticles with a smaller diameter than nanoparticles of the composition lacking the PEG-lipid.

The nanoparticle composition may contain "amphipathic lipid". As used herein, "amphipathic lipid" refers to any material having non-polar hydrophobic units or "tails", and polar "heads." Polar groups may include, but are not limited to, phosphate, carboxylic, sulfato, amino, sulfhydryl, nitro, and hydroxyl. Nonpolar groups may include, but are not limited to, long-chain saturated and unsaturated aliphatic hydrocarbon groups and such groups substituted by one or more cycloalkyl, cycloalkenyl, aryl, heteroaryl, or heterocycle group(s). Examples of amphipathic lipids include, but are not limited to, phospholipids, aminolipids, and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine. Representative examples of the phosphatidylcholine include, but are not limited to, dipalmitoylphosphatidyl choline, dioleoylphos-phatidylcholine, distearoylphosphatidylcholine, and dilinoleoylphosphatidylcholine. Representative examples of the phosphatidylethanolamine include, but are not limited to, 1,2-dioleoyl-sn-glycero-3-phosphoethanolamine or DOPE.

The nanoparticle composition may contain the amphipathic lipid in the amount ranging from 10 mol % to 15 mol % per nanoparticle composition. The amphipathic mol % may be 10, 11, 12, 13, 14, or 15 mol % or a value in a range between any two of the foregoing.

In an embodiment, the nanoparticle composition may include cholesterol or cholesterol derivative. Examples of cholesterol derivatives include, but are not limited to, cholestanol, 5,6-epoxy cholestanol, cholestanone, cholestenone, coprostanol, cholesteryl-2'-hydroxyethyl ether, cholesteryl-4'-hydroxybutyl ether, 24-ethyl cholesterol, 24-methyl cholesterol, cholenic Acid, 3-hydroxy-5-cholestenoic Acid, cholesteryl palmitate, cholesteryl arachidonate, cholesteryl arachidate, cholesteryl myristate, cholesteryl palmitoleate, cholesteryl lignocerate, cholesteryl oleate, cholesteryl stearate, cholesteryl erucate, cholesterol α-linolenate, cholesteryl linoleate, cholesteryl homo-γ-linolenate, 4-hydroxy cholesterol, 6-hydroxy cholesterol, 7-hydroxy cholesterol, 19-hydroxy cholesterol, 20-hydroxy cholesterol, 22-hydroxy cholesterol, 24-hydroxy cholesterol, 25-hydroxy cholesterol, 27-hydroxy cholesterol, 27-alkyne cholesterol, 7-keto cholesterol, 7-dehydro cholesterol, 8-dehydro cholesterol, 24-dehydro cholesterol, 5α-hydroxy-6-keto cholesterol, 20,22-dihydroxy cholesterol, 7,25-dihydroxy cholesterol, 7,27-dihydroxy cholesterol, 7-keto-25-hydroxy cholesterol, fucosterol, phytosterol, cholesteryl 11,14-eicosadienoate, dimethyl hydroxyethyl aminopropane carbamoyl cholesterol iodide and mixtures thereof. The cholesterol derivative may comprise a sugar moiety and/or amino acids. In an embodiment the amino acids are selected from serine, threonine, lysine, histidine, arginine or their derivatives. The nanoparticle composition may include the cholesterol or cholesterol derivative in an amount ranging from 50 mol % to 75 mol % per nanoparticle composition. The cholesterol or cholesterol derivative mol % may be 50, 51, 52, 53, 54, 55, 56, 57, 58, 59, 60, 61, 62, 63, 64, 65, 66, 67, 68, 69, 70, 71, 72, 73, 74, or 75 mol % or a value in a range between any two of the foregoing.

In an embodiment, a nanoparticle composition; e.g., a pharmaceutical composition herein, may be sterilized by conventional, well-known sterilization techniques. Aqueous solutions may be packaged for use or lyophilized. The lyophilized preparation may be combined with a sterile aqueous solution prior to administration. In an embodiment, a nanoparticle composition may include a pharmaceutically acceptable carrier. As used herein, the term "pharmaceutically-acceptable carrier" means a pharmaceutically acceptable material, composition or vehicle, for example a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier is "pharmaceutically-acceptable" in the sense of being compatible with the other ingredients of the formulation and not injurious to the subject. Some examples of materials which may serve as pharmaceutically-acceptable carriers include: (1) sugars, for example lactose, glucose, mannose and/or sucrose; (2) starches, for example corn starch and/or potato starch; (3) cellulose, and its derivatives, for example sodium carboxymethyl cellulose, methylcellulose, ethyl cellulose, microcrystalline cellulose and/or cellulose acetate; (4) powdered tragacanth; (5) malt; (6) gelatin; (7) lubricating agents, for example magnesium stearate, sodium lauryl sulfate and/or talc; (S) excipients, for example cocoa butter and/or suppository waxes; (9) oils, for example peanut oil, cottonseed oil, safflower oil, sesame oil, olive oil, corn oil and/or soybean oil; (10) glycols, for example propylene glycol; (11) polyols, for example glycerin, sorbitol, and/or mannitol; (12) esters, for example glycerides, ethyl oleate and/or ethyl laurate; (13) agar; (14) buffering agents, for example magnesium hydroxide and/or aluminum hydroxide; (15) alginic acid; (16) pyrogen-free water; (17) diluents, for example isotonic saline, and/or PEG400; (I8) Ringer's solution; (19) C2-C12 alcohols, for example ethanol; (20) fatty acids; (21) pH buffered solutions; (22) bulking agents, for example polypeptides and/or amino acids (23) serum component, for example serum albumin, HDL and LDL; (24) surfactants, for example polysorbates (Tween 80) and/or poloxamers; and/or (25) other non-toxic compatible substances employed in pharmaceutical formulations: for example, fillers, binders, wetting agents, coloring agents, release agents, coating agents, sweetening agents, flavoring agents, perfuming agents, preservatives and/or antioxidants. The terms "excipient," "pharmaceutically acceptable carrier." or the like are used interchangeably herein.

An embodiment comprises a method for treating or preventing a disease or condition in a subject. The method may comprise providing any one of the nanoparticle compositions or pharmaceutical compositions described herein. The method may comprise administering a therapeutically effective amount of the nanoparticle composition to a subject.

As used herein, the term "therapeutically effective amount" refers to the amount of nanoparticle composition which is effective for producing a desired therapeutic effect. The therapeutic effect may be achieved at a reasonable benefit/risk ratio applicable to medical treatment. A "therapeutically effective amount" may refer to an amount sufficient to generate appearance of antigen-specific antibodies in serum. A "therapeutically effective amount" may refer to an amount sufficient to cause a decrease in disease symptoms. A "therapeutically effective amount" may refer to an amount sufficient to cause a disappearance of disease symptoms. When treating viral infection, a decrease of disease symptoms may be assessed by decrease of virus in faeces, in bodily fluids, or in secreted products. The nanoparticle compositions may be administered using an amount and by a route of administration effective for generating an immune response.

Therapeutic efficacy may depend on effective amounts of active agents and time of administration necessary to achieve a desired result. Administering a nanoparticle composition may be a preventive measure. Administering of a nanoparticle composition may be a therapeutic measure to promote immunity to the infectious agent, to minimize complications associated with the slow development of immunity especially in patients with a weak immune system, the elderly, or infants.

The exact dosage may be chosen by the clinician based on a variety of factors and in view of individual patients. Dosage and administration may be adjusted to provide sufficient levels of the active agent or agents or to maintain the desired effect. For example, factors which may be taken into account may include the type and severity of a disease; age and gender of the patient; drug combinations; and an individual response to therapy.

Therapeutic efficacy and toxicity of active pharmaceutical agents in a nanoparticle composition may be determined by standard pharmaceutical procedures, for example, by determining the therapeutically effective dose in 50% of the population (ED50) and the lethal dose to 50% of the population (LD50) in cells cultured in vitro or experimental animals. Nanoparticle compositions may be evaluated based on the dose ratio of toxic to therapeutic effects (LD50/ED50), called the therapeutic index, the large value of which may be used for assessment. The data obtained from cell and animal studies may be used in formulating a dosage for human use.

The therapeutically effective dose may be estimated initially from cell culture assays. A therapeutically effective dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage may be monitored by a suitable bioassay.

The amount of particles administered will depend upon the particular therapeutic agent (e.g., nucleic acid) used, the disease or disorder being treated, the age, weight, and condition of the patient, and the judgment of the clinician. A therapeutically effective dose may be between 0.001 ng and 50 mg of the therapeutic or immunogenic nucleic acid per kilogram of body weight of the subject. A therapeutically effective dose may be 0.001 ng, 0.002 ng, 0.003 ng, 0.004 ng, 0.005 ng, 0.006 ng, 0.007 ng, 0.008 ng, 0.009 ng, 0.01 ng, 0.02 ng, 0.03 ng, 0.04 ng, 0.05 ng, 0.06 ng, 0.07 ng, 0.08 ng, 0.09 ng, 0.1 ng, 0.2 ng, 0.3 ng, 0.4 ng, 0.5 ng, 0.6 ng, 0.7 ng, 0.8 ng, 0.9 ng, 0.001 µg, 0.002 µg, 0.003 µg, 0.004 µg, 0.005 µg, 0.006 µg, 0.007 µg, 0.008 µg, 0.009 µg, 0.01 µg, 0.02 µg, 0.03 µg, 0.04 µg, 0.05 µg, 0.06 µg, 0.07 µg, 0.08 µg, 0.09 µg, 0.1 µg, 0.2 µg, 0.3 µg, 0.4 µg, 0.5 µg, 0.6 µg, 0.7 µg, 0.8 µg, 0.9 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg of the therapeutic or immunogenic nucleic acid per kilogram of body weight of the subject, or a value in a range between any two of the foregoing. The therapeutic and immunogenic nucleic acid may be a combination of different nucleic acids used per treatment dose. The terms "subject" means a human or animal. Preferably, the animal is a vertebrate. In an embodiment, the vertebrate is selected from a primate, a rodent, a domestic animal or a game animal. Primates include chimpanzees, cynomolgus monkeys, spider monkeys, and macaques, e.g., Rhesus. The rodent may be selected from mice, rats, guinea pigs, woodchucks, ferrets, rabbits and hamsters. The domestic or game animals may be selected from cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. A patient or subject may be selected from the foregoing or a subset of the foregoing. A patient or subject may be selected from all of the above, but excluding one or more groups or species such as humans, primates or rodents. In an embodiment, the patient or subject may be a mammal, e.g., a primate, e.g., a human. The terms, "patient" and "subject" are used interchangeably herein. Preferably, the subject is a mammal. The mammal may be a human, non-human primate, mouse, rat, dog, cat, horse, cow, or swine but is not limited to these examples. Mammals other than humans may be subjects that represent animal models of a disease or disorder. In addition, the methods described herein may be directed to treating domesticated animals and/or pets. A subject may be male or female.

As used herein, the terms "administer," "administering," "administration," or the like refer to the placement of a composition into a subject. The administration may be by a method or route which results in at least partial localization of the composition at a desired site. Placement at a desired site may lead to a production of a desired effect. A nanoparticle composition described herein may be administered by any appropriate route known in the art including, but not limited to, oral or parenteral routes, including intravenous, intramuscular, subcutaneous, transdermal, airway (aerosol), pulmonary, nasal, rectal, or topical (including buccal and sublingual) administration.

Exemplary modes of administration include, but are not limited to, injection, infusion, instillation, inhalation, or ingestion. "Injection" includes without limitation, intravenous, intramuscular, intraarterial, intrathecal, intraventricular, intracapsular, intraorbital, intracardiac, intradermal, intraperitoneal, trans tracheal, subcutaneous, subcuticular, intraarticular, sub capsular, subarachnoid, intraspinal, intracerebral, and intrasternal injection and infusion. In an embodiment, the compositions may be administered by intravenous infusion or injection.

The nanoparticle compositions may be used for delivery of therapeutic or immunogenic nucleic acids for gene targeting, gene silencing, or otherwise modulating gene expression. The therapeutic or immunogenic nucleic acid may be an antisense oligonucleotide (AON) or a double-stranded small interfering RNA (siRNA). Typically, siRNAs are between 21 and 23 nucleotides in length. The siRNAs may comprise a sequence complementary to a sequence contained in an mRNA transcript of a target gene when expressed within the host cell. The antisense oligonucleotide may be a morpholino antisense oligonucleotide. The antisense oligonucleotide may include a sequence complementary to a sequence contained in an mRNA transcript of a target gene. The therapeutic or immunogenic nucleic acid may be an interfering RNA (iRNA) against a specific target gene within a specific target organism. The iRNA may induce sequence-specific silencing of the expression or translation of the target polynucleotide, thereby down-regulating or preventing gene expression. The iRNA may completely inhibit expression of the target gene. The iRNA may reduce the level of expression of the target gene compared to that of an untreated control. The therapeutic or immunogenic nucleic acid may be a microRNA (miRNA). The miRNA may be a short RNA, e.g., a hairpin RNA (hpRNA). The miRNA may be cleaved into biologically active dsRNA within the target cell by the activity of the endogenous cellular enzymes. The RNA may be a double stranded RNA (dsRNA). The ds RNA may be at least 25 nucleotides in length or may be longer. The dsRNA may contain a sequence that is complementary to the sequence of the target gene or genes. An embodiment comprises use of a nanoparticle composition for gene targeting in a subject. An embodiment comprises a method of gene targeting comprising administering a nanoparticle composition herein to a subject.

In an embodiment, the therapeutic or immunogenic nucleic acid may be or may encode an agent that totally or partially reduces, inhibits, interferes with, or modulates the activity or synthesis of, one or more genes encoding target proteins. The target genes may be any genes included in the genome of a host organism. The sequence of the therapeutic or immunogenic nucleic acid may not be 100% complementary to the nucleic acid sequence of the target gene.

In an embodiment, the nanoparticle composition may be used for targeted, specific alteration of the genetic information in a subject. An embodiment comprises targeted, specific alteration of the genetic information in a subject comprising administration of a nanoparticle composition herein. As used herein, the term "alteration" refers to any change in the genome in the cells of a subject. The alteration may be insertion or deletion of nucleotides in the sequence of a target gene. "Insertion" refers to addition of one or more nucleotides to a sequence of a target gene. The term "deletion" refers to a loss or removal of one or more nucleotides in the sequence of a target gene. The alteration may be correction of the sequence of a target gene. "Correction" refers to alteration of one or more nucleotides in the sequence of a target gene, e.g., by insertion, deletion or substitution, which may result in a more favorable expression of the gene manifested by improvements in genotype and/or phenotype of the host organism. An embodiment comprises use of a nanoparticle composition herein for targeted, specific alteration of the genetic information in a subject. An embodiment comprises a method of targeted, specific alteration of the genetic information in a subject comprising administering a nanoparticle composition herein to the subject. An embodiment comprises use of a nanoparticle composition herein for the alteration of the genetic information in the cells of a subject ex vivo by administration of the nanoparticle composition directly to the solution in which the subject's cells are cultured or suspended.

The alteration of the genetic information may be achieved via genome editing techniques. As used herein, "genome editing" refers to the process of modifying the nucleotide sequence in the genome in a precise or controlled manner.

An exemplary genome editing system is a Clustered Regularly Interspaced Short Palindromic Repeats (CRISPR) system as described, for example, in WO 2018/154387, which published Aug. 30, 2018 and is incorporated herein by reference as if fully set forth. In general, "CRISPR system" refers to transcripts and other elements involved in the expression and activity of CRISPR-associated (Cas) genes, including sequences encoding a Cas protein, a tracr (trans-activating CRISPR) sequence, a tracr mate sequence, a guide sequence, or other sequences and transcripts associated with gene editing or regulation by CRISPR-related methods. One or more tracr mate sequences may be operably linked to a guide sequence before processing or crRNA after processing by a nuclease. The tracrRNA and crRNA may be linked and may form a chimeric crRNA-tracrRNA hybrid where a mature crRNA is fused to a partial tracrRNA via a synthetic stem loop to mimic the natural crRNA:tracrRNA duplex as described in Cong et al., Science, 15:339(6121): 819-823 (2013) and Jinek et al., Science, 337(6096):816-21 (2012), which are incorporated herein by reference as if fully set forth. A single fused crRNA-tracrRNA construct is also referred herein as a guide RNA or gRNA, or single-guide RNA (sgRNA). Within an sgRNA, the crRNA portion is identified as the "target sequence" and the tracrRNA is often referred to as the "scaffold." In an embodiment, the nanoparticle compositions described herein may be used to deliver an sgRNA.

In an embodiment, the nanoparticle compositions may be used to apply other exemplary genome editing systems including meganucleases, homing endonucleases, TALEN-based systems, or Zinc Finger Nucleases. The nanoparticle compositions may be used to deliver the nucleic acid (RNA and/or DNA) that encodes the sequences for these gene editing tools, and any gene products, proteins, or other molecules associated with their function.

An embodiment comprises use of a nanoparticle composition herein for genome editing in a subject. An embodiment comprises a method of genome editing in a subject comprising administering a nanoparticle composition herein to the subject. The nucleic acid in these embodiments may be sgRNA and Cas protein-encoding RNA(s). The nucleic acid in these embodiments may be one for genome editing via meganucleases, homing endonucleases, TALEN-based systems, or Zinc Finger Nucleases.

In an embodiment, the nanoparticle composition may be used for gene targeting or editing in a subject in vivo or ex vivo, e.g., by isolating cells from the subject, editing genes, and implanting the edited cells back into the subject. An embodiment comprises a method comprising administering a nanoparticle composition herein to isolated cells from a subject. The method may include gene targeting. The method may comprise implanting the edited cells back into the subject (or into another subject).

An embodiment comprises a method for introducing an agent into a cell. The method may comprise exposing the cell to a nanoparticle composition herein. The method may be a method of transfection when the agent is a nucleic acid. The agent may be introduced into cells by mixing a solution of nanoparticles composed as described herein with the liquid medium in which the cells are cultured.

Embodiments List

The following Embodiments List includes non-limiting embodiments.

The embodiments herein include but are not limited to those in the Embodiments List.

1. A nucleic acid carrier having, comprising, consisting essentially of, or consisting of a structure of formula Ia, formula Ib, formula Ic, formula Id, formula Ie, formula If, formula Ig, formula Ih, formula II, formula Ij, formula IIa or formula IIb:

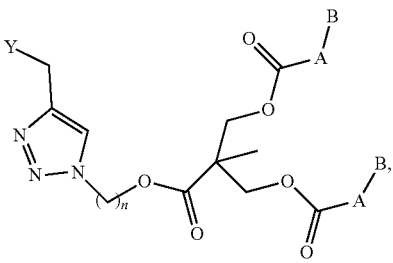

Formula Ia

Formula Ib
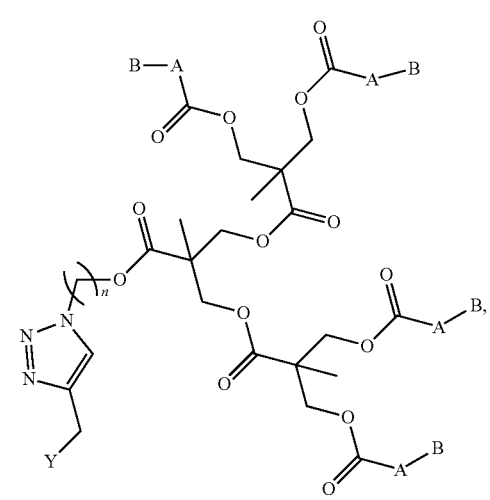
Formula If
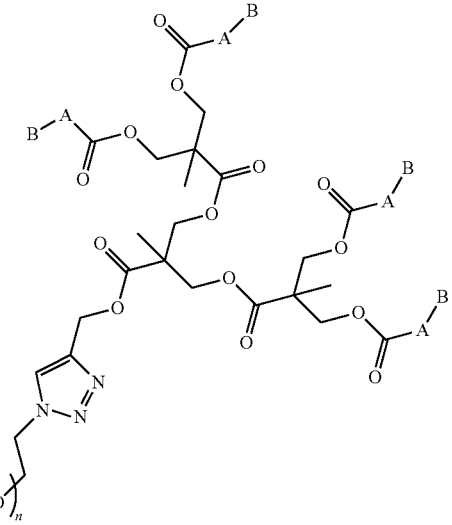
Formula Ic
Formula Ig
Formula Id
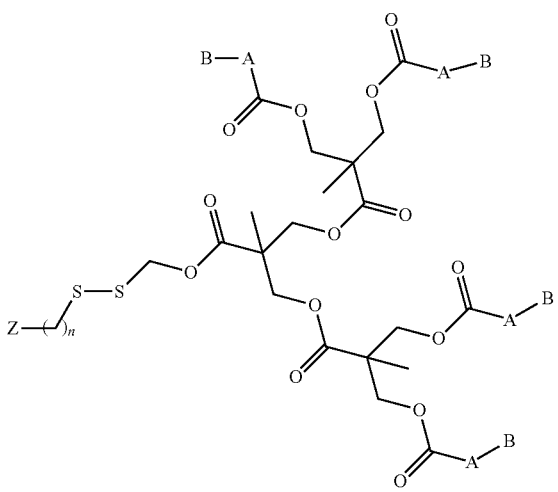
Formula Ih
Formula Ie
Formula Ii
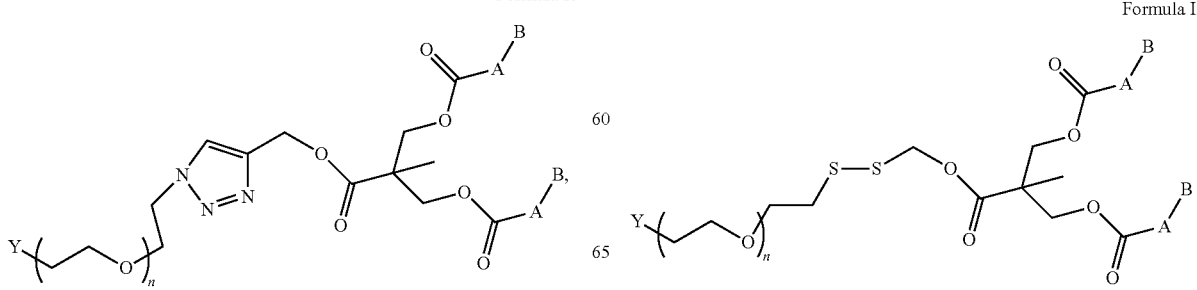

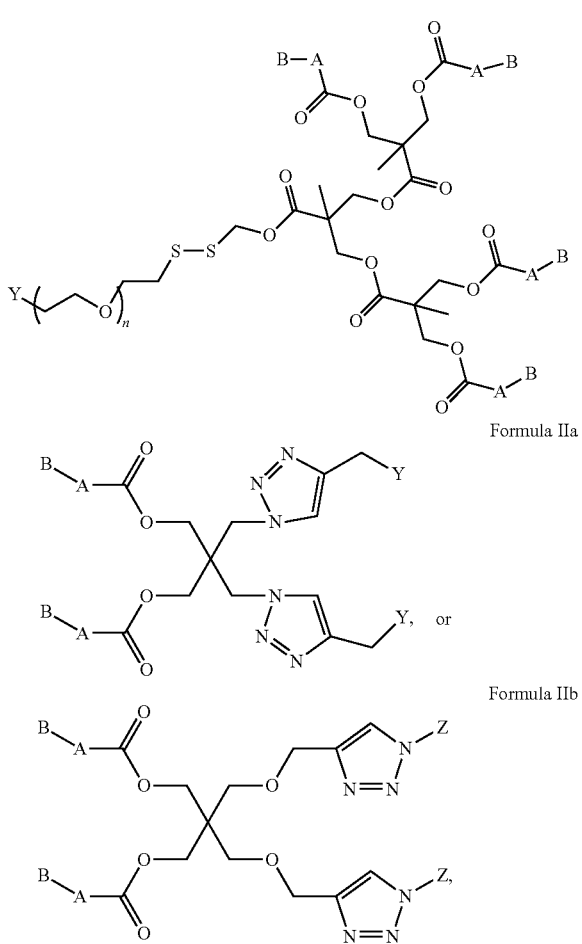

wherein A is an amine linker, B is a hydrophobic unit, n values from 0 to 20, Y is a sugar moiety, and Z is a deoxy sugar moiety 2. The nucleic acid carrier of embodiment 1, wherein A is derived from the group consisting of: N1-(2-aminoethyl)ethane-1,2-diamine, N1-(2-aminoethyl) propane-1,3-diamine, N1-(3-aminopropyl)propane-1,3-diamine, N1,N1'-(ethane-1,2-diyl)bis(ethane-1,2-diamine), N1,N1'-(ethane-1,2-diyl)bis(N2-(2-aminoethyl)ethane-1,2-diamine), N1-(2-(4-(2-aminoethyl)piperazin-1-yl)ethyl)ethane-1,2-diamine, N1-(2-aminoethyl)-N1-methylethane-1,2-diamine, N1-(3-aminopropyl)-N1-methylpropane-1,3-diamine, N1-(3-aminopropyl)-N1-ethylpropane-1,3-diamine, 3-((3-aminopropyl)(methyl)amino)propan-1-ol, 3,3'-(methylazanediyl)bis(propan-1-ol), N1-(3-aminopropyl)-N1-methylbutane-1,4-diamine, 4-((3-aminopropyl)(methyl)amino) butan-1-ol, 4-((3-hydroxypropyl)(methyl)amino)butan-1-ol, 4-((3-hydroxypropyl)(methyl)amino)butan-1-ol, N1-(4-aminobutyl)-N1-methylbutane-1,4-diamine, 4-((4-aminobutyl)(methyl)amino)butan-1-ol, 4,4'-(methylazanediyl)bis(butan-1-ol), 3-((3-aminopropyl)(ethyl)amino)propan-1-ol, 3,3'-(ethylazanediyl)bis(propan-1-ol), N1-(3-aminopropyl)-N1-ethylbutane-1,4-diamine, 4-(3 aminopropyl)(ethyl)amino)butan-1-ol, 4-(ethyl(3-hydroxypropyl)amino)butan-1-ol, N1-(2-aminoethyl)-N1-methylpropane-1,3-diamine, N1-(4-aminobutyl)-N1-ethylbutane-1,4-diamine, 4,4'-(ethylazanediyl)bis(butan-1-ol), 3-((3-aminopropyl)amino)propan-1-ol, N1-(3-aminopropyl) butane-1,4-diamine, 4-((3-hydroxypropyl)amino)butan-1-ol, N1-(4-aminobutyl)butane-1,4-diamine, 3,3'-azanediylbis (propan-1-ol), 4-((3-aminopropyl)amino)butan-1-ol, 4,4'-azanediylbis(butan-1-ol), N1,N1'-(butane-1,4-diyl)bis (propane-1,3-diamine), 2-(bis(3-aminopropyl)amino)ethan-1-ol, 2-((4-aminobutyl)(3-aminopropyl)amino)ethan-1-ol or 2-(bis(4-aminobutyl)amino)ethan-1-ol.

3. The nucleic acid carrier of embodiment 1 or 2, wherein B is a $C_1$-$C_{28}$ alkyl or $C_2$-$C_{28}$ alkenyl group.

4. The nucleic acid carrier of embodiment 3, wherein the $C_1$-$C_{28}$ alkyl or $C_2$-$C_{28}$ alkenyl group is substituted with one to four substituents selected from the group consisting of: halogen, —CN, —$NO_2$, —$N_3$, $C_1$-$C_6$ alkyl, halo($C_1$-$C_6$ alkyl), —OR, —$NR_2$, —$CO_2R$, —OC(O)R, —CON(R)$_2$, —OC(O)N(R)$_2$, —NHC(O)N(R)$_2$, —NHC(NH)N(R)$_2$, $C_3$-$C_8$ cycloalkyl, $C_3$-$C_8$ cycloalkenyl, aryl, heteroaryl, and heterocycle, and R is selected from the group consisting of: hydrogen, $C_1$-$C_6$ alkyl, halo($C_1$-$C_6$ alkyl), $C_3$-$C_8$ cycloalkyl, $C_3$-$C_8$ cycloalkenyl, aryl, heteroaryl, and heterocycle.

5. The nucleic acid carrier of embodiment 4, wherein each cycloalkyl, cycloalkenyl, aryl, heteroaryl, and heterocycle is further substituted with R' and R' is independently selected from the group consisting of: halogen, —CN, —$NO_2$, —$N_3$, $C_1$-$C_6$ alkyl, and halo($C_1$-$C_6$ alkyl).

6. The nucleic acid carrier of any one or more of embodiments 1-3, wherein B is selected from the group consisting of: methyl, ethyl, propyl, butyl, pentyl, hexyl, heptyl, octyl, nonyl, decyl, dodecyl, tridecyl, tetradecyl, pentadecyl, hexadecyl, heptadecyl, octadecyl, but-3-en-1-yl, oct-7-en-1-yl, 12-tridecenyl, 14-pentadecenyl, 17-octadecenyl, oleyl, linoleyl, arachidoneyl and ricinoleyl.

7. The nucleic acid carrier of any one of embodiments 1-3, wherein B is derived from a fatty acid.

8. The nucleic acid carrier of embodiment 7, wherein the fatty acid is selected from the group consisting of: caprylic acid, capric acid, lauric acid, myristic acid, palmitic acid, stearic acid, oleic acid, linoleic acid, linolenic acid, arachidonic acid, eicosapentaenoic acid, 12-hydroxy-9-cis-octadecenoic acid, 12-methyltetradecanoic acid, 12-methyltridecanoic acid, 14-methylhexadecanoic acid, 14-methylhexadecanoic acid, 18-methylnonadecanoic acid, 19-methylarachidic acid, isopalmitic acid, isostearic acid, phytanic acid, (±)-2-hydroxyoctanoic acid, (+)-3-hydroxydecanoic acid, (±)-3-hydroxyoctanoic acid, 10-hydroxydecanoic acid, 12-hydroxyoctadecanoic acid, 15-hydroxypentadecanoic acid, 16-hydroxyhexadecanoic acid, 2-hydroxyhexadecanoic acid, 2-hydroxytetradecanoic acid, 2-hydroxydodecanoic acid, DL-α-hydroxystearic acid, DL-ß-hydroxylauric acid, DL-ß-hydroxymyristic acid, and DL-ß-hydroxypalmitic acid, conjugated fatty acids (e.g., conjugated isomers of linoleic acid (e.g., 9,11-CLA); acetylenic fatty acids (e.g., crepenynic acid); allenic fatty acids (e.g., laballenic acid) or cyclopropenyl fatty acids (e.g., sterculic acid).

9. The nucleic acid carrier of any one or more of embodiments 7-8, wherein the fatty acid comprises one or more stable isotopes.

10. The nucleic acid carrier of embodiment 9, wherein the stable isotope is a stable isotope of carbon or hydrogen.

11. The nucleic acid carrier of embodiment 10, wherein the stable isotope of carbon is $^{13}C$.

12. The nucleic acid carrier of embodiment 10, wherein the stable isotope of hydrogen is $^{2}H$.

13. The nucleic acid carrier of embodiment 10, wherein the fatty acid that comprises the stable isotope is selected from the group consisting of: octanoic acid-1-$^{13}C$, octanoic acid-8-$^{13}$C, octanoic acid-8,8,8-d3, octanoic-$^2$H15 acid, decanoic acid-1-$^{13}$C, decanoic acid-10-$^{13}$C, decanoic-10,10,10-d3 acid, decanoic-d19 acid, undecanoic acid-1-$^{13}$C, lauric acid-12,12,12-$^2$H3, lauric-$^2$H23 acid, lauric acid-1-$^{13}$C, lauric acid-1,12-$^{13}$C$_2$, tridecanoic-2,2-$^2$H2 acid, myristic acid-14-$^{13}$C, myristic acid-1-$^{13}$C, myristic acid-14,14,14-$^2$H3, myristic-$^2$H27 acid, palmitic acid-1-$^{13}$C, palmitic acid-16-$^{13}$C, palmitic acid-16-$^{13}$C,16,16,16-$^2$H3, palmitic acid-$^2$H31, stearic acid-1-$^{13}$C, stearic acid-18-$^{13}$C, stearic acid-18,18,18-$^2$H3, stearic-$^2$H35 acid, oleic acid-1-$^{13}$C, oleic acid-$^2$H34, linolenic acid-1-$^{13}$C, linoleic acid-$^2$H32, arachidonic-5,6,8,9,11,12,14,15-$^2$H8 acid, and eicosanoic-$^2$H39 acid.

14. The nucleic acid carrier of any one or more of embodiments 1-13, wherein the Y of Formula Ia, Formula Ib, Formula Ie, Formula If, Formula Ii, Formula Ij or Formula IIa is a sugar.

15. The nucleic acid carrier of embodiment 14, wherein the sugar is selected from a furanose monosaccharide (e.g., xylo-, ribo-, or arabinofuranose), pyranose monosaccharide (e.g., glucose, mannose, galactose)disaccharide (e.g., lactose, trehalose), polysaccharide (e.g., cyclodextrin) or sugar derivatives. In an embodiment, the sugar derivative is a nucleoside or nucleotide.

16. The nucleic acid carrier of embodiment 1, wherein the Z of Formula Ic, Formula Id, Formula Ig or Formula Ih or Formula IIb is a deoxy sugar.

17. The nucleic acid carrier of embodiment 16, wherein sugar in the deoxy sugar is a furanose monosaccharide, pyranose monosaccharide, disaccharide, oligosaccharide, polysaccharide or sugar derivatives. In an embodiment, the sugar derivative is a nucleoside or nucleotide.

18. The nucleic acid carrier of embodiment 16-17, where the deoxy sugar is 2-deoxy-D-ribose, 6-deoxy-L-tagatose, 5-deoxy-xylo-, ribo-, or arabinofuranoses, 1-deoxy glucose, 2-deoxy glucose, 6-deoxy glucose, 1-deoxy mannose, 2-deoxy galactose, 6-deoxy galactose, 1-deoxy lactose, 6-Azidotrehalose, 6-Azido-2,4-diacetamido-2,4,6-trideoxy-D-mannose, or 6A-Azido-6A-deoxy-ß-cyclodextrin.

19. A nanoparticle composition comprising the nucleic acid carrier of any one or more of embodiments 1-18, and an agent enclosed therein.

20. The nanoparticle composition of embodiment 19, wherein the agent is a nucleic acid.

21. The nanoparticle composition of embodiment 19 or 20, wherein the agent is therapeutic or immunogenic, preferably the agent is a therapeutic or immunogenic nucleic acid.

22. The nanoparticle composition of embodiment 21, wherein the therapeutic or immunogenic nucleic acid agent is selected from the group consisting of: a polynucleotide, oligonucleotide, DNA, cDNA, RNA, repRNA, siRNA, miRNA, sgRNA, and mRNA.

23. The nanoparticle composition of embodiment 21 or 22, wherein the therapeutic or immunogenic nucleic acid agent encodes one or more antigens selected from the group consisting of infectious disease, pathogen, cancer, autoimmunity disease and allergenic disease.

24. The nanoparticle composition of any one or more of embodiments 21-23, wherein the therapeutic or immunogenic nucleic acid agent comprises an RNA or DNA capable of silencing, inhibiting or modifying the activity of a gene.

25. The nanoparticle composition of any one or more of embodiments 19-24 further comprising a PEG-lipid.

26. The nanoparticle composition of embodiment 25, wherein the PEG-lipid is 1,2-dimyristoyl-sn-glycero-3-phosphoethanolamine-N-[methoxy (poly-ethylene glycol)-2000] or 1,2-dimyristoyl-rac-glycero-3-methoxypolyethylene glycol-2000.

27. The nanoparticle composition of embodiment 25 or 26, wherein the nanoparticle composition comprises the PEG-lipid in a range from 1 mol % to 10 mol % of the PEG-lipid per nanoparticle composition.

28. The nanoparticle composition of any one of embodiments 19-25 further comprising (1) a phospholipid and/or (2) cholesterol or derivative thereof.

29. The nanoparticle composition of embodiment 28, wherein the nanoparticle composition comprises the phospholipid, and the phospholipid is 1,2-dioleoyl-sn-glycero-3-phosphoethanolamine (DOPE) or distearoylphosphatidylcholine (DSPC).

30. The nanoparticle composition of embodiment 28 or 29, wherein the nanoparticle composition comprises the phospholipid in a range from 10 mol % to 15 mol % of the phospholipid per nanoparticle composition.

31. The nanoparticle composition of any one or more of embodiments 28-30, wherein the nanoparticle composition comprises the cholesterol or derivative thereof in a range from 50 mol % to 75 mol % of the cholesterol or derivative thereof per nanoparticle composition.

32. A method for treating or preventing a disease or condition in a subject comprising: administering a therapeutically effective amount of the nucleic acid carrier of any one of embodiments 1-18 or the nanoparticle composition of any one of embodiments 19-31 to a subject in need thereof.

33. The method of embodiment 32, wherein the therapeutically effective amount of the nanoparticle composition comprises the therapeutic or immunogenic nucleic acid agent in a range from 0.01 mg nucleic acid to 10 mg nucleic acid per kg body weight of the subject.

34. The method of embodiment 33, wherein the subject is a mammal.

35. The method of embodiment 34, wherein the mammal is selected from the group consisting of: human, non-human primate, mouse, rat, dog, cat, horse, or cow, but is not necessarily limited to these examples.

EXAMPLES

The following non-limiting examples are provided to illustrate particular embodiments.

Example 1. Nanoparticle Compositions Containing Sugar or Deoxy-Sugar Conjugated Dendrons Alkyne and azido sugars are known as versatile starting materials in synthesizing a number of biologically active compounds, including amino sugars, nucleosides and many other glycosylated heterocycles. Further, the development of cycloaddition reactions between acetylenic compounds and azides ('click chemistry') has opened new possibilities in the area of glycoconjugates. Keeping in mind the above facts, we have synthesized novel nucleic acid carriers bearing triazole moiety (Formula Ia or Ib or Ic or Id) starting with sugar alkynes or deoxy sugar azides and polyesteramine dendrons with azide or acetylene in the focal point; and have evaluated them for their gene delivery potential in vitro as well as in vivo.

Example 1a. Nanoparticle Compositions Containing Deoxy Glucose Dendrons
An example of the synthesis of PE-G2-2-deoxyGlucose-A1 Ricinoleic as follows:
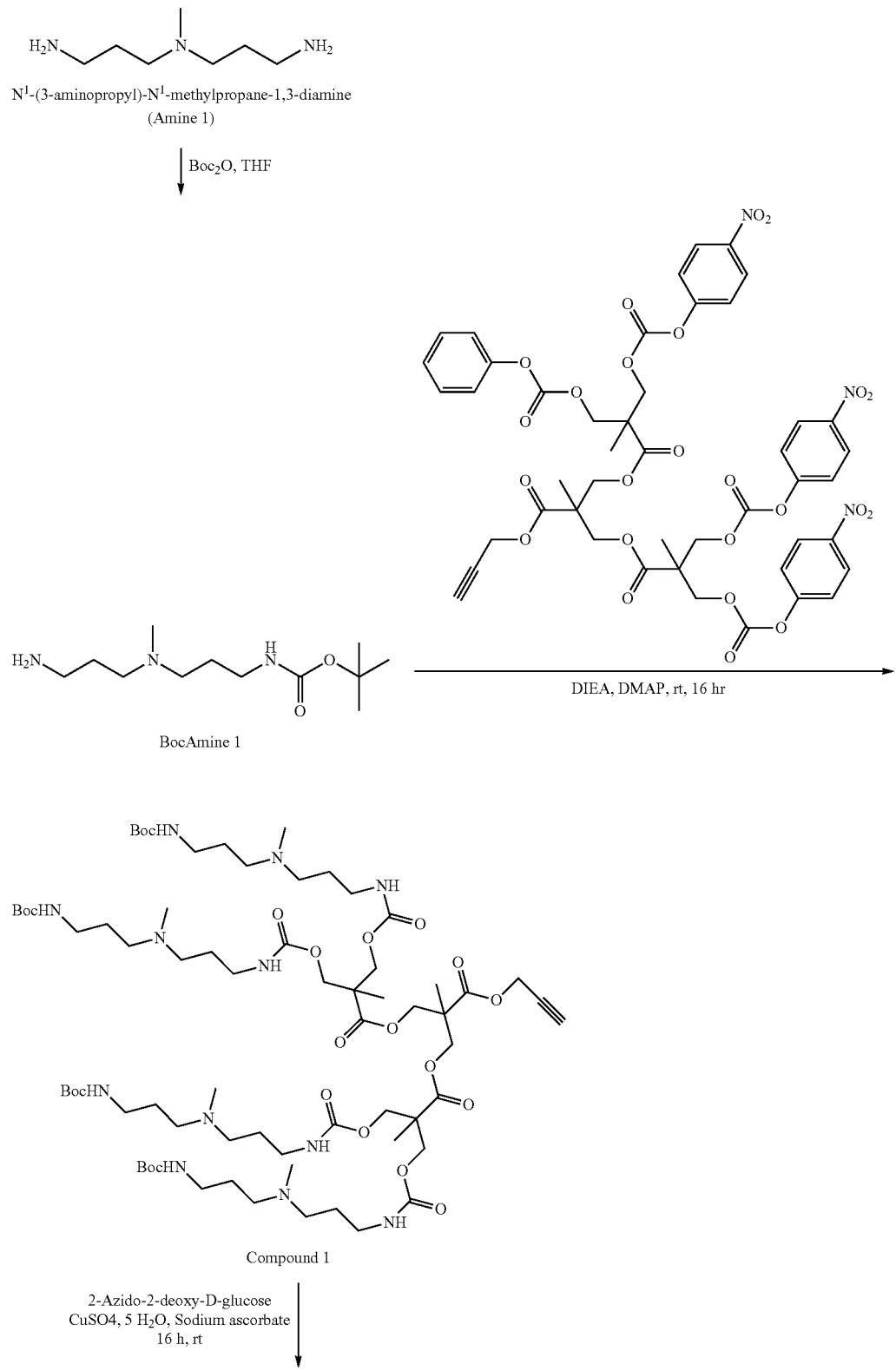

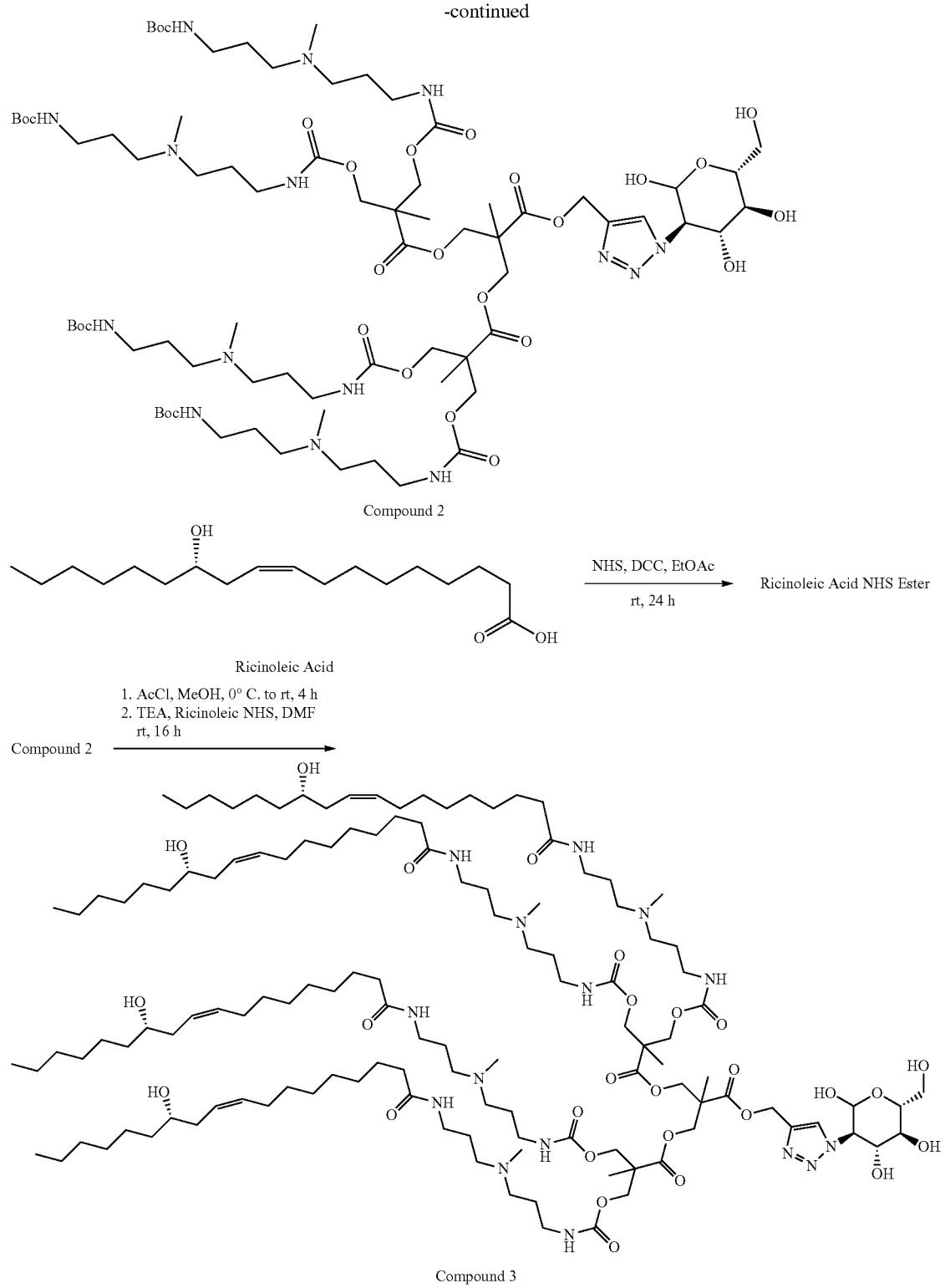

Compound 2: 2-Azido-2-deoxy-D-glucose (MW: 205.17, 17 mg, 0.079 μmol) was taken in 50 ml RBF (0.6 mL), then compound 1, PE-G2-acetylene-BocAmine1 (MW:1489, 118 mg, 74 μmol; as synthesized following published procedure: Barnard et al 2011, which is incorporated herein by reference as if fully set forth) dissolved in THF (1.2 mL) was added along with $CuSO_4.5H_2O$ (2 mg, 0.079 μmol, 10 mol %, MW 249.69) and sodium ascorbate (3.1 mg, 15.8 μmol, 20 mol %, MW 198.11), and degassed $THF:H_2O$ (2 mL, 1:1). The reaction mixture was stirred at 23° C. for 16 h. Next day TLC confirmed the reaction was completed. The reaction mixture was purified via flash chromatography on 24 g silica column with gradient elution from 100% CH2Cl2 (mobile phase a) to 75:22:3 CH$_2$Cl$_2$/MeOH/NH$_4$OHaq (by volume, mobile phase b). The desired product eluted at 71% mobile phase b (R$_f$=0.35 in 75:22:3CH$_2$Cl$_2$/MeOH/NH$_4$OHaq) to yield the desired product as yellow oil (70 mg, 52%). MS (ESI) calcd for C76H139N15O27 [M+H]+ m/z 1695.0, found 1695.8; [M+2H]2+ m/z 848.1, found 848.0; [M+3H]3+m/z 565.6, found 565.8. 1H NMR (301 MHz, CHLOROFORM-d) δ ppm 1.11-1.21 (m, 7H) 1.26-1.29 (m, 3H) 1.37-1.44 (m, 1H) 1.42 (s, 40H) 1.54-1.72 (m, 18H) 2.12-2.20 (m, 12H) 2.28-2.43 (m, 17H) 3.03-3.21 (m, 19H) 3.41-3.49 (m, 10H) 3.92-4.38 (m, 15H) 5.11-5.46 (m, 4H) 5.98-6.36 (m, 2H).

Compound 3: 70 mg of compound 3 (0.041 mmol) was treated with 20 eq of AcCl (0.06 ml) after dissolving the compound in 3 ml MeOH, the reaction was stirred at 0° C. to 23° C. for 4 h, evaporated to dryness and dissolved in 2 ml DMF, added 0.11 ml Et$_3$N (0.73 mmol, 20 eq) followed by 97.0 mg of Ricinoleic-NHS (as synthesized following published procedure: Talukder et al., Publication Number WO/2020/132196, which is incorporated herein by reference as if fully set forth) dissolved in 2 ml DMF. The reaction mixture was stirred at 23° C. for 24 h, concentrated under reduced pressure in Genevac, and The reaction mixture was purified via flash chromatography on silica column (12 g) with gradient elution from 100% CH2Cl2 (mobile phase a) to 75:22:3 CH$_2$Cl$_2$/MeOH/NH$_4$OHaq (by volume, mobile phase b). The desired product eluted at 55% mobile phase b. (R$_f$=0.3 in 75:22:3 CH$_2$Cl$_2$/MeOH/NH$_4$OHaq) to yield the desired product as yellow oil (30 mg, 30%). MS (ESI) calcd for C$_{76}$H139N15O27 [M+2H]2+ m/z 1209.0, found 1208.9; [M+3H]3+ m/z 805.9, found 806.2. 1H NMR (301 MHz, CHLOROFORM-d) δ ppm 0.83-0.89 (m, 13H) 1.11-1.32 (m, 81H) 1.39-1.47 (m, 11H) 1.54-1.74 (m, 23H) 1.92-2.23 (m, 38H) 2.35-2.55 (m, 15H) 3.04-3.31 (m, 17H) 3.52-3.65 (m, 5H) 3.93-4.37 (m, 13H) 5.30-5.60 (m, 8H) 6.18-6.44 (m, 2H) 6.82-7.01 (m, 2H)

Nanoparticle Formulation

Nanoparticles containing the deoxy sugar-modified polyesteramine dendron (e.g PE Dendron_G2-2 deoxyGlucose-A1-Ricinoleic):DOPE:cholesterol:DMG-PEG2k at molar ratios of 1:0.6:2.88:0.1 were formulated using NanoAssemblr Benchtop (Precision NanoSystems Inc, Vancouver, BC, Canada)). RNA was diluted with DNase/RNase-Free, endotoxin free distilled water and sterile citrate buffer to a final desired pH. Total flow rate was maintained at 8 mL per min at a 3:1 ratio of aqueous to organic phase for formulating on the Benchtop. Using glassware depyrogenated by heating at 250° C. for 24 hour, nanoparticles were dialyzed against sterile, endotoxin-free PBS using 20,000 molecular weight cutoff dialysis. Dialyzed nanoparticles were sterile filtered using 0.2 micron poly(ether sulfone) filters and characterized with a Zetasizer NanoZS machine (Malvern). The size distributions were characterized by a single peak with a low polydispersity index. Encapsulation efficiency was measured to be 95% for the nanoparticle composition containing PE Dendron_G2-2 deoxyGlucose-A1-Ricinoleic and SEAP mRNA (formulated at pH 5) using Ribogreen® assay (Geall et al. 10.1073/pnas.1209367109 which is incorporated herein by reference as if fully set forth).

Hydronamic Size Measurement

Figure 2:
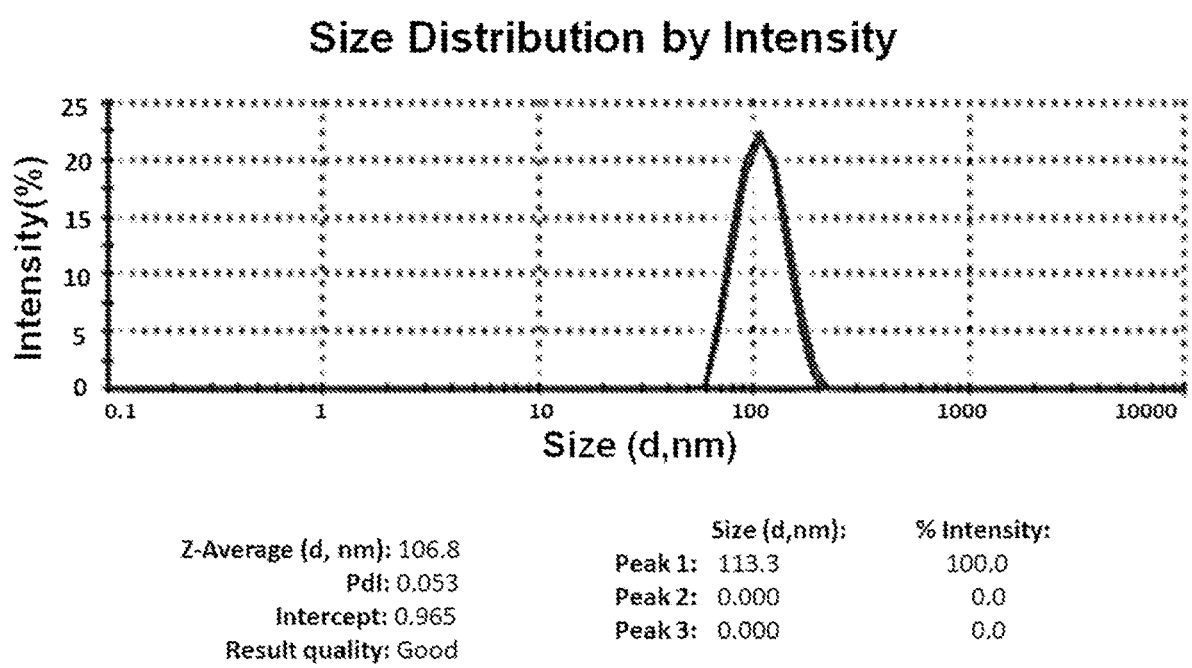
FIG. 2 illustrates the distribution of the nanoparticle compositions measured as the intensity based on size (d) of the nanoparticles.

FIG. 2 illustrates distribution of the nanoparticle composition measured as the intensity (Z average) based on size (d.nm; diameter in nm) of the nanoparticles. Referring to FIG. 2, the "Z average" of the nanoparticle composition containing PE Dendron_G2-2 deoxyGlucose-A1-Ricinoleic and SEAP mRNA as function of size was determined by dynamic light scattering (DLS). The strongest intensity was observed for the nanoparticles of 113.3 d.nm in size. The size distributions were characterized by a single peak with a low polydispersity index, indicating a relatively monodisperse size.

Gel Retardation Assay

Figure 3:
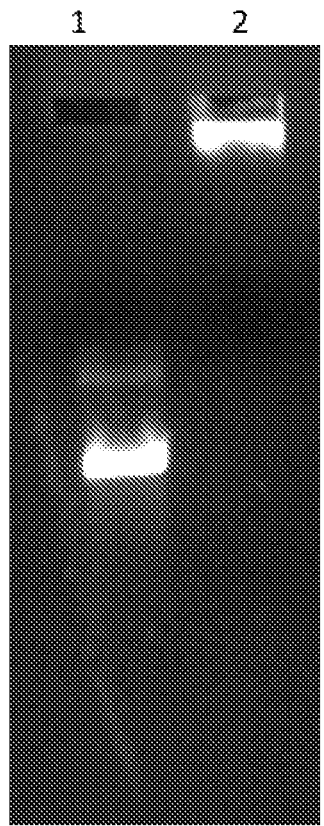
FIG. 3 illustrates a photograph of the agarose gel showing the binding of the PE Dendron_G2-2 deoxyGlucose-A1-Ricinoleic with RNA. The gels were stained with ethidium bromide (EB) and gel images were taken on a Syngene G Box imaging system (Syngene, USA).

Agarose gel electrophoresis was performed to evaluate the binding of sugar modified dendron with RNA according to the known method (Geall et al. 10.1073/pnas.1209367109, which is incorporated herein by reference as if fully set forth. FIG. 3 is a photograph of the agarose gel showing the binding of the sugar modified dendron with RNA. The gels were stained with ethidium bromide (EB) and gel images were taken on a Syngene G Box imaging system (Syngene, USA). Referring to FIG. 3, lane 1 contained the unformulated SEAP mRNA, lane 2 contained the product of formulation of the PE Dendron_G2-2 deoxyGlucose-A1-Ricinoleic and SEAP mRNA. Before loading, the samples were incubated with formaldehyde loading dye, denatured for 10 min at 65° C. and cooled to room temperature. The gel was run at 90 V and gel images were taken on a Syngene G Box imaging system (Syngene, USA). Referring to FIG. 4, the lower band corresponds to the small size free RNA (lane 1) and the top band represent the large size nanoparticles formed by binding of the RNA to the PE Dendron_G2-2 deoxyGlucose-A1-Ricinoleic carrier.

In Vitro SEAP Production Results.

To test the ability of the nanoparticles formulated with different deoxy sugar based dendrons to express SEAP in vitro, BHK cells were treated with nanoparticles. Each well of a 12 well dish of BHKs was treated with 20 μL (approximately 1 μg) of each formulation product diluted into a final volume of 500 μL with a 1:1 Optimem:PBS mix. The nontreated wells had 500 μL of 50/50 PBS/OptiMEM. Twenty four hours post-treatment or transfection, conditioned media from each culture was collected. The amount of SEAP was quantified using the Invitrogen NovaBright™ Phospha-Light™ EXP Assay kits for SEAP detection according to the manufacturer's protocol. The amount of SEAP in the media samples are reported in Arbitrary Units (A.U.) as measured in a BioTek Synergy HTX microplate reader. Error bars are ±S.E.M. Referring to FIG. 4a, it was observed that the SEAP amount was higher with the PE Dendron_G2-2 deoxyGlucose-A1-Ricinoleic than the other regioisomers: PE Dendron_G2-1 deoxyGlucose-A1-Ricinoleic and PE Dendron_G2-6 deoxyGlucose-A1-Ricinoleic. Referring to FIG. 5a, it was observed that the SEAP amount was higher with the PE Dendron_G2-2 deoxyGlucose-A5-Ricinoleic than PE Dendron_G2-2 deoxyGlucose-A1-Ricinoleic; and PE Dendron_G2-2 deoxyGalactose-A5-Ricinoleic nanoparticles expressed higher amount of SEAP in BHK cells than the other deoxy sugar based dendrons such as PE Dendron_G2-2 deoxyGlucose-A5-Ricinoleic and PE Dendron_G2-1 deoxyMannose-A5-Ricinoleic. For the no treatment Negative Control, 5 μL of media from a well not treated with nanoparticles was used.

In Vivo SEAP Production Results.

To test formulations of different monosaccharides based dendrons, the secreted embryonic alkaline phosphatase SEAP reporter system was used. For in vivo tests, mice were injected with nanoparticles at a dose of 5 ug of SEAP mRNA, and 16 hrs later, serum was collected from the mice. The amount of quantified using the Invitrogen NovaBright™ Phospha-Light™ EXP Assay kits for SEAP detection according to the manufacturer's protocol. The amount of SEAP in the mouse serum samples are reported in Arbitrary Units (A.U.) as measured in a BioTek Synergy HTX microplate reader. Error bars are ±S.E.M. Referring to FIG. 4b, it was observed that the SEAP amount was higher with the PE Dendron_G2-1 deoxyGlucose-A1-Ricinoleic than the other regioisomers: PE Dendron_G2-2 deoxyGlucose-A1-Ricinoleic and PE Dendron_G2-6 deoxyGlucose-A1-Ricinoleic. Referring to FIG. 5b, it was also observed that the SEAP amount was higher with the PE Dendron_G2-2 deoxyGlucose-A5-Ricinoleic than PE Dendron_G2-2 deoxyGlucose-A1-Ricinoleic indicating pKa of the ionizable delivery molecules influences the ability of the nanoparticles to deliver functionally active RNA.

COVID-19 Spike Trimer Direct Serum ELISA

Figure 6:
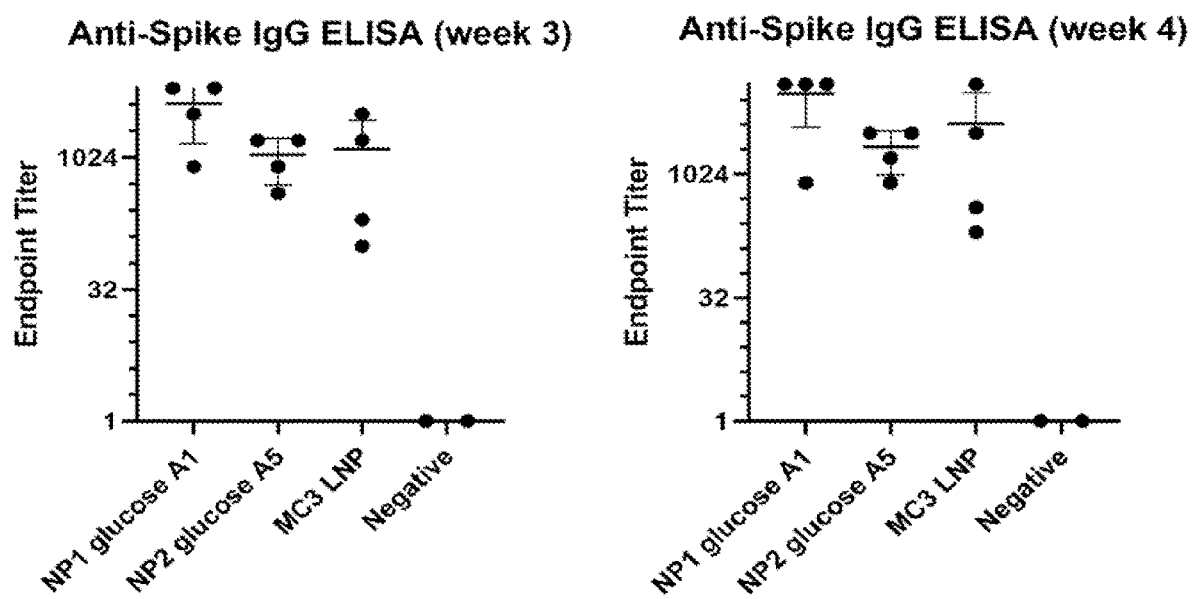
FIG. 6 illustrates endpoint dilution titers for mouse serum IgG specific to SARS-CoV-2 Spike protein after vaccination with SARS-CoV-2 Spike replicon RNA formulated with PE Dendron_G2-2 deoxyGlucose-A1-Ricinoleic or PE Dendron_G2-2 deoxyGlucose-A5-Ricinoleic delivery materials. An additional group of mice was vaccinated with the same RNA formulated with the aminolipid DLin-MC3-DMA (control).

Mice (BALB/c) were vaccinated by IM injection bilaterally in the leg muscle with 2.5 µg of Spike Replicon RNA formulated with PE Dendron_G2-2 deoxyGlucose-A1-Ricinoleic and PE Dendron_G2-2 deoxyGlucose-A5-Ricinoleic (in a total volume of 100 µL PBS). Mice were bled both 21 days and 28 days post injection, and serum was isolated from whole blood by centrifuging coagulated samples at 10000 RCF for 1.5 minutes. This serum was assayed for anti-Spike antibody titer by direct ELISA. Nunc MaxiSorp ELISA plates were coated overnight with pH 9.5 bicarbonate coating buffer containing recombinant Spike trimer protein at 4° C. Wells were blocked with PBS+1% BSA. For week 3 samples, serum was added to the wells starting at a 1:50 dilution and with serial 1:2 solutions up to 1:6400 in PBS+1% BSA; and for week 4 samples, serum was added to the wells starting at a 1:100 dilution and with serial 1:2 solutions up to 1:12800 in PBS+1%. Samples were incubated at RT for 1 hour, washed 3 times with PBST, and then goat anti-mouse IgG HRP was added at a 1:3000 dilution in PBS+1% BSA and incubated for 1 hour. Plates were again washed 5 times with PBST and developed using the chromogenic HRP substrate 3,3',5,5'-Tetramethylbenzidine (TMB). The reaction was stopped by addition of $H_2SO_4$ and absorbance was measured at 450 nm and 570 nm. Endpoint titer was designated as the highest dilution at which the value of Absorbance at 450-Absorbance at 570 was >0.08. At week 3 and week 4 the endpoint dilution titer in the group immunized with 2.5 µg of nanoparticle vaccine formulated using PE Dendron_G2-2 deoxyGlucose-A1-Ricinoleic was higher than PE Dendron_G2-2 deoxyGlucose-A5-Ricinoleic (FIG. 6). Referring to FIG. 6, it was also observed that both of our novel sugar based dendrons proved superior to Dlin-MC3-DMA for immunogenicity upon IM administration. Dlin-MC3-DMA also known as MC3, is one of the most utilized cationic lipids that is used for making Lipid Nano-Particles (LNPs), and thus has been used as a control in the assay.

Example 1b. Nanoparticle Compositions Containing Disaccharides

In order for the interactions between receptors and carbohydrates to be biologically relevant, multiple copies of these interactions have to be made either sequentially or simultaneously (Mortell et al, Journal of American Chemical Society 1996, 118, 2297-2298). In order to study the effect of multiple monosaccharides on cellular uptake and nucleic acid delivery, in the current invention, the focal point of the dendron has been modified with disaccharide.

An example of the synthesis of PE-G2-1-deoxyLactose-A1 Ricinoleic as follows:

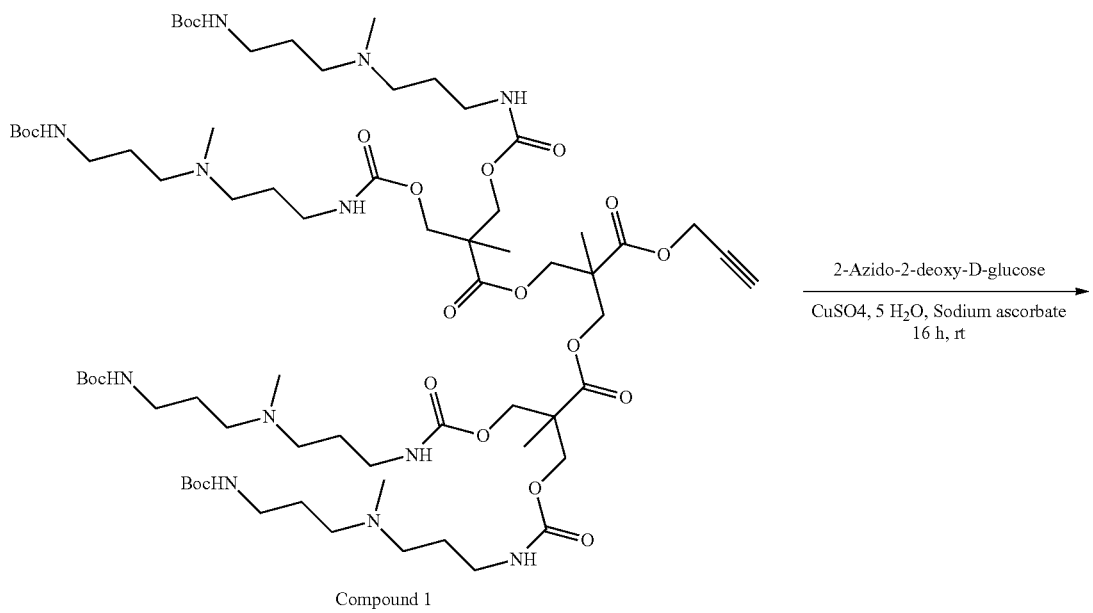

Compound 1

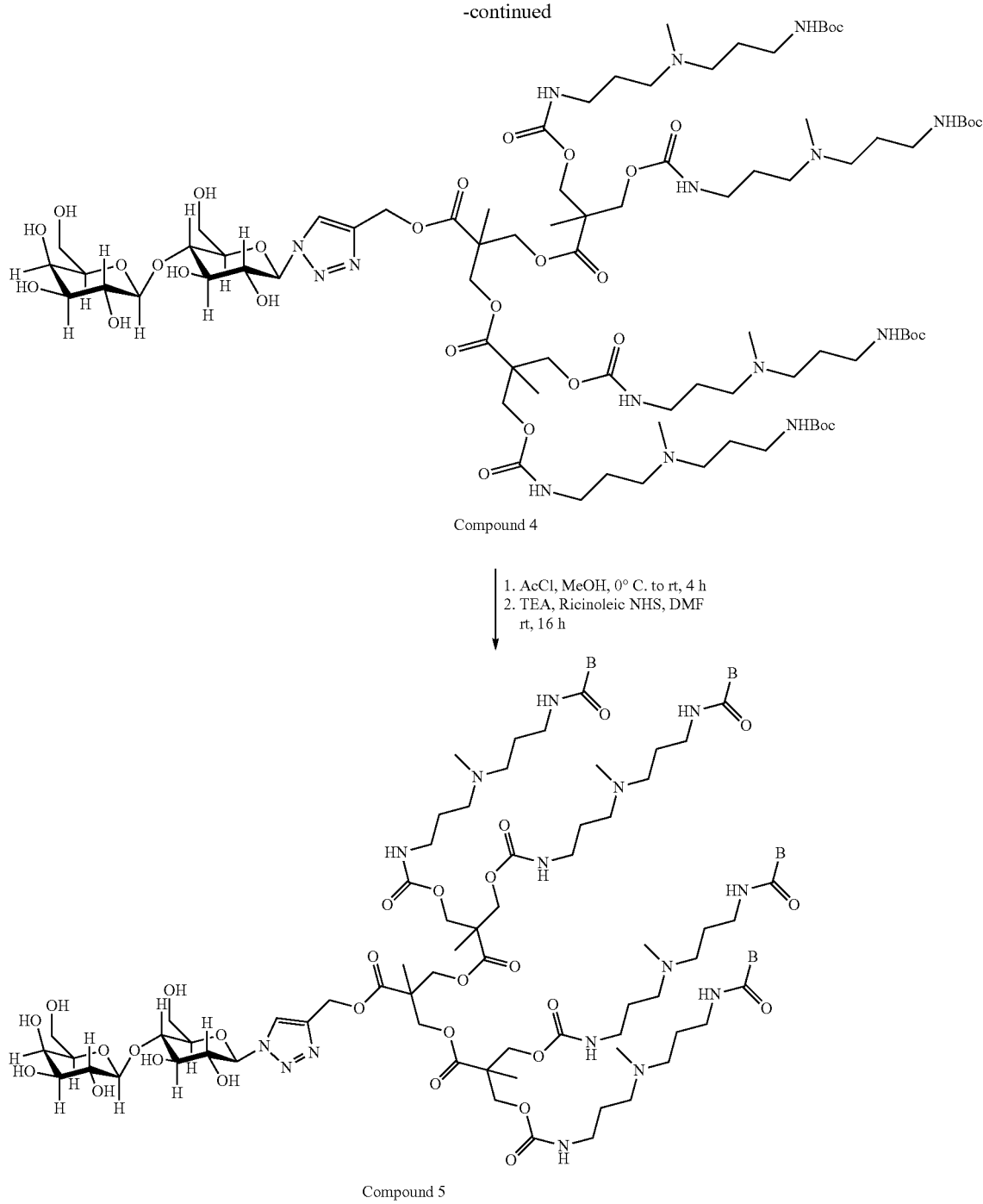

Compound 5

B = Ricinoleic acid tail

Compound 4: 1-Azido-1-deoxy-beta-D-lactopyranoside (MW: 367.31, 65 mg, 0.18 mmol) was taken in 50 ml RBF, dissolved in 1 ml THF, then Alkyne, PE-G2-acetylene-BocAmine1 (MW:1489, 200 mg, 0.13 mmol) dissolved in THF (2 mL) was added along with $CuSO_4 \cdot 5H_2O$ (3.3 mg, 0.013 mmol, 10 mol %, MW 249.69) and sodium ascorbate (5.1 mg, 0.026 mmol, 20 mol %, MW 198.11), and degassed THF:$H_2O$ (2 mL, 1:1). The reaction mixture was stirred at 23° C. for 16 h. Next day TLC confirmed the reaction completed. The reaction mixture was purified via flash chromatography on 24 g silica column with gradient elution from 100% $CH_2Cl_2$ (mobile phase a) to 75:24:6 $CH_2Cl_2$/MeOH/$NH_4$OHaq (by volume, mobile phase b). The desired product eluted at 100% mobile phase b. ($R_f$=0.6 in 75:24:6 $CH_2Cl_2$/MeOH/$NH_4$OHaq) to yield the compound 4 as yellow oil (150 mg, 60%). MS (ESI) calcd for $C_{82}H_{149}N_{15}O_{32}$ [M+2H]$^{2+}$ m/z 929.1, found 929.2. 1H NMR (301 MHz, CHLOROFORM-d) δ ppm 1.08-1.28 (m, 8H) 1.30-1.45 (m, 41H) 1.54-1.77 (m, 15H) 2.22-2.38 (m, 12H) 2.40-2.61 (m, 15H) 2.96-3.23 (m, 16H) 3.41-3.47 (m, 8H) 3.60-4.55 (m, 37H) 4.60-4.79 (m, 2H) 5.11-5.38 (m, 1H) 5.55-5.85 (m, 4H) 6.19-6.41 (m, 3H) 8.10-8.30 (m, 1H).

Compound 5: 100 mg of compound 4 (0.054 mmol) was treated with 20 eq of AcCl (0.08 ml, 1.08 mmol) after dissolving the compound in 3 ml MeOH, the reaction was stirred at 0° C. to 23° C. for 4 h, evaporated to dryness and dissolved in 2 ml DMF, added 0.15 ml Et$_3$N (1.08 mmol, 20 eq) followed by 128 mg of Ricinoleic-NHS (as synthesized following published procedure: Talukder et al., Publication Number WO/2020/132196, which is incorporated herein by reference as if fully set forth) dissolved in 2 ml DMF. The reaction mixture was stirred at 23° C. for 24 h, concentrated under reduced pressure in Genevac, and the reaction mixture was purified via flash chromatography on silica column (12 g) with gradient elution from 98% CH2Cl2 (mobile phase a) to 75:24:6 CH$_2$Cl$_2$/MeOH/NH$_4$OHaq (by volume, mobile phase b). The desired product eluted at 100% mobile phase b. (R$_f$=0.6 in 75:24:6 CH$_2$Cl$_2$/MeOH/NH$_4$OHaq) to yield the desired product as yellow oil (28 mg, 17% over two steps). MS (ESI) calculated for C$_{134}$H245N15O32 [M+2H]$^{2+}$ m/z 1289.5, found 1290.0. 1H NMR (301 MHz, CHLOROFORM-d) δ ppm 0.85-0.90 (m, 12H) 1.21-1.33 (m, 76H) 1.40-1.48 (m, 10H) 1.51-1.72 (m, 25H) 1.95-2.07 (m, 10H) 2.07-2.25 (m, 32H) 2.31-2.49 (m, 17H) 3.05-3.29 (m, 17H) 3.52-3.66 (m, 6H) 3.73-4.34 (m, 21H) 5.29-5.55 (m, 8H) 6.24-6.37 (m, 2H) 6.89-7.09 (m, 2H) 8.05-8.24 (m, 1H).

Example 1c. Nanoparticle Compositions Containing Polysaccharides Like Cyclodextrin Polysaccharides have various intrinsic biological functions such as immunostimulatory efficiency, anti Human Immunodeficiency Virus (anti HIV), and antitumor activity (Hong et al., 2017). Among the various polysaccharides cyclodextrin has got special attention since it is water soluble, have a hydrophobic cavity and a hydrophilic outer surface (Chem. Soc. Rev., 2011,40, 1586-1608). In order to study the effect of unique structural features of cyclodextrin on cellular uptake and nucleic acid delivery, in the current invention, the focal point of the dendron was modified with beta-cyclodextrin. The amines present in the delivery molecule will allow electrostatic interaction with the negatively charged nucleic acid at low pH, whereas the presence of hydrophilic outer surface in cyclodextrin should facilitate complexation and intracellular uptake of nucleic acid drugs.

An example of the synthesis of PE-G2-6-Deoxy cyclodextrin-A1 Ricinoleic as follows:

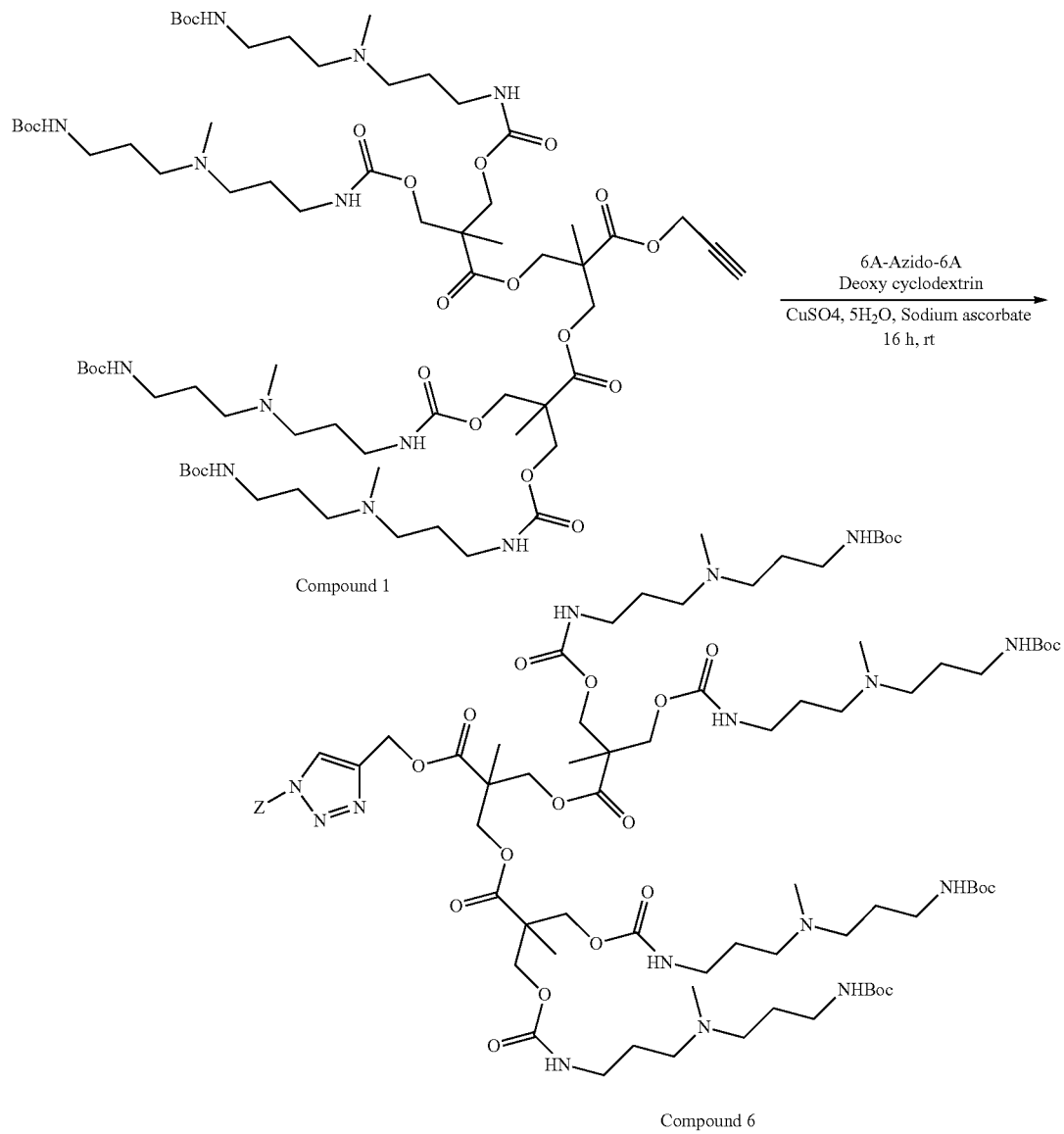

-continued

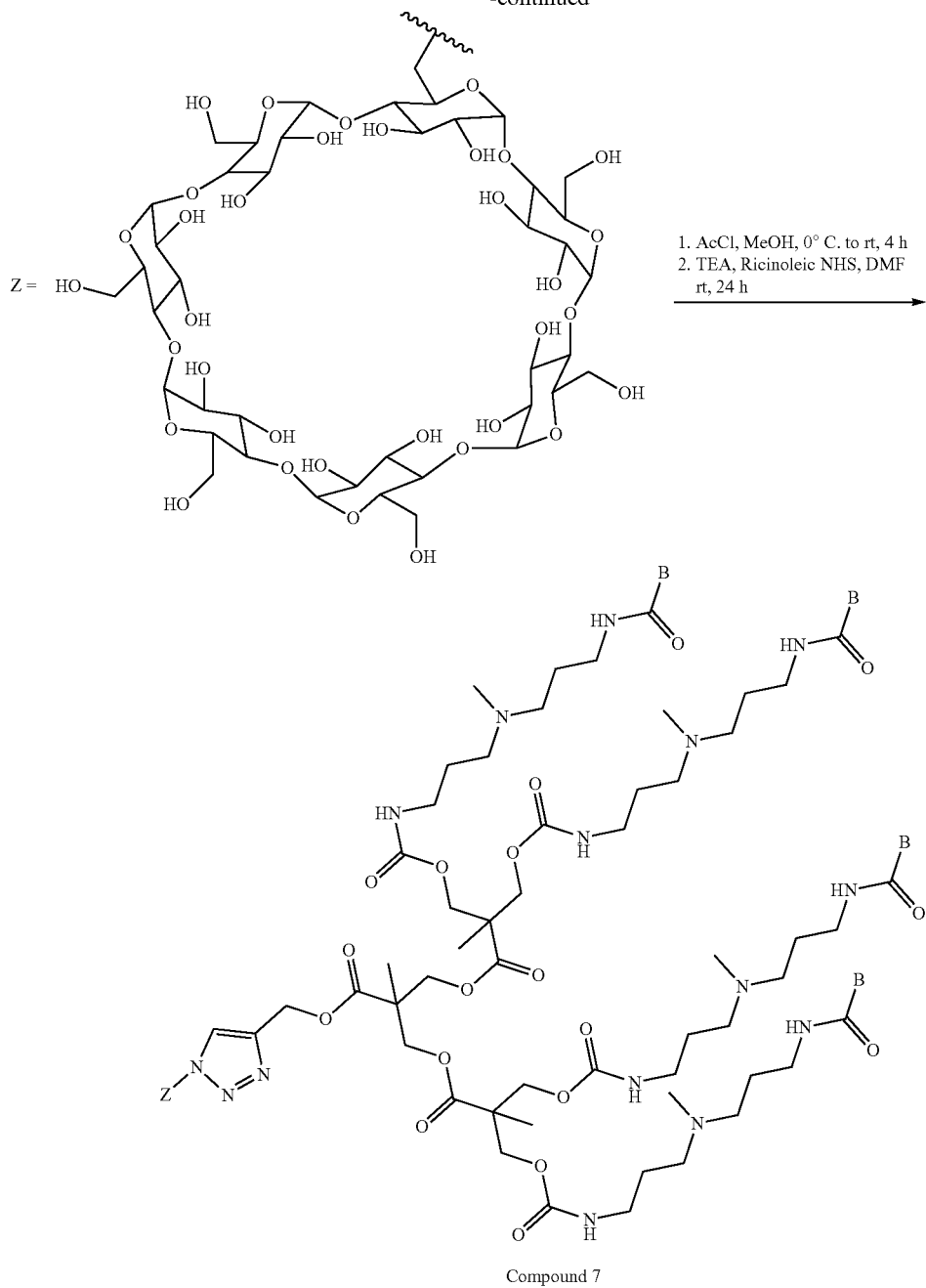

B = Ricinoleic acid tail

Compound 6: 6A-Azido-6A Deoxy cyclodextrin (MW: 1160, 75 mg, 0.065 mmol) was taken in 50 ml RBF, dissolved in 1 ml THF, then Alkyne, PE-G2-acetylene-BocAmine1 (MW:1489, 100 mg, 0.065 mmol) dissolved in THF (1 mL) was added along with $CuSO_4 \cdot 5H_2O$ (1.7 mg, 0.0065 mmol, 10 mol %, MW 249.69) and sodium ascorbate (2.6 mg, 0.013 mmol, 20 mol %, MW 198.11), and degassed THF:H2O (2 mL, 1:1). The reaction mixture was stirred at 23° C. for 16 h. Next day TLC confirmed the reaction was completed. The reaction mixture was purified via flash chromatography on 24 g silica column with gradient elution from 100% CH2Cl2 (mobile phase a) to 75:24:6 $CH_2Cl_2$/MeOH/$NH_4$OHaq (by volume, mobile phase b). The desired product eluted at 100% mobile phase b. ($R_f$=0.35 in 75:22:3 $CH_2Cl_2$/MeOH/$NH_4$OHaq) to yield the desired product as yellow oil (58 mg, 52%). MS (ESI) calcd for C112H197N15O56 $[M+2H]^{2+}$ m/z 1325.2, found 1325.2. 1H NMR (301 MHz, Solvent) δ ppm 1.15-1.30 (m, 9H) 1.44-1.49 (m, 36H) 1.61-1.83 (m, 16H) 2.29-2.42 (m, 12H) 2.47-2.65 (m, 16H) 3.01-3.19 (m, 17H) 3.28-3.33 (m, 5H) 3.37-3.63 (m, 15H) 3.69-3.97 (m, 22H) 4.05-4.33 (m, 11H) 4.92-5.00 (m, 11H) 5.03-5.17 (m, 3H) 5.22-5.32 (m, 2H) 8.06-8.12 (m, 1H).

Compound 7: 56 mg of compound 3 (0.021 mmol) was treated with 20 eq of AcCl (0.03 ml, 0.42 mmol) after dissolving the compound in 3 ml MeOH, the reaction was stirred at 0° C. to 23° C. for 4 h, evaporated to dryness and dissolved in 2 ml DMF, added 0.06 ml Et$_3$N (0.42 mmol, 20 eq) followed by 50.2 mg of Ricinoleic-NHS, 6 eq (as synthesized following published procedure: Talukder et al., Publication Number WO/2020/132196, which is incorporated herein by reference as if fully set forth) dissolved in 2 ml DMF. The reaction mixture was stirred at 23° C. for 24 h, concentrated under reduced pressure in Genevac, and the reaction mixture was purified via flash chromatography on silica column (12 g) with gradient elution from 100% CH$_2$Cl$_2$ (mobile phase a) to 75:24:6 CH$_2$Cl$_2$/MeOH/NH$_4$OHaq (by volume, mobile phase b). The desired product eluted at 100% mobile phase b. ($R_f$=0.3 in 75:24:6 CH$_2$Cl$_2$/MeOH/NH$_4$OHaq) to yield the desired product as yellow oil (20 mg, 30%). MS (ESI) calcd for C164H293N15O56 [M+3H]$^{3+}$ m/z 1124.0, found 1124.5.

Example 1d. Nanoparticle Compositions Containing Dendrons with Formula Ib

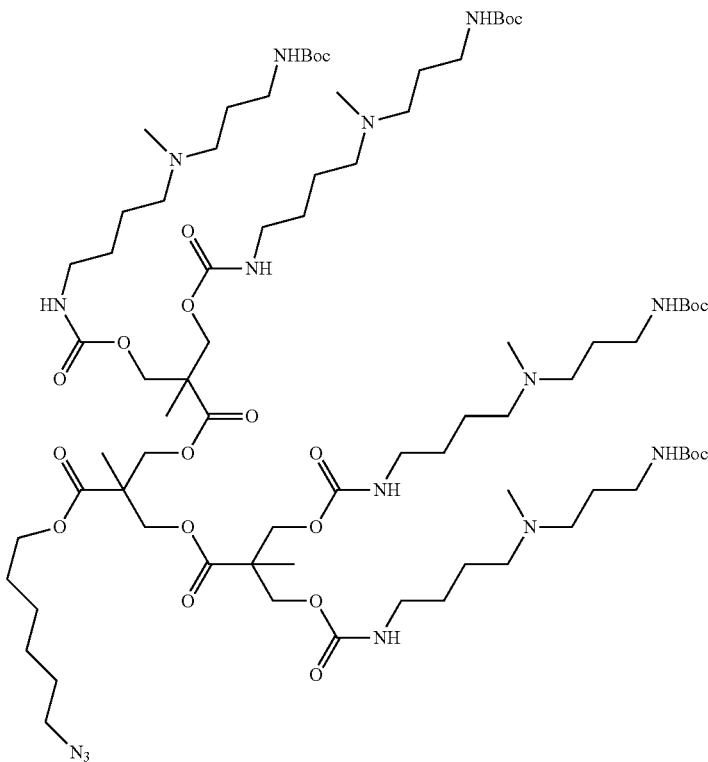

Compound 8
Chemical Formula: C$_{77}$H$_{145}$N$_{15}$O$_{22}$
Molecular Weight: 1633.09

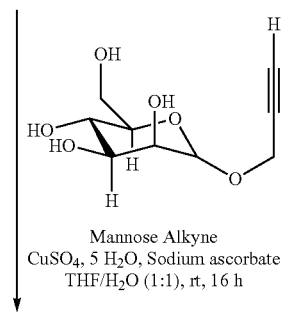

Mannose Alkyne
CuSO$_4$, 5 H$_2$O, Sodium ascorbate
THF/H$_2$O (1:1), rt, 16 h

-continued
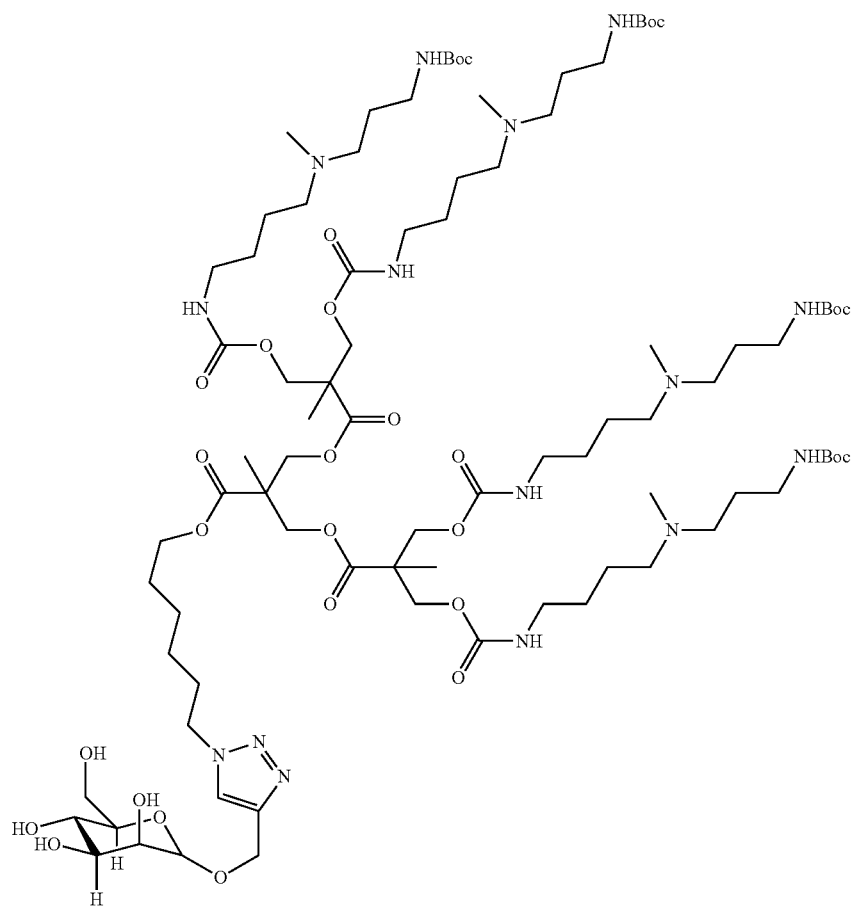
Compound 9
Chemical Formula: $C_{86}H_{159}N_{15}O_{28}$
Molecular Weight: 1851.30
1. AcCl, MeOH, 0° C. to rt, 5 h
2. Ricinoleic NHS, Et$_3$N
   DMF, rt, 16 h

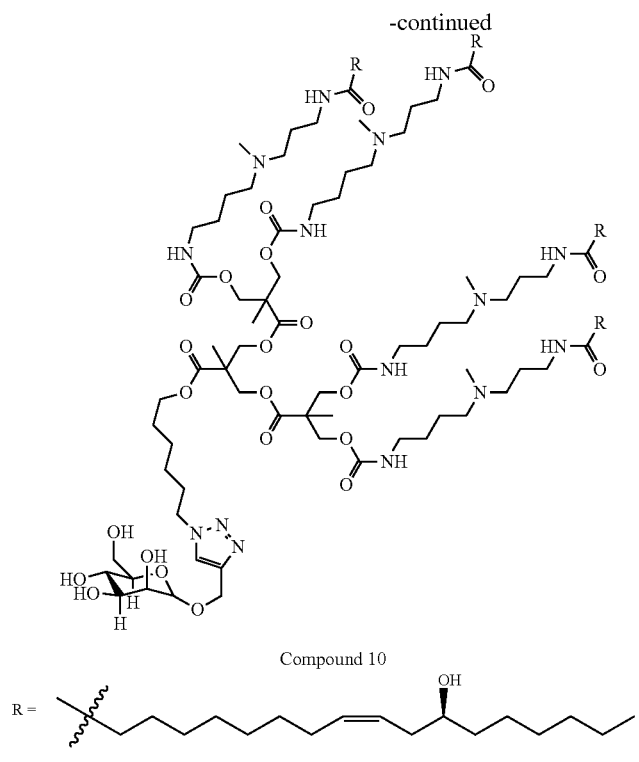

Compound 10

R = ![structure]

Compound 9: Mannose alkyne (MW: 218.21, 67 mg, 0.31 mmol; as synthesized following published procedure: Percec et al 2011 J. Am. Chem. Soc. 2013, 135, 9055-9077, which is incorporated herein by reference as if fully set forth) was taken in 50 ml RBF (0.6 mL), then compound 8, PE-G2-azide-BocAmine5 (MW:1489, 118 mg, 74 μmol; as synthesized from PE-G2-azide-OH following published procedure: Barnard et al 2011, which is incorporated herein by reference as if fully set forth) dissolved in THF (1 mL) was added along with $CuSO_4 \cdot 5H_2O$ (7.6 mg, 10 mol %, MW 249.69) and sodium ascorbate (12 mg, 20 mol %, MW 198.11), and degassed $THF:H_2O$ (2 mL, 1:1). The reaction mixture was stirred at 23° C. for 16 h. Next day TLC confirmed the reaction was completed. The reaction mixture was purified via flash chromatography on 24 g silica column with gradient elution from 100% CH2Cl2 (mobile phase a) to 75:22:3 $CH_2Cl_2/MeOH/NH_4OH$aq (by volume, mobile phase b). The desired product eluted at 70-% mobile phase b ($R_f$=0.2 in 2:1 mobile phase b/mobile phase a) to yield the desired product as yellow oil (136 mg, 92%). MS (ESI) calcd for C86H159N15O28 [M+2H]2+ m/z 926.0, found 925.9.

Compound 10: 136 mg of compound 9 (0.073 mmol) was treated with 20 eq of AcCl (0.105 ml) after dissolving the compound in 3 ml MeOH, the reaction was stirred at 0° C. to 23° C. for 5 h, evaporated to dryness and dissolved in 2 ml DMF, added 0.11 ml $Et_3N$ (1.46 mmol, 20 eq) followed by 174 mg of Ricinoleic-NHS (as synthesized following published procedure: Talukder et al., Publication Number WO/2020/132196, which is incorporated herein by reference as if fully set forth) dissolved in 2 ml DMF. The reaction mixture was stirred at 23° C. for 24 h, concentrated under reduced pressure in Genevac, and the reaction mixture was purified via flash chromatography on silica column (24 g) with gradient elution from 100% CH2Cl2 (mobile phase a) to 75:22:3 $CH_2Cl_2/MeOH/NH_4OH$aq (by volume, mobile phase b). The desired product eluted at 80% mobile phase b. ($R_f$=0.65 in 75:22:3 $CH_2Cl_2/MeOH/NH_4OH$aq) to yield the desired product as yellow oil (56 mg, 30%). MS (ESI) calcd for C139H256N14O28 [M+2H]2+ m/z 1285.9, found 1285.0.

Nanoparticle Formulation

Nanoparticles containing the sugar-modified polyesteramine dendron (e.g PE Dendron_G2-HexylMannose-A5-Ricinoleic):DOPE:cholesterol:PEG at molar ratios of 1:0.6:2.88:0.1 were formulated using NanoAssemblr Benchtop (Precision NanoSystems Inc, Vancouver, BC, Canada)). RNA was diluted with DNase/RNase-Free, endotoxin free distilled water and sterile citrate buffer to a final desired pH. Total flow rate was maintained at 8 mL per min at a 3:1 ratio of aqueous to organic phase for formulating on the Benchtop. Using glassware depyrogenated by heating at 250° C. for 24 hour, nanoparticles were dialyzed against sterile, endotoxin-free PBS using 20,000 molecular weight cutoff dialysis. Dialyzed nanoparticles were sterile filtered using 0.2 micron poly(ether sulfone) filters and characterized with a Zetasizer NanoZS machine (Malvern). The size distributions were characterized by a single peak with a low polydispersity index. Encapsulation efficiency was measured to be 90% for the nanoparticle composition containing PE Dendron_G2-HexylMannose-A5-Ricinoleic and SEAP mRNA using Ribogreen® assay (Geall et al. 10.1073/pnas.1209367109 which is incorporated herein by reference as if fully set forth).

Hydronamic Size Measurement

Figure 7:
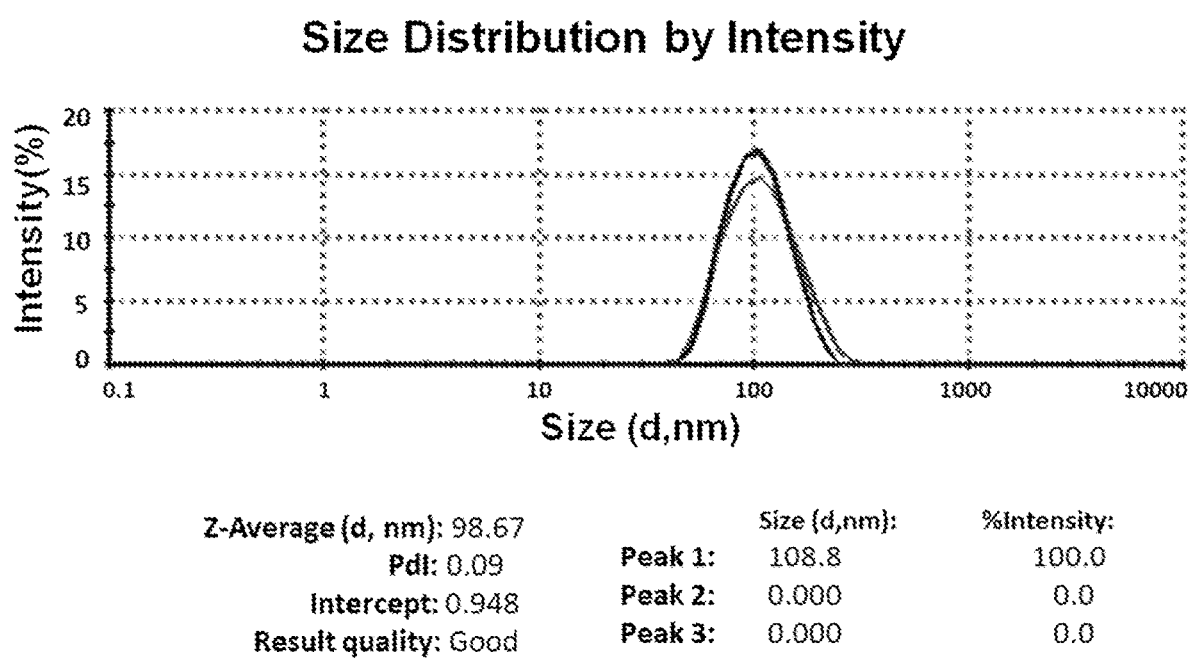

FIG. 7 illustrates distribution of the nanoparticle composition measured as the intensity (Z average) based on size (d.nm; diameter in nm) of the nanoparticles. Referring to FIG. 7, the "Z average" of the nanoparticle composition containing PE Dendron_G2-HexylMannose-A5-Ricinoleic and SEAP mRNA as function of size was determined by dynamic light scattering (DLS). The strongest intensity was observed for the nanoparticles of 108.8 d.nm in size. The size distributions were characterized by a single peak with a low polydispersity index, indicating a relatively monodisperse size.

In Vivo SEAP Production Results.

Figure 8:
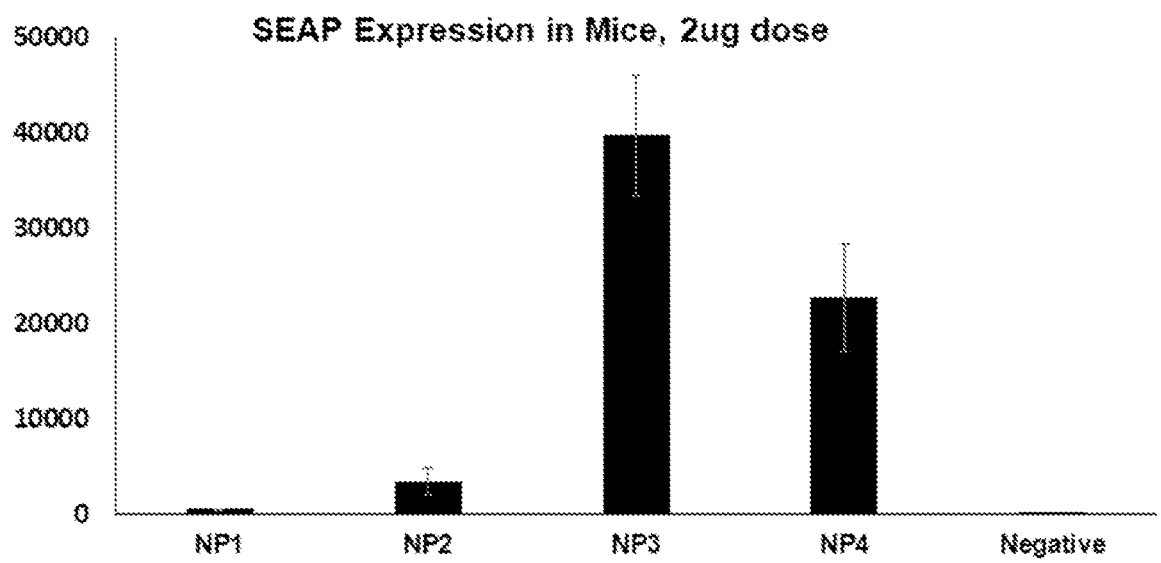

To test formulations with PE Dendron_G2-HexylMannose-A5-Ricinoleic using different class of PEG in vivo, mice were injected with nanoparticles at a dose of 2 ug of SEAP mRNA, and 3 days after administration, serum was collected from the mice. The amount of quantified using the Invitrogen NovaBright™ Phospha-Light™ EXP Assay kits for SEAP detection according to the manufacturer's protocol. The amount of SEAP in the mouse serum samples are reported in Arbitrary Units (A.U.) as measured in a BioTek Synergy HTX microplate reader. Error bars are ±S.E.M. Referring to FIG. 8, it was observed that the SEAP amount was higher with PEG-lipid conjugate ALC 0159 and DMG PEG 2000 as compared to formulations with 14:0 PEG 2000 and 184:0 PEG 2000.

Example 1e. Nanoparticle Compositions Containing Dendrons with Formula If

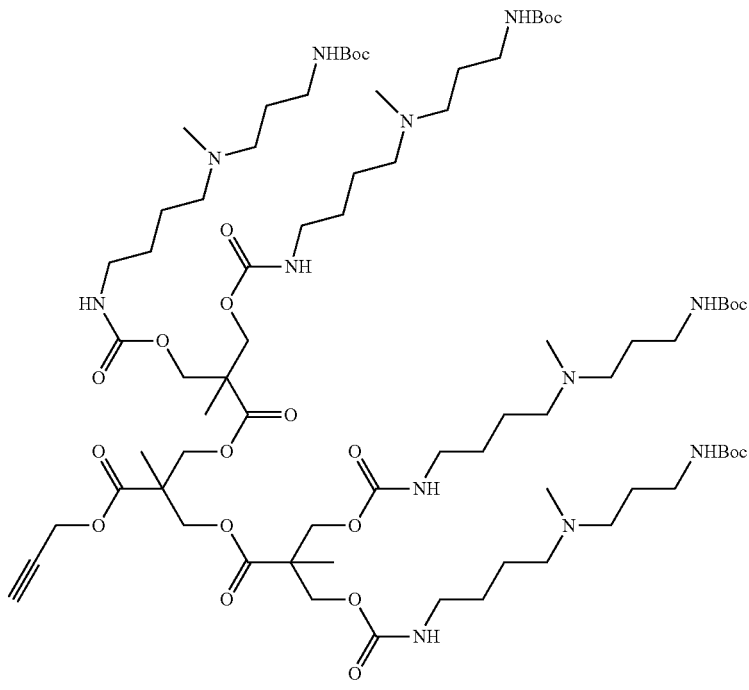

Compound 11
Chemical Formula: C74H136N12O22
Molecular Weight: 1545.96

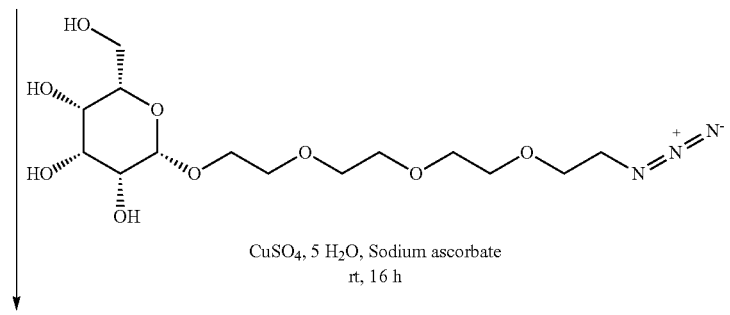

CuSO4, 5 H2O, Sodium ascorbate
rt, 16 h

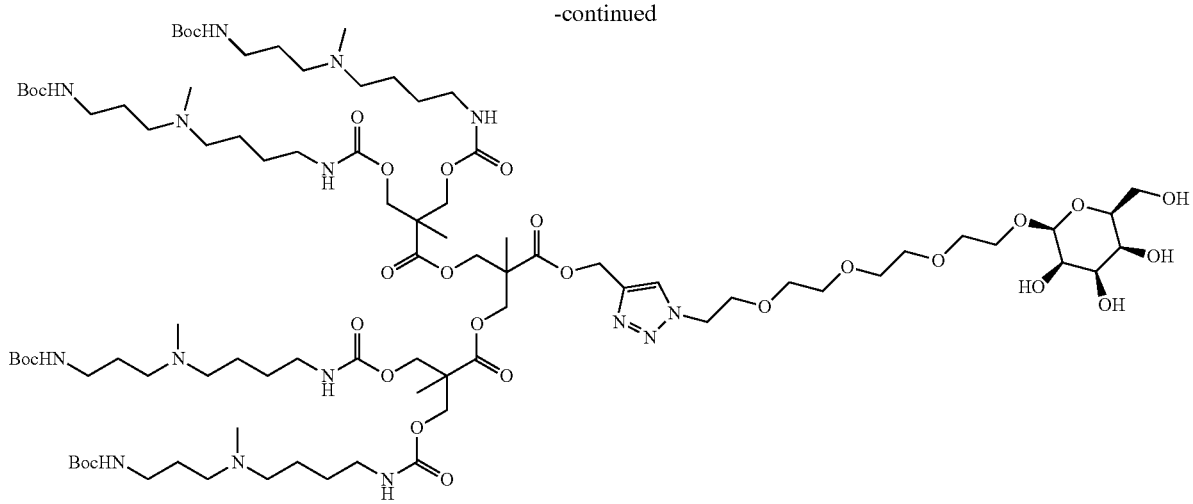

Compound 12

Chemical Formula: $C_{88}H_{163}N_{15}O_{31}$
Molecular Weight: 1926.16

1. AcCl, MeOH, 0° C. to rt, 5 h
2. Ricinoleic NHS, Et₃N DMF, rt, 16 h

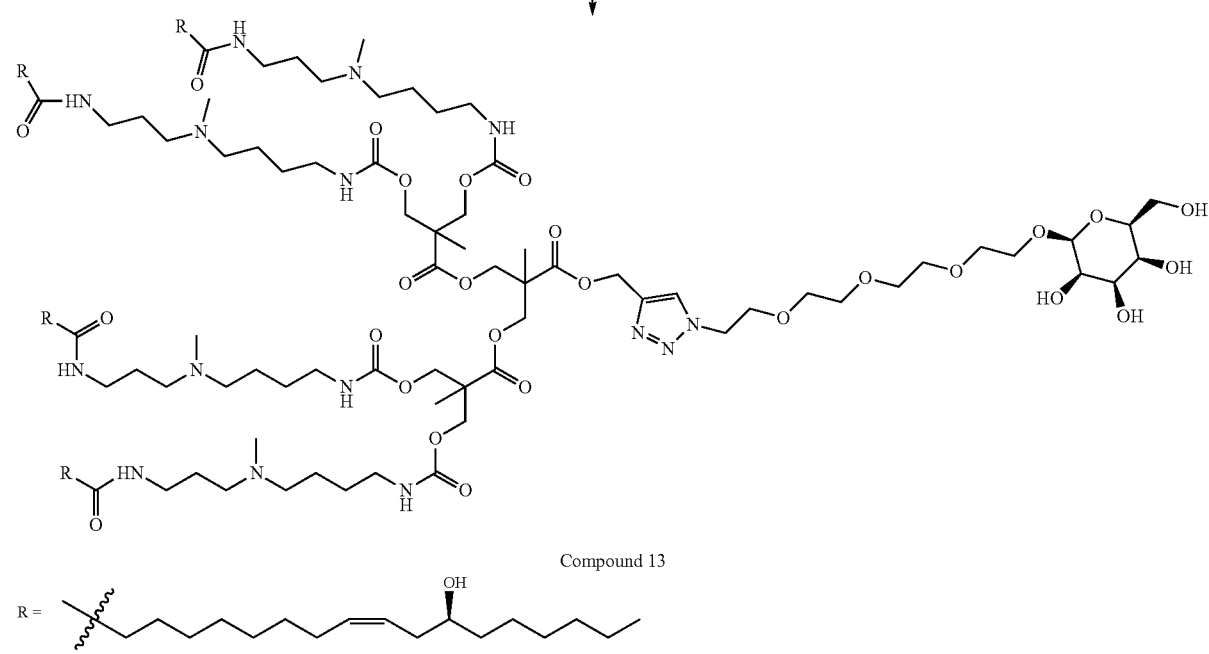

Compound 13

Compound 12: Azido-PEG4-beta-D-glucose (MW: 381, 50 mg, 0.18 mmol) dissolved in 0.6 mL was taken in 25 ml RBF, then Alkyne, PE-G2-acetylene-BocAmine5 (MW: 1546, 101 mg, 66 μmol as synthesized from PE-G2-acetylene-OH following published procedure: Barnard et al 2011, which is incorporated herein by reference as if fully set forth) dissolved in THF (1 mL) was added along with CuSO4.5H2O (3.3 mg, 20 mol %, MW 249.69) and sodium ascorbate (5.2 mg, 40 mol %, MW 198.11), and degassed THF:H2O (2 mL, 1:1) was added to it. The reaction mixture was stirred at 23° C. for 2 days. The reaction mixture was purified via flash chromatography on 12 g silica column with gradient elution from 100% CH2Cl2 (mobile phase a) to 75:22:3 CH₂Cl₂/MeOH/NH₄OHaq (by volume, mobile phase b). The desired product eluted at 100% mobile phase b ($R_f$=0.25 in 75:22:3CH₂Cl₂/MeOH/NH₄OHaq) to yield the desired product as yellow oil (49 mg, 39%). MS (ESI) calcd for C76H139N15O27 [M+2H]2+ m/z 964.7, found 964.4; [M+3H]3+ m/z 643.4, found 643.5.

Compound 13: 49 mg of compound 12 (0.025 mmol) was treated with 20 eq of AcCl (0.04 ml, 0.51 mmol) after dissolving the compound in 3 ml MeOH, the reaction was stirred at 0° C. to 23° C. for 5 h, evaporated to dryness and dissolved in 2 ml DMF, added 0.07 ml Et₃N (0.51 mmol, 20 eq) followed by 60.0 mg of Ricinoleic-NHS (0.153 mmol, as synthesized following published procedure: Talukder et al., Publication Number WO/2020/132196, which is incorporated herein by reference as if fully set forth) dissolved in 2 ml DMF. The reaction mixture was stirred at 23° C. for 24 h, concentrated under reduced pressure in Genevac, and The reaction mixture was purified via flash chromatography on silica column (24 g) with gradient elution from 100% CH2Cl2 (mobile phase a) to 75:22:3 CH$_2$Cl$_2$/MeOH/NH$_4$OHaq (by volume, mobile phase b). The desired product eluted at 100% mobile phase b. ($R_f$=0.3 in 75:22:3 CH$_2$Cl$_2$/MeOH/NH$_4$OHaq) to yield the desired product as yellow oil (35 mg, 52%). MS (ESI) calcd for C140H259N15O31 [M+3H]3+ m/z 883.7, found 883.3.

Nanoparticle Formulation

Nanoparticles containing the sugar-modified polyesteramine dendron (e.g PE Dendron_G2-PEG4-Glucose-A5-Ricinoleic):DOPE:cholesterol:PEG-lipid conjugate at molar ratios of 1:0.6:2.88:0.1 were formulated using NanoAssemblr Benchtop (Precision NanoSystems Inc, Vancouver, BC, Canada)). RNA was diluted with DNase/RNase-Free, endotoxin free distilled water and sterile citrate buffer to a final desired pH. Total flow rate was maintained at 8 mL per min at a 3:1 ratio of aqueous to organic phase for formulating on the Benchtop. Using glassware depyrogenated by heating at 250° C. for 24 hour, nanoparticles were dialyzed against sterile, endotoxin-free PBS using 20,000 molecular weight cutoff dialysis. Dialyzed nanoparticles were sterile filtered using 0.2 micron poly(ether sulfone) filters and characterized with a Zetasizer NanoZS machine (Malvern). The size distributions were characterized by a single peak with a low polydispersity index.

Hydronamic Size Measurement

Figure 9:
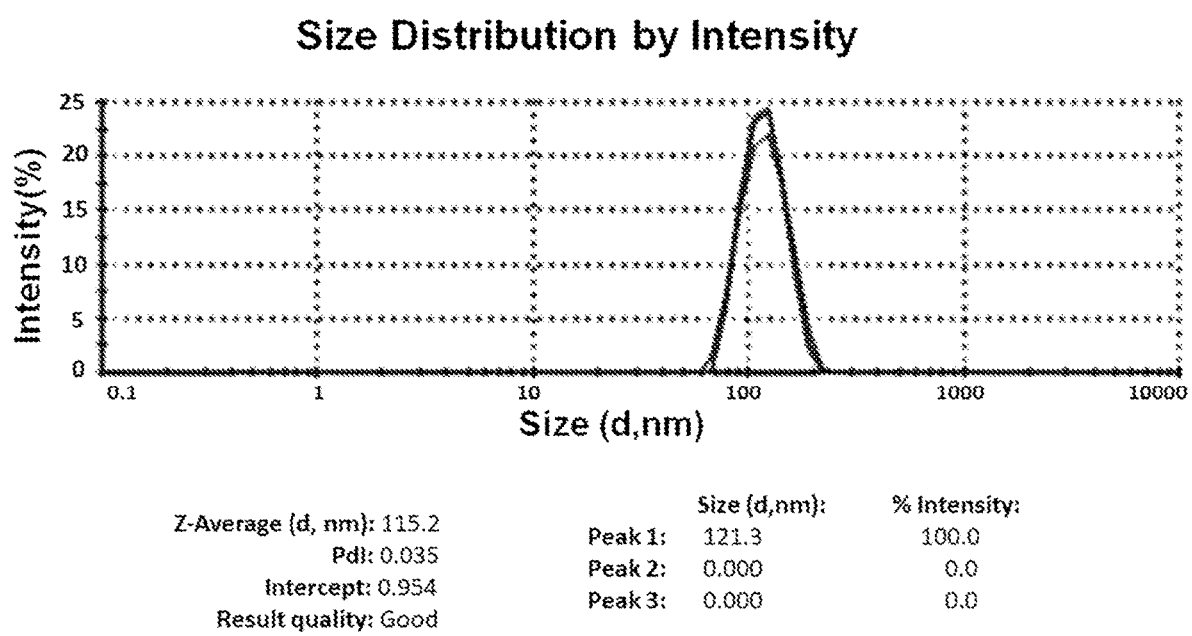

FIG. 9 illustrates distribution of the nanoparticle composition measured as the intensity (Z average) based on size (d.nm; diameter in nm) of the nanoparticles. Referring to FIG. 9, the "Z average" of the nanoparticle composition containing PE Dendron_G2-PEG4-Glucose-A5-Ricinoleic and PR8 HA mRNA as function of size was determined by dynamic light scattering (DLS). The strongest intensity was observed for the nanoparticles of 121.3 d.nm in size. The size distributions were characterized by a single peak with a low polydispersity index, indicating a relatively monodisperse size.

Example 2. Nanoparticle Compositions Containing Amphiphilic Dendrimers as Nucleic Acid Carriers In the current invention, we have synthesized sugar and deoxy sugar-modified amphiphilic dendrimer hybrids. These amphiphilic molecules have hydrophobic units, thus should be able to self-assemble in solution whereas the hydrophilic sugar moieties should improve biocompatibility and loading capacity of the nucleic acid carrier.

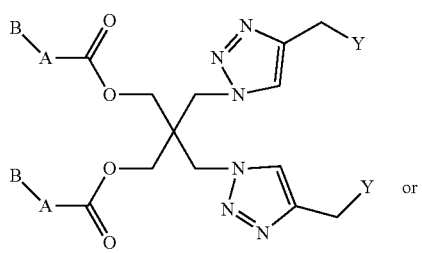

Formula Ie

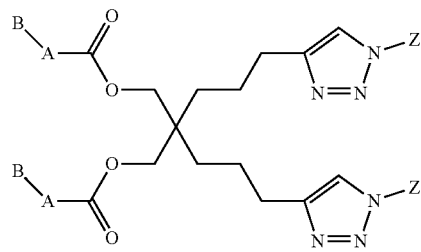

Formula If where A is an amine linker, B is a hydrophobic unit, Y is a sugar moiety and Z is a deoxy sugar moiety

REFERENCES

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

(1) Jones, C. H., Chen, C. K., Ravikrishnan, A., Rane, S., and Pfeifer, B. A. (2013) Overcoming nonviral gene delivery barriers: perspective and future. Mol. Pharmaceutics 10, 4082-4098.

(2) Nishikawa, M., and Huang, L. (2001) Nonviral vectors in the new millennium: delivery barriers in gene transfer. Hum. Gene Ther. 12, 861-870

(3) Mintzer, M. A., and Simanek, E. E. (2009) Nonviral Vectors for Gene Delivery. Chem. Rev. 109, 259-302.

(4) a. Hong S J, Ahn M H, Sangshetti J, Choung P H, Arote R B. Sugar-based gene delivery systems: Current knowledge and new perspectives. Carbohydr Polym. 2018 Feb. 1; 181:1180-1193. doi: 10.1016/j.carbpol.2017.11.105. Epub 2017 Nov. 28. PMID: 29253947; b. Han, S., Ganbold, T., Bao, Q., Yoshida, T., & Baigude, H. (2018). Sugar Functionalized Synergistic Dendrimers for Biocompatible Delivery of Nucleic Acid Therapeutics. Polymers, 10(9), 1034.

(5) Geall A J, Verma A, Otten G R, Shaw C A, Hekele A, Banerjee K, Cu Y, Beard C W, Brito L A, Krucker T, O'Hagan D T, Singh M, Mason P W, Valiante N M, Dormitzer P R, Barnett S W, Rappuoli R, Ulmer J B, Mandl C W. Nonviral delivery of self-amplifying RNA vaccines. Proc Natl Acad Sci U.S.A. 2012 Sep. 4; 109 (36):14604-9. doi: 10.1073/pnas.1209367109. Epub 2012 Aug. 20. PMID: 22908294; PMCID: PMC3437863.

(6) Mortell, K. H.; Weatherman, R. V.; Kiessling, L. L., Recognition specificity of neoglycopolymers prepared by ring-opening metathesis polymerization. Journal of the American Chemical Society 1996, 118, 2297-2298.

(7) Carmen Ortiz Mellet, José M. García Fernándezb and Juan M. Benito. Chem. Soc. Rev., 2011,40, 1586-1608

(8) Barnard A, Posocco P, Pricl S, Calderon M, Haag R, Hwang M E, Shum V W, Pack D W, Smith D K. Degradable self-assembling dendrons for gene delivery: experimental and theoretical insights into the barriers to cellular uptake. J Am Chem Soc. 2011 Dec. 21; 133(50): 20288-300.

(9) Poulami Talukder, Jasdave S. Chahal, Justine S. McPartlan, Omar Khan, Karl Ruping. Nanoparticle Compositions for Efficient Nucleic Acid Delivery and Methods of Making and Using the Same. PCT/US19/67402.

(10) Percec V, Leowanawat P, Sun H J, Kulikov O, Nusbaum C D, Tran T M, Bertin A, Wilson D A, Peterca M, Zhang S, Kamat N P, Vargo K, Moock D, Johnston E D, Hammer D A, Pochan D J, Chen Y, Chabre Y M, Shiao T C, Bergeron-Brlek M, André S, Roy R, Gabius H J, Heiney P A. Modular synthesis of amphiphilic Janus glycodendrimers and their self-assembly into glycodendrimersomes and other complex architectures with bioactivity to biomedically relevant lectins. J Am Chem Soc. 2013 Jun. 19; 135(24):9055-77. doi: 10.1021/ja403323y. Epub 2013 Jun. 6. PMID: 23692629.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A nucleic acid carrier comprising a structure of:

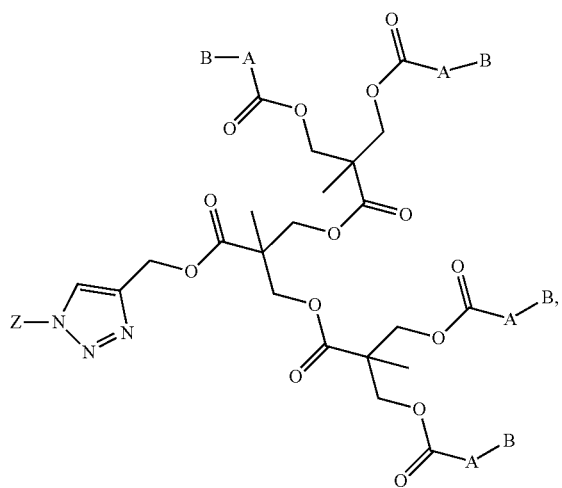

Formula Id wherein A is an amine linker, B is a hydrophobic unit, and Z is a deoxy sugar moiety.

2. The nucleic acid carrier of claim 1, wherein A is derived from the group consisting of: N1-(2-aminoethyl)ethane-1,2-diamine, N1-(2-aminoethyl) propane-1,3-diamine, N1-(3-aminopropyl)propane-1,3-diamine, N1,N1'-(ethane-1,2-diyl)bis(ethane-1,2-diamine), N1,N1'-(ethane-1,2-diyl)bis(N2-(2-aminoethyl)ethane-1,2-diamine), N1-(2-(4-(2-aminoethyl)piperazin-1-yl) ethyl)ethane-1,2-diamine, N1-(2-aminoethyl)-N1-methylethane-1,2-diamine, N1-(3-aminopropyl)-N1-methylpropane-1,3-diamine, N1-(3-aminopropyl)-N1-ethylpropane-1,3-diamine, 3-((3-aminopropyl) (methyl)amino)propan-1-ol, 3,3'-(methylazanediyl)bis(propan-1-ol, N1-(3-aminopropyl)-N1-methylbutane-1,4-diamine, 4-((3-aminopropyl)(methyl) amino)butan-1-ol, 4-((3-hydroxypropyl)(methyl)amino) butan-1-ol, 4-((3-hydroxypropyl) (methyl)amino) butan-1-ol, N1-(4-aminobutyl)-N1-methylbutane-1,4-diamine, 4-((4-aminobutyl)(methyl)amino)butan-1-ol, 4,4'-(methylazanediyl)bis(butan-1-ol), 3-((3-aminopropyl)(ethyl)amino) propan-1-ol, 3,3'-(ethylazanediyl)bis(propan-1-ol), N1-(3-aminopropyl)-N1-ethylbutane-1,4-diamine, 4-((3-aminopropyl)(ethyl)amino)butan-1-ol, 4-(ethyl(3-hydroxypropyl)amino)butan-1-ol, N1-(2-aminoethyl)-N1-methylpropane-1,3-diamine , N1-(4-aminobutyl)-N1-ethylbutane-1,4-diamine, 4,4'-(ethylazanediyl) bis(butan-1-ol), 3-((3-aminopropyl)amino)propan-1-ol, N1-(3-aminopropyl)butane-1,4-diamine, 4-((3-hydroxypropyl) amino) butan-1-ol, N1-(4-aminobutyl)butane-1,4-diamine, 3,3'-azanediylbis(propan-1-ol), 4-((3-aminopropyl)amino) butan-1-ol, 4,4'-azanediylbis(butan-1-ol), and N1,N1'-(butane-1,4-diyl)bis(propane-1,3-diamine), 2-(bis(3-aminopropyl)amino)ethan-1-ol, 2-((4-aminobutyl)(3-aminopropyl) amino)ethan-1-ol and 2-(bis(4-aminobutyl)amino)ethan-1-ol.

3. The nucleic acid carrier of claim 1, wherein B is a $C_1$-$C_{28}$ alkyl or $C_2$-$C_{28}$ alkenyl group.

4. The nucleic acid carrier of claim 3, wherein the $C_1$-$C_{28}$ alkyl or $C_2$-$C_{28}$ alkenyl group is substituted with one to four substituents selected from the group consisting of: halogen, —CN, —NO$_2$, —N$_3$, $C_1$-$C_6$ alkyl, halo($C_1$-$C_6$ alkyl), —OR, —NR$_2$, —CO$_2$R, —OC(O)R, —CON(R)$_2$, —OC(O)N(R)$_2$, —NHC(O)N(R)$_2$, —NHC(NH)N(R)$_2$, $C_3$-$C_8$ cycloalkyl, $C_3$-$C_8$ cycloalkenyl, aryl, heteroaryl, and heterocycle, and R is selected from the group consisting of: hydrogen, $C_1$-$C_6$ alkyl, halo($C_1$-$C_6$ alkyl), $C_3$-$C_8$ cycloalkyl, $C_3$-$C_8$ cycloalkenyl, aryl, heteroaryl, and heterocycle.

5. The nucleic acid carrier of claim 4, wherein each cycloalkyl, cycloalkenyl, aryl, heteroaryl, and heterocycle is further substituted with R' and R' is independently selected from the group consisting of: halogen, —CN, —NO$_2$, —N$_3$, $C_1$-$C_6$ alkyl, and halo($C_1$-$C_6$ alkyl).

6. The nucleic acid carrier of claim 3, wherein B is selected from the group consisting of: methyl, ethyl, propyl, butyl, pentyl, hexyl, heptyl, octyl, nonyl decyl, dodecyl, tridecyl, tetradecyl, pentadecyl, hexadecyl, heptadecyl, octadecyl, but-3-en-1-yl, oct-7-en-1-yl, 12-tridecenyl, 14-pentadecenyl, 17-octadecenyl, oleyl, linoleyl, arachidoneyl and ricinoleyl.

7. The nucleic acid carrier of claim 3, wherein B is derived from a fatty acid or derivative thereof.

8. The nucleic acid carrier of claim 7, wherein the fatty acid is selected from the group consisting of: caprylic acid, capric acid, lauric acid, myristic acid, palmitic acid, stearic acid, oleic acid, linoleic acid, linolenic acid, arachidonic acid, eicosapentanoic acid, 2-hydroxy-9-cis-octadecenoic acid, 12-methyltetradecanoic acid, 12-methyltridecanoic acid, 14-methylhexadecanoic acid, 14-methylhexadecanoic acid, 18-methylnonadecanoic acid, 19-methylarachidic acid, isopalmitic acid, isostearic acid, phytanic acid, (±)-2-hydroxyoctanoic acid, (±)-3-hydroxydecanoic acid, (±)-3-hydroxyoctanoic acid, 10-hydroxydecanoic acid, 12-hydroxyoctadecanoic acid, 15-hydroxypentadecanoic acid, 16-hydroxyhexadecanoic acid, 2-hydroxyhexadecanoic acid, 2-hydroxytetradecanoic acid, 2-hydroxydodecanoic acid, DL-α-hydroxystearic acid, DL-β-hydroxylauric acid, DL-β-hydroxymyristic acid, and DL-β-hydroxypalmitic acid, conjugated fatty acids, conjugated isomers of linoleic acid, 9,11-CLA, acetylenic fatty acids, crepenynic acid, allenic fatty acids, laballenic acid, cyclopropenyl fatty acids, and sterculic acid.

9. The nucleic acid carrier of claim 1, wherein the sugar in the deoxy sugar moiety is a furanose monosaccharide, pyranose monosaccharide, disaccharide, oligosaccharide, polysaccharide or sugar derivative.

10. The nucleic acid carrier of claim 1, where the deoxy sugar moiety is 2-deoxy-D-ribose; 6-deoxy-L-tagatose, a 5-deoxy-xylo-, ribo-, or arabinofuranose; 1-deoxy glucose;

2-deoxy glucose; 6-deoxy glucose; 1-deoxy mannose; 2-deoxy galactose; 6-deoxy galactose; 1-deoxy lactose; 6-Azidotrehalose; 6-Azido-2,4-diacetamido-2,4,6-trideoxy-D-mannose; or 6A-Azido -6A-deoxy-β-cyclodextrin.

11. A nanoparticle composition comprising a nucleic acid carrier and an agent enclosed therein, the nucleic acid carrier comprising a structure of formula formula Id:

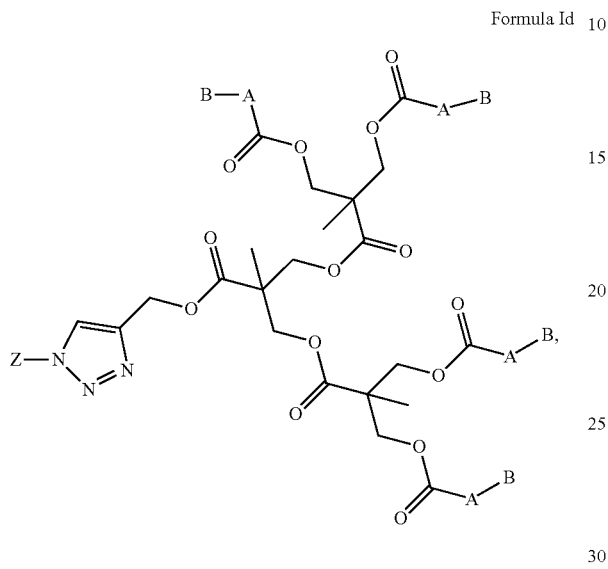

Formula Id wherein A is an amine linker, B is a hydrophobic unit, and Z is a deoxy sugar moiety.

12. The nanoparticle composition of claim 11, wherein the agent is a nucleic acid.

13. The nanoparticle composition of claim 12, wherein the nucleic agent is therapeutic or immunogenic.

14. The nanoparticle composition of claim 13, wherein the agent is a nucleic acid selected from the group consisting of: a polynucleotide, oligonucleotide, DNA, cDNA, RNA, repRNA, siRNA, miRNA, sgRNA, and mRNA.

15. The nanoparticle composition of claim 13, wherein the nucleic acid encodes one or more antigens selected from the group consisting of infectious disease, pathogen, cancer, autoimmunity disease and allergenic disease.

16. The nanoparticle composition of claim 13, wherein the nucleic acid comprises an RNA or DNA capable of silencing, inhibiting or modifying the activity of a gene.

17. The nanoparticle composition of claim 11 further comprising a PEG-lipid.

18. The nanoparticle composition of claim 17, wherein the PEG-lipid is 1,2-dimyristoyl-sn-glycero-3-phosphoethanolamine-N-[methoxy (poly-ethylene glycol) -2000]or 1,2-dimyristoyl-rac-glycero-3-methoxypolyethylene glycol-2000.

19. The nanoparticle composition of claim 17, wherein the nanoparticle composition comprises the PEG-lipid in a range from 1 mol % to 10 mol % of the PEG-lipid per nanoparticle composition.

20. The nanoparticle composition of claim 17 further comprising (1) a phospholipid and/or (2) cholesterol.

21. The nanoparticle composition of claim 20, wherein the phospholipid is 1,2-dioleoyl-sn-glycero-3-phosphoethanolamine (DOPE) or distearoylphosphatidylcholine (DSPC).

22. The nanoparticle composition of claim 20, wherein the nanoparticle composition comprises the phospholipid in a range from 10 mol % to 15 mol % of the phospholipid per nanoparticle composition.

23. The nanoparticle composition of claim 20, wherein the nanoparticle composition comprises the cholesterol in a range from 50 mol % to 75 mol % per nanoparticle composition.

24. A method for treating a disease or condition in a subject comprising: administering to a subject in need thereof a therapeutically effective amount of a nanoparticle composition,
the nanoparticle composition comprising a nucleic acid carrier and an agent enclosed therein, and
the nucleic acid carrier comprising a structure of formula Id:

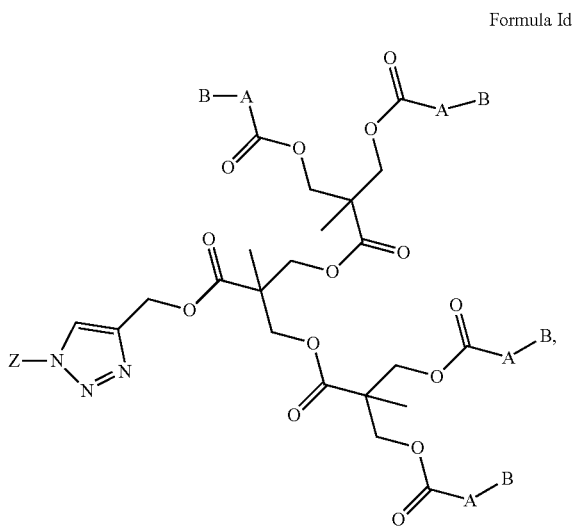

Formula Id wherein A is an amine linker, B is a hydrophobic unit, and Z is a deoxy sugar moiety.

25. The method of claim 24, wherein the nanoparticle composition comprises a therapeutic or immunogenic nucleic acid agent in a range from 0.001 ng nucleic acid to 10 mg nucleic acid per kg body weight of the subject.

26. The method of claim 25, wherein the subject is a mammal.

27. The method of claim 26, wherein the mammal is selected from the group consisting of: human, non-human primate, mouse, rat, dog, cat, horse, or cow.

28. The nucleic acid carrier of claim 1:
wherein A is N1-(3-aminopropyl)-N1-methylpropane-1, 3-diamine, B is ricinoleyl, and Z is 2-deoxy glucose.

* * * * *